(12) United States Patent
Yiv et al.

(10) Patent No.: US 7,064,114 B2
(45) Date of Patent: Jun. 20, 2006

(54) GEL-MICROEMULSION FORMULATIONS

(75) Inventors: Seang Yiv, Woodbury, MN (US); Mingshu Li, St. Paul, MN (US); Osmond D'Cruz, Maplewood, MN (US); Faith M. Uckun, White Bear Lake, MN (US)

(73) Assignee: Parker Hughes Institute, St. Paul, MN (US)

( * ) Notice: Subject to any disclaimer, the term of this patent is extended or adjusted under 35 U.S.C. 154(b) by 359 days.

(21) Appl. No.: 09/957,434

(22) Filed: Sep. 19, 2001

(65) Prior Publication Data

US 2003/0083314 A1 May 1, 2003

(Under 37 CFR 1.47)

Related U.S. Application Data

(63) Continuation-in-part of application No. PCT/US00/07419, filed on Mar. 19, 2000
(60) Provisional application No. 60/125,142, filed on Mar. 19, 1999.

(51) Int. Cl.
*A61K 31/715* (2006.01)
*A61K 31/723* (2006.01)
*A61K 31/731* (2006.01)

(52) U.S. Cl. .................. 514/54; 514/23; 536/123.1; 536/123.12
(58) Field of Classification Search ............ 514/54, 514/23, 50; 536/123.1, 123.12
See application file for complete search history.

(56) References Cited

U.S. PATENT DOCUMENTS

| | | | |
|---|---|---|---|
| 3,850,939 A | 11/1974 | Elslager et al. | |
| 3,970,725 A | 7/1976 | Tugukuni et al. | |
| 4,938,949 A | 7/1990 | Borch et al. | |
| 4,992,271 A | 2/1991 | Hanisch et al. | |
| 5,069,906 A | 12/1991 | Cohen et al. | |
| 5,198,333 A | 3/1993 | Dewanckele et al. | |
| 5,215,976 A * | 6/1993 | Fost et al. ............. | 514/114 |
| 5,314,685 A | 5/1994 | Tyle et al. | |
| 5,411,963 A | 5/1995 | Dreikorn et al. | |
| 5,449,678 A | 9/1995 | Pines et al. | |
| 5,457,105 A | 10/1995 | Barker | |
| 5,468,898 A | 11/1995 | Huang et al. | |
| 5,712,237 A | 1/1998 | Stevens | |
| 5,792,771 A | 8/1998 | App et al. | |
| RE36,256 E | 7/1999 | Spada et al. | |
| 6,051,603 A * | 4/2000 | D'Cruz et al. ......... | 514/492 |
| 6,136,335 A * | 10/2000 | Uckun et al. .......... | 424/430 |

FOREIGN PATENT DOCUMENTS

| | | |
|---|---|---|
| EP | 0 082 385 | 12/1982 |
| WO | WO 94/03157 | 7/1993 |
| WO | WO 95/07696 | 8/1994 |
| WO | WO 95/15758 | 12/1994 |
| WO | WO 95/24190 | 3/1995 |
| WO | WO 95/31969 | 4/1995 |
| WO | WO 96/06616 | 8/1995 |
| WO | WO 96/22976 | 12/1995 |
| WO | WO 96/33745 | 4/1996 |
| WO | WO 96/39143 | 6/1996 |
| WO | WO 96/40113 | 6/1996 |
| WO | WO 96/40116 | 6/1996 |
| WO | WO 96/40648 | 6/1996 |
| WO | WO 99/36063 | 2/1998 |
| WO | WO 98/38984 | 3/1998 |
| WO | WO 98/51284 | 5/1998 |
| WO | WO 99/10325 | 8/1998 |

OTHER PUBLICATIONS

Nath; IN 93772 ,Spermicidal Compositions,Aug. 27, 1966 (Abstract Sent).*
Uckun et al. (Book of Abstracts, 216th ACS National Meeting, Boston, Aug. 23–27 (1998), MEDI–211. American chemical Society: Washington D. C.) (Abstract Sent).*
Andrews et al., *J. American Veterinary Medicine Association*, vol. 202, No. 4, pp. 229–249, 1993 Report of the AVMA Panel of Euthanasia.
Augenbraun MH, et al., *Infect Dis Clin North Am*. 1994; 8:439–48 Sexually Transmitted Diseases in HIV–Infected Persons.
Castle et al., *Biol. Reprod.*, 1997, 56:153–159 Contraceptive Effect of Sperm–Agglutinating Monoclonal Antibodies in Rabbits.
Castle et al., *Contraception*, 1998, 58:51–60 Contraceptive Testing of Vaginal Agents in Rabbits.
Chantler E., *Brit Fam Plann*, 1992;17:118–9 Vaginal spermicides: some current concerns.

(Continued)

*Primary Examiner*—Elvis O. Price
*Assistant Examiner*—Michael C. Henry
(74) *Attorney, Agent, or Firm*—Merchant & Gould P.C.

(57) ABSTRACT

A pharmaceutical composition adapted for use as a spermicide, the composition comprising a gel-microemulsion comprising an oil-in-water microemulsion and a polymeric hydrogel. The gel-microemulsion can be used in a spermicidal method.

Also, a gel-microemulsion pharmaceutical composition adapted for use as a formulation base for additional therapeutic agents. Examples of additional agents include, anti-microbial agents and spermicidal agents. Such gel-microemulsions with additional therapeutic agents can be used in methods for appropriate therapeutic treatment.

Also, a gel-microemulsion pharmaceutical composition that is adapted for use as both a spermicide and formulation base for anti-microbial agents to provide a dual function contraceptive/anti-microbial formulation. Method of using such a composition as a dual function contraceptive/anti-microbial formulation are also included.

62 Claims, 6 Drawing Sheets

OTHER PUBLICATIONS

Charman et al., *Pharmaceutical Research*, vol. 9, No. 1, pp. 87–93, 1992 Self–Emulsifying Drug Delivery Systems: Formulation and Biopharmaceutic Evaluation of an Investigational Lipophilic Compound.

Constantinides, *Pharmaceutical Research*, vol. 12, No. 11, pp. 1561–1572, 1995 Lipid Microemulsions for Improving Drug Dissolution and Oral Absorption: Physical and Biopharmaceutical Aspects.

Danel et al., 1997, *ActaChemica Scandinavica*, 51(3):426–430 Anti–HIV Active Naphthyl Analogues of HEPT and DABO.

Danel et al., 1998, *J. Med. Chem.*, 41:191–198 Synthesis and Anti–HIV–1 Activity of Novel 2,3–Dihydro–7H–thiazolo[3,2–$\alpha$]pyrimidin–7–ones.

D'Cruz et al., 1995, *Biology of Reproduction*, 53(5):1118–1130 B2–Integrein (CD11b/CD18) is the Primary Adhesive Glycoprotein Complex Involved in Neutrophil–Mediated Immune Injury to Human Sperm.

D'Cruz et al., 1998, *Biology Reproduction*, 4(7), pp. 683–693 Spermicidal Activity of Chelated Complexes of bis(cyclopentadienyl)vanadium(IV).

D'Cruz et al., 1998, *Biology Reproduction*, 58:1515–1528 Spermicidal Activity of Metallocene Complexes Containing Vanadium(IV) in Humans.

D'Cruz et al., 1998, *Biology Reproduction*, 59:503–515 Aryl Phosphate Derivatives of Bromo–Methoxy–Azidothymidine Are Dual–Function Spermicides with Potent Anti–Human Immunodeficiency Virus.

D'Cruz et al., 1999, *Biology of Reproduction*, 60:1419–1428 Novel Derivatives of Phenethyl–5–Bromopyridylthiourea and Dihydroalkoxybenzyl–oxopyrimidine Are Dual–Function Spermicides with Potent Anti–Human Immunodeficiency Virus Activity.

D'Cruz et al., 1999, *Biology Reproduction*, 60(2), pp. 345–444 Spermicidal activity of oxovanadium(IV) complexes of 1, 10–phenanthroline, 2,2'–bipyridyl, 5'bromo–2–hydroxyacetophenone and derivatives in humans.

D'Cruz et al., *Biol. Reprod.*, 2001, 64(1), 51–59 Thymidine Kinase–Independent Intracellular Delivery of Bioactive Nucleotides by Aryl Phosphate Derivatives of Bromo–Methoxy Zidovudine (Compounds WHI–05 and WHI–07) in Normal Human Female Genital Tract Epithelial Cells and Sperm.

D'Cruz et al., *Biology of Reproduction*, vol. 62, pp. 37–44, 2000 Structural Requirements for Potent Human Spermicidal Activity of Dual–Function Aryl Phosphate Derivative of Bromo–Methoxy Zidovudine (Compound WHI–07).

D'Cruz et al., *Contraception*, 1999, 59(5):319–331 WHI–05, a Novel Bromo–methoxy Substituted Phenyl Phosphate Derivative of Zidovudine, Is a Dual–Action Spermicide with Potent Anti–HIV Activity.

D'Cruz et al., *Contraception*, 2000, 61(1), 69–76 Evaluation of Subchronic (13 Weeks) and Reproductive Toxicity Potential of Intravaginal Gel–Microemulsion Formulation of a Dual–Function Phenyl Phosphate Derivative of Bromo–Methoxy Zidovudine (Compound WHI–05) in $B_6C_3F_1$ Mice.

D'Cruz et al., *Molecular Human Reproduction*, vol. 5, No. 5, pp. 421–432, 1999 Synthesis, characterization and preclinical formulation of a dual–action phenyl phosphate derivative of bromo–methoxy zidovudine (compound WHI–07) with potent anti–HIV and spermicidal activities.

de Jong, *Therapie*, 1999, 54:11–14 The safety of pharmaceutical excipients.

Diehl et al., *J. Virol*, 1995, 69:2328–2332 Longitudinal Assessment of Feline Immunodeficiency Virus Kinetics in Plasma by Use of a Quantitative Competitive Reverse Transcriptase PCR.

Digenis GA, et al., *Pharm Dev Technol*, 1999;4:421–30 Novel Vaginal Controlled–Delivery Systems Incorporating Coprecipitates of Nonoxynol–9.

Eccleston GM, In: Swarbrick J. Boylan JC, eds. *Encyclopedia of Pharmaceutical Technology*, NY, Marcel Dekker, 1992:375–421 Microemulsions.

Eckstein et al., *J. Reprod Fertil.*, 1969, 20:85–93 Comparison of Vaginal Tolerance Tests of Spermicidal Preparations in Rabbits and Monkeys.

Fischer et al., *Science*, vol. 253, No. 5018, pp. 401–406, 1991 Protein Tyrosine Phosphatases: A Diverse Family of Intracellular and Transmembrane Enzymes.

Furuse K, et al., *J Pharmacobiodyn*, 1983;6:359–72 Studies on Spermicidal Activity of Surfactants .

Greene et al., *ARch Virol*, 1993, 133:51–62 Extensive sequence variation of feline immunodeficiency virus env genes in isolates from naturally infected cats.

Hamawy et al., 1995, *Cellular Signalling*, 7(6):533–544 Protein Tyrosine Phosphorylation as a Mechanism of Signalling in Mast Cells and Basophils.

Heidin, *Cell*, vol. 80, pp. 213–223, 1995 Dimerization of Cell Surface Receptors in Signal Transduction.

Helenious A, et al., *Biochem Biophys Acta*, 1975;415:29–79 Solubilization of Membranes by Detergents.

Hira et al., *International Journal of STD & AIDS*, vol. 8, pp. 243–250, 1997 Condom and nonoxynol–9 use and the incidence of HIV infection in serodiscordant couples in Zambia.

Hooten TM, et al., *JAMA*, 1991;265:64–9 *Escherichia coli* Bacteriuria and Contraceptive Method.

Hunter, *Cell*, vol. 58, pp. 1013–1015, 1989 Protein–Tyrosine Phosphatases: The Other Side of the Coin.

Hynes et al., *Journal of Heterocyclic Chemistry*, vol. 25, No. 4, pp. 1173–1177, 1988 Direct Synthesis of 2,4–Diaminoquinazolines from 2–Fluorobenzonitriles.

Hynes et al., *Journal of Heterocyclic Chemistry*, vol. 28, No. 5, pp. 1357–1363, 1991 Further Studies on the Synthesis of Quinazolines from 2–Fluorobenzonitriles.

International Search Report, PCT/US 00/07066, Aug. 11, 2000.

International Search Report, PCT/US 00/07419, Sep. 7, 2000.

Katz et al., *Proc. Nat'l, Acad. Sci U.S.A.*, 1991, 88:10825–10829 Antiviral activity of 1–docosanol, an inhibitor of lipid–enveloped viruses including herpes simplex.

Klagsbrun et al., *Current Biology*, vol. 3, No. 10, pp. 699–702, 1993 VEGF/VPF: the angiogenesis factor found?.

Kreiss et al., *JAMA*, vol. 268, pp. 477–482, 1998 Efficacy of Nonoxynol 9 Contraceptive Sponge Use in Preventing Heterosexual Acquisition of HIV in Nairobi Prostitutes.

Kulig JW, *Ped Clinic North Am*, 1989;36:717–30 Adolescent Contraception: Nonhormonal Methods.

Kumar et al., 1994, *J. Med. Chem.*, 37:4297–4306 Synthesis, in Vitro, Biological Stability, and Anti–HIV Activity of 5–Halo–6–alkoxy(or azido)–5, 6–dihydro–3'–azido–3'–deoxythymidine Diastereomers as Potential Prodrugs to 3'–Azido–3'–deoxythymidine (AZT).

Lundberg, *J. Pharm Pharmacol*, 1997, 49:16–21 A Submicron Lipid Emulsion Coated with Amphipathic Polyethylene Glycol for Parenteral Administration of Paclitaxel (Taxol).

Mai et al., 1997, *J. Med. Chem.*, 40(10):1447–1454 Dihydro(alkylthio)(naphthylmethyl)oxopyrimidines: Novel Non–Nucleoside Reverse Transcriptase Inhibitors of the S–DABO Series.

Malaviya et al., 1999, *J. Bio. Chem.*, 274(38) 27028–27038 Targeting Janus Kinase 3 in Mast Cells Prevents Immediate Hypersensitivity Reactions and Anaphylaxis.

McGuigan et al., 1993, *J. Med. Chem*, 36:1048–1052 Intracellular Delivery of Bioactive AZT Nucleotides by Aryl Phosphate Derivatives of AZT.

Mendez F, et al., *Contraception*, 1986;34:353–62 Use Effectiveness of a Spermicidal Suppository Containing Benzalkonium Chloride.

Murhammer et al., *Biotechnology Progress*, 1990, vol. 6, pp. 391–397 Sparged Animal Cell Bioreactors: Mechanism of Cell Damage and Pluronic F–68 Protection.

Narla et al., *Clin. Cancer Res.*, 1998, 4:1405–1414 4–(3'Bromo–4'hydroxylephenyl)–amino–6,7–dimethoxyquinazoline: A Novel Quinazoline Derivative with Potent Cytotoxic Activity against Human Glioblastoma Cells.

Narla et al., *Clin. Cancer Res.*, 1998, 4:2463–2471 Inhibition of Human Glioblastoma Cell Adhesion and Invasion by 4–(4'–Hydroxylphenyl)–amino–6,7–dimethoxyquinazoline (WHI–P131) and 4–(3'–Bromo–4'hydroxylphenyl)–amino–6,7–dimethoxyquinazoline (WHI–P154).

Nerukar et al., *Pharmaceutical Research*, 1996, 13:528–534 The Use of Surfactants to Enhance the Permeability of Peptides Through Caco–2 Cells by Inhibition of an Apically Polarized Efflux System.

Nomoto et al., 1990, *Chem. Pharm. Bull.*, 38(6):1591–1595 Studies on Cardiotonic Agents. I. Synthesis of Some Quinazoline Derivatives.

Okada et al., *AIDS Res. Hum Retroviruses*, 1994, 10:1739–46. Superinfection of Cats with Feline Immunodeficiency Virus Subtypes A and B.

OTC Panel, *Federal Register*, 1980;45:82014–49.

Ozawa et al, 1993, *J. Bio. Chem.*, 268(3):1749–1756 $Ca^{2+}$–dependent and $Ca^{2+}$–independent Isozymes of Protein Kinase C Mediate Exocytosis in Antigen–stimulated Rat Basophilic RBL–2H3 Cells.

Patton DL, et al., *Sex Trans Dis.* 1996, 23:489–93 The Vaginal Microflora of Pig–Tailed Macaques and the Effects of Chlorhexidine and Benzalkonium on this Ecosystem.

Pawson, *Nature*, vol. 373, No. 6515, pp. 573–580, 1995 Protein modules and signalling networks.

Plate et al., *Nature*, vol. 359, No. 6398, pp. 845–848, 1992 Vascular endothelial growth factor is a potential tumor angiogenesis factor in human gliomas in vivo.

Pot et al., *Biochimica et Biophysica Acta*, vol. 1136, pp. 35–43, 1992 A thousand and two protein tyrosine phosphatases.

Pouton, *Int'l J. of Pharmaceutics*, No. 27, pp. 335–348, 1985 Self–emulsifying drug delivery systems: assessment of the efficiency of emulsification.

Raymond et al., *Obstet Gynecol*, 1999, 93:896–903 Contraceptive Effectiveness of Two Spermidides: A Randomized Trial.

Rekart ML, *Defic Syndr*, 1992;5:425–27 The Toxicity and Local Effects of the Spermicide Nonoxynol 9.

Rey et al., *Biochem Biophys. Res. Commun.*, 1984, 121:126–33. Characterization of the RNA Dependent DNA Polymerase of a New Human T Lymphotropic Retrovirus (Lymphadenopathy Associated Virus).

Ritschel, *Methods and Findings in Experimental and Clinical Pharmacology*, 1993, 13:205–20 Microemulsions for Improved Peptide Absorption from the Gastrointestinal Tract.

Roddy RE, et al., *Int J STD & HIV*, 1993;4:165–70 A dosing study of nonoxynol–9 and genital irritation.

Roddy RE, et al., *N Engl J Med*, 1998;339:504–10. A Controlled Trial of Nonoxynol 9 Film to Reduce Mail–to–Female Transmission of Sexually Transmitted Diseases.

Rosenstein IJ, et al. *J Infect Dis*, 1998;177:1386–90 Effect on Normal Vaginal Flora of Three Intravaginal Microbicidal Agents Potentially Active Against Human Immunodeficiency Virus Type 1.

Saito et al., *Cell Growth & Differentiation*, vol. 2, pp. 59–65, 1991 Molecular Characterization of Protein Tyrosine Phosphatases.

Sander et al., *Hum. Fertil*, 1941, 6:134–137 A Practical Method for Testing the Spermicidal Action of Chemical Contraceptives.

Schill WB, et al., *Andrologia*, 1981;13:42–9 Ultrastructure of Human Spermatozoa in the Presence of the Spermicide Nonoxinol–9 and a Vaginal Contraceptive Containing Nonoxinol–9.

Schlessinger et al., *Neuron*, vol. 9, pp. 383–391, 1992 Growth Factor Signaling by Receptor Tyrosine Kinases.

Schwinn et al., *Journal of Radioanalytical and Nuclear Chemistry*, vol. 232, Nos. 1–2, pp. 35–37, 1998 The effects of a thio–containing quinazolinedione derivative (MECH) on the lipid oxidation in bilayer liposomes.

Stafford MK, *J Acquir Immune Defic Syndr Hum Retrovirol*, 1998;17:327–31. Safety Study of Nonoxynol–9 as a Vaginal Microbicide: Evidence of Adverse Effects.

Sutherland, *Trends in Biology*, 1998, vol. 16, pp. 41–46 Novel and Established Applications of Microbial Polysaccharides.

Taylor et al., *Annual Review, Cell Biology*, vol. 8, pp. 429–462, 1992 Structural Framework for the Protein Kinase Family.

Tellier et al., *Veterinary Microbiology*, 1997, vol. 57, p. 1–11 Development of FIV–specific Cytolytic T–lymphocyte Responses in Cats Upon Immunisation with FIV Vaccines.

Tenjaria, *Crit. Rev. Ther. Drug Carrier*, 1999, 16:461–521 Microemulsions: An Overview and Pharmaceutical Applications.

Trussell J, et al. *Stud Fam Plann*, 1987;18:237–83. Contraceptive Failure in the United States: A Critical Review of the Literature.

Uckun et al., 1985, *Blut*, 50:19–23 Ex vivo elimination of neoplastic T–Cells from Human Marrow Using an Anti–M, 41,000 Protein Immunotoxin: Protentiation by ASTA Z7557.

Vig et al., 1998, *Bioorganic & Medicinal Chemistry Letters* 8:1461–1466 5–Alkyl–2–[(Methylthiomethyl)Thio]–6–(Benzyl)–Pyrimidine–4–(1H)–Ones as Potent Non–nucleoside Reverse Transcriptase Inhibitors of S–DABO Series.

Vig et al., 1998, *Bioorganic & Medicinal Chemistry*, 6:1789–1797 Rational Design and Synthesis of Phenethyl–5–bromopyridyl Thiourea Derivatives as Potetn Non–nucleoside Inhibitors of HIV Reverse Transcriptase.

Weir et al., *Genitourin Med.*, vol. 71, pp. 78–81, 1995 Nonoxynol–9 use, genital ulcers, and HIV infection in a cohort of sex workers.

Woodcock et al., *Cancer Res.*, 1990, 50:4199–4203 Reveral of the Multidrug Resistance Phenotype with Cremophor EL, a Common Vehicle for Water–insoluble Vitamins and Drugs.

Yiv et al., *Abstracts of Papers American Chemical Society*, vol. 217, pp. 148, 1999 Microemulsion, liposome and mixed micellar formulations for a poorly water soluble quinazoline derivative.

Yiv et al., *Abstracts of Papers American Chemical Society*, vol. 217, No. 1–2, pp. 150, 1999 Development of a vaginal cream for a novel anti–HIV spermicide.

* cited by examiner

GEL-MICROEMULSION FORMULATIONS

PRIORITY

This application is a continuation-in-part application of PCT/US00/07419, filed 19 Mar. 2000 and published in English on Sep. 28, 2000 as International Publication Number WO 00/56366, which claims priority to U.S. Provisional Application No. 60/125,142 filed on 19 Mar. 1999.

FIELD OF THE INVENTION

The present invention relates to a pharmaceutical formulation, and more particularly to a gel-microemulsion formulation. In some embodiments, the gel-microemulsion formulation has spermicidal activity and can be used as a contraceptive. In other embodiments, the gel-microemulsion can act as a formulation base for other therapeutic agents, such as anti-microbial agents to provide an anti-microbial formulation or spermicidal agents to enhance the spermicidal effectiveness of the formulation. In yet other embodiments, the gel-microemulsion, having spermicidal activity, can act as a formulation base for the anti-microbial agents to provide a dual function contraceptive/anti-microbial formulation.

BACKGROUND OF THE INVENTION

At present, all commercially available spermicidal contraceptives have detergent ingredients that disrupt cell membranes. These include the neutral surfactants isononyl-phenyl-polyoxyethylene (9) ether or nonoxynol-9 (N-9), p-menthanyl-phenyl-polyoxyethylene (8,8) ether or menfegol, and isooctyl-phenyl-polyoxyethylene (9) ether or octoxynol-9 (O-9) (Digenis G A, et al., *Pharm Dev Technol*, 1999;4:421–30; Furuse K, et al., *J Pharmacobiodyn*, 1983;6:359–72.) The detergent-type vaginal spermicide, N-9, available without a prescription, is the most commonly used spermicidal contraceptive in the UK and USA (OTC Panel, *Federal Register*, 1980;45:82014–49; Chantler E., *Brit Fam Plann*, 1992;17:118–9.) Worldwide, the cationic surfactant benzalkonium chloride and the anionic detergent sodium docusate (dioctyl sodium sulphosuccinate) are also used as vaginal spermicides (Mendez F, et al., *Contraception*, 1986;34:353–62.) N-9, sodium oxychlorosene, and benzalkonium chloride, have been used as gels, suppositories, ovules, sponges, or film. N-9 has been in use for more than 30 years in creams, gels, foams and condom lubricants. However, in several large studies for users of N-9, the average 6-month pregnancy rate is 26%, and the first-year pregnancy rates range from 11 to 31%. Thus, N-9 is approximately 75% effective in preventing pregnancy (Trussell J, et al. *Stud Fam Plann*, 1987;18:237–83; Kulig J W, *Ped Clinic North Am*, 1989;36:717–30; Raymond E, et al., *Obstet Gynecol*, 1999;93:896–903).

The spermicidal activities of these surfactants are associated with their structural affinity to the membrane lipids (Schill W B, et al., *Andrologia*, 1981;13:42–9; Helenious A, et al., *Biochem Biophys Acta*, 1975;415:29–79). Therefore, the major drawback of using N-9 or other currently used surfactants is their detergent-type effect on epithelial cells and normal vaginal flora. N-9 displays antiviral and spermicidal activities only at cytotoxic doses (D'Cruz O J, et al., *Mol Hum Reprod*, 1999;5:421–32; D'Cruz O J, et al., *Biol Reprod*, 2000;62:37–44). Frequent use of N-9 as a vaginal contraceptive/microbicide has been associated with an increased risk of vaginal or cervical infection, irritation, or ulceration (Niruthisard S R, et al., *Sex Transm Dis*, 1991;18:176–79; Rekart M L, *Defic Syndr*, 1992;5:425–27; Roddy R E, et al., *Int J STD & HIV*, 1993;4:165–70; Weir S S, et al., *Genitourin Med*, 1995;71:78–81). Detergent-type spermicides alter vaginal bacteria or flora, and lead to an increased risk of opportunistic infections (Hooten T M, et al., *JAMA*, 1991;265:64–9.; Stafford M K, *J Acquir Immune Defic Syndr Hum Retrovirol*, 1998;17:327–31.; Rosenstein I J, et al. *J Infect Dis*, 1998;177:1386–90.; Patton D L, et al., *Sex Trans Dis*, 1996;23:489–93.) Such opportunistic infections are known to enhance the susceptibility of the ectocervical epithelium and the endocervical mucosa to HIV-1 infection (Augenbraun M H, et al., *Infect Dis Clin North Am*, 1994; 8:439–48.) Chemical irritation that disrupts the vaginal mucosa may actually enhance the risk of vaginal transmission of sexually transmitted diseases (STDs) including HIV-1, by mucosal erosion and local inflammation (Weir S S, et al., *Genitourin Med*, 1995;71:78–81.;. Kreiss J, *JAMA*, 1992;268:477–82.). In a study conducted among commercial sex workers in Nairobi, in which some of the women used N-9 containing sponges, a significantly higher rate of genital ulceration and HIV-1 seroconversion was found compared with those not using N-9 (Kreiss J, *JAMA*, 1992;268:477–82.).

Furthermore, recent clinical trials have shown that vaginal contraceptive preparations containing N-9 have no effect on the transmission of HIV/AIDS and other STDs when provided as part of an overall program to prevent heterosexual transmission of HIV/AIDS (Hira S K, et al, *Int J STD AIDS*, 1997;8:243–50.; Roddy R E, et al., *N Engl J Med*, 1998;339:504–10.) Since heterosexual transmission of HIV-1 is the predominant mode of the epidemic spread of HIV, new, effective, and safe vaginal spermicides lacking detergent-type membrane toxicity may offer significant clinical advantage over the currently available detergent-type spermicides.

Because vaginal spermicides would likely be used repeatedly over decades, an ideal spermicide should have an established safety record and lack genital epithelial toxicity. Moreover, it should be inexpensive and be produced from commonly available resources and should have a broad specificity for solubilizing drugs effective for prevention of sexual transmission of several STDs including HIV-1.

Therefore, there is a continuing need for new and better spermicidal formulations.

SUMMARY OF THE INVENTION

The inventors have developed novel gel-microemulsion formulations for use as spermicides that in numerous respects overcomes many of the problems of the commercially available detergent-type spermicides. Embodiments of the novel gel-microemulsion spermicide formulations have been show to be very effective as contraceptive agents with reduced levels of toxicity to subjects, and are also useful as formulation bases for anti-microbial agents.

Some novel pharmaceutical formulations embodying the gel-microemulsion of the invention contain common pharmaceutical excipients as the active ingredients, and provide for safe in vitro and in vivo spermicidal activity. In some embodiments, it is contemplated that drug solubilizing agents, such as Cremophor EL® and Phospholipon 90G®, may be active ingredients since these agents were spermicidal against highly motile fraction of sperm. Although, the individual components of some such gel-microemulsion formulations alone lacked spermicidal activity in semen, the combined components in such gel-microemulsion formulations containing the pharmacological excipients rapidly inactivated sperm in human semen. The lack of cytotoxicity of individual components of such formulations in human semen and their synergistic spermicidal property in the gel-microemulsion formulation shows unique clinical potential to formulate them as the active ingredients for a novel and effective contraceptive, such as a vaginal contraceptive for example. In testing, some embodiments of gel-microemulsion formulations of the invention were significantly more effective as a contraceptive than a commercially-available N-9 gel formulation.

Embodiments of the gel-microemulsion of the invention can also be used as an effective formulation base for other agents, for example anti-microbial agents, that can be incorporated into the formulation. Embodiments incorporating anti-microbial agents are particularly useful to prevent the transmission of diseases. Additionally, such embodiments are especially useful as a dual function spermicide/anti-microbial formulation, and can be especially useful in inhibiting the transmission of sexually transmitted diseases, for example AIDS, genital herpes, gonorrhea and chlamydia. In yet other embodiments, additional superficial agents can be incorporated into the formulation to increase the effectiveness of the gel-microemulsion as a spermicide.

One aspect of the invention is directed to a pharmaceutical composition adapted for use as a spermicide, the composition comprising a gel-microemulsion comprising an oil-in-water microemulsion and a polymeric hydrogel. Another aspect is a method of using such a composition as a spermicide.

Another aspect of the invention is directed to a gel-microemulsion pharmaceutical composition adapted for use as a formulation base for additional therapeutic agents. Examples of additional agents include, anti-microbial agents and spermicidal agents. Another aspect is a method of using such a composition as a formulation base for additional therapeutic agents. Another aspect is the use of the combined gel-microemulsion formulation base with additional therapeutic agents for appropriate therapeutic treatment.

Another aspect of the invention is directed to a gel-microemulsion pharmaceutical composition that is adapted for use as both a spermicide and formulation base for anti-microbial agents to provide a dual function contraceptive/anti-microbial formulation. Another aspect is a method of using such a composition as a dual function contraceptive/anti-microbial formulation.

DETAILED DESCRIPTION OF THE INVENTION

Terms and Definitions

Figure 1:
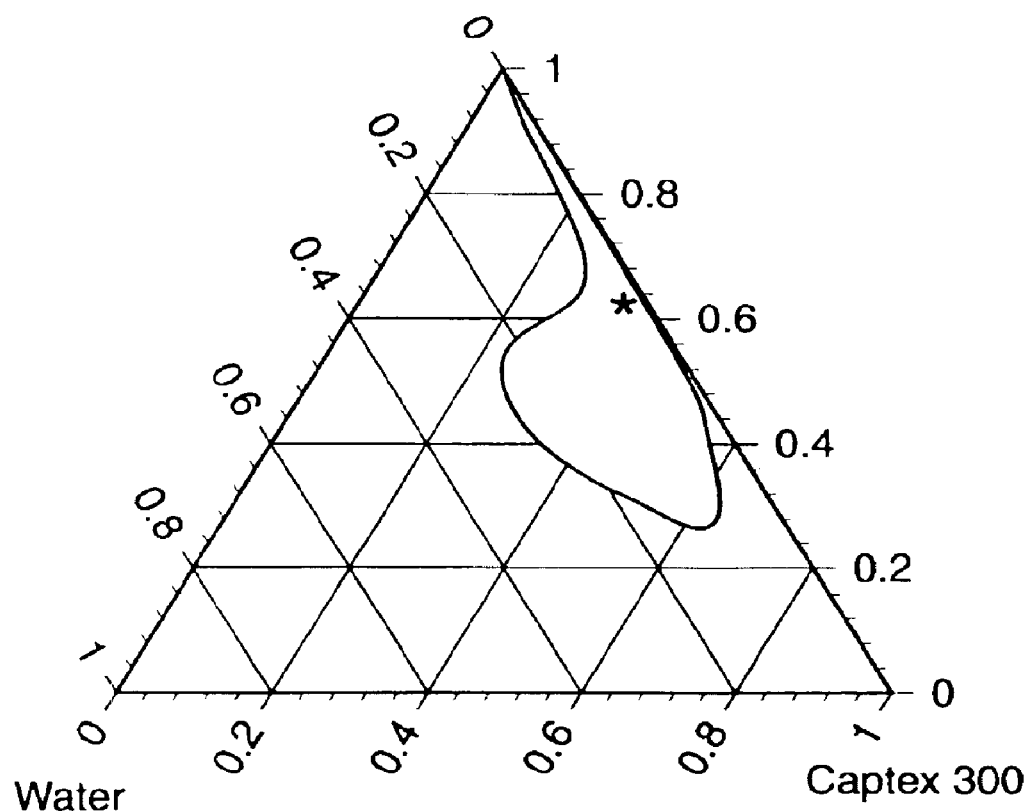
FIG. 1 is a ternary phase diagram of one embodiment of a microemulsion system. The non-grid area represents the single phase microemulsion region. The asterisk represents the microemulsion which was used for GM-4 formulation listed in Table 5.

All scientific and technical terms used in this application have meanings commonly used in the art unless otherwise specified. As used in this application, the following words or phrases have the following meanings, unless otherwise indicated:

"Microemulsions" are thermodynamically stable, transparent, dispersions of water and oil, stabilized by an interfacial film of surfactant molecules. Microemulsions are characterized by their submicron particle size of 0.1 µm or below.

"Lipid" is an inclusive term for fats or fat derived materials.

"Surfactant" is any compound that reduces surface tension when dissolved in water or water solutions, or that reduces interfacial tension between two liquids or between a liquid and a solid. An example of one type are emulsifying agents.

"Humectant" is a substance having affinity for water with stabilizing action on the water content of a material.

As used herein, the terms "analog" or "derivative" are used interchangeably to mean a chemical substance that is related structurally and functionally to another substance. An analog or derivative contains a modified structure from the other substance, and maintains a similar function of the other substance. The analog or derivative need not be, but can be synthesized from the other substance.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt.

"Pharmaceutically acceptable carrier" means any material which, when combined with a biologically active compound, allows the compound to retain biological activity, such as the ability to potentiate antibacterial activity of mast cells and macrophages.

The term "inhibit" means to reduce by a measurable amount, or to prevent entirely.

The term "to treat" means to inhibit or block at least one symptom that characterizes a pathologic condition, in a mammal threatened by, or afflicted with, the condition.

"Mammals" means any class of higher vertebrates that nourish their young with milk secreted by mammary glands, e.g., humans, rabbits, mice, monkeys, etc.

"N-9" means the virucidal/spermicide, nonoxynol-9.

"Organometallic compound" is an organic compound comprised of a metal attached directly to carbon (R-M).

"Coordination compound" is a compound formed by the union of a central metal atom or ion with a nonmetal atom, ion or molecule called a ligand or complexing agent.

"Ligand" or a "complexing agent" is a molecule, ion or atom that is attached to the central metal atom or ion of a coordination compound.

"Monodentate ligand" is a ligand having a single donor atom coordinated to the central metal atom or ion.

"Bidentate ligand" is a ligand having two donor atoms coordinated to the same central metal atom or ion.

"Chelate" or "chelated compound" a type of coordination compound in which a central metal ion is attached by chelated ligand containing two or more non-metal atoms in the same molecule. One or more heterocyclic rings are formed with the central metal atom to form the coordination compounds.

"Oxovanadium (IV) complex" is a coordination compound including vanadium as the central metal atom or ion, and the vanadium has an oxidation state of +4 (IV), and is double bonded to oxygen.

"Metallocene" is an organometallic coordination compound containing cyclopentadienyl rings attached to a transition metal or transition metal halide.

"Vanadocene" is a metallocene including vanadium as the transition metal ion.

"Transition metals" is any of a number of elements in which the filling of the outermost shell to eight electrons within a period is interrupted to bring the penultimate shell from 8 to 18 or 32 electrons. Transition metals include elements 21 through 30, 39 through 48, 57 through 80, and from 89 on.

"Halo" is Br, Cl, F, or I.

"Alkyl" is straight chained or branched chained alkyl, and includes halo-substituted alkyl.

"Alkoxy" is straight chained or branched chained alkoxy, and includes an O in the alkyl group.

"Aryl" refers to monovalent unsaturated aromatic carbocyclic radicals having a single ring, such as cyclopentadienyl or phenyl, or multiple condensed rings, such as naphthyl or anthryl, which can be optionally substituted by substituents such as halogen, alkyl, arylalkyl, alkoxy, aralkoxy, and the like.

"Carboalkoxy" is straight chained or branched chained alkoxy, and includes carbamium carbon.

Gel-Microemulsion Formulations

One aspect of the invention is directed to a pharmaceutical composition adapted for use as a spermicide. The spermicidal activity of the pharmaceutical composition can be in vitro or in vivo. The spermicidal compositions of the present invention are suitable for use, for example, in mammals. The spermicidal compositions comprise a gel-microemulsion. The gel-microemulsions comprise an oil-in-water microemulsion and a thickening agent, such as polymeric gel thickening agent.

The microemulsion generally includes one or more lipids, one or more surfactants, optionally one or more humectants, and water as a diluent.

Suitable lipids include those generally know to be useful for creating oil-in-water microemulsions. Preferred examples include fatty acid glyceride esters, preferably medium chain $C_6$–$C_{12}$ fatty acid glyceride esters, and the like. Preferred $C_6$–$C_{12}$ fatty acid glyceride esters include medium chain $C_6$–$C_{12}$ monoglycerides and triglycerides, with the triglycerides being more preferred. Triglycerides of caprylic/capric acid are particularly suitable for use as the lipid component in the composition. Suitable triglycerides of caprylic/capric acid include Captex 300®, Captex® 355, Captex® 350 and Captex® 200, which are commercially available from Abitec Corp., (Columbus, Ohio), with the most preferred being Captex 300®. Mixtures of suitable lipids can be used.

Suitable surfactants include those generally known to be useful for creating oil-in-water microemulsions wherein lipids are used as the oil component in the microemulsion, and preferably are well suited to aid in emulsifying the particular lipid being used. Non-ionic surfactants are generally preferred. Examples of suitable surfactants include ethoxylated castor oil, and phospholipids. One suitable ethoxylated castor oil is Cremophor EL® commercially available from BASF Corp., (Mount Olive, N.J.). Preferred phospholipids include purified soy bean phospholipid or lecithins such as phosphatidylcholine. One suitable purified soy bean phospholipid or lecithins is Phospholipon® 90G commercially available from American Lecithin (Oxford, Conn.). Other suitable non-ionic surfactants include block copolymers of ethylene oxide and propylene oxide. Suitable commercially available block copolymers of ethylene oxide and propylene oxide include; Pluronic® F-68, Pluronic® F-77, Pluronic® F-87, and Pluronic® F-88, commercially available from BASF Corp., (Mount Olive, N.J.). Mixtures of suitable surfactants can be used. In some preferred embodiments, both ethoxylated castor oil and phospholipids are used as surfactants.

The microemulsion also optionally includes one or more humectants. Preferred humectants include propylene glycol such as 1,2-propanediol, and polyethylene glycol (PEG) with an average molecular weight in the range of 100 to 500, preferably in the range of 150 to 300, and more preferably in the range of 190 to 210. Mixtures of suitable humectants can be used. Preferably both propylene glycol and polyethylene glycol are used as humectants. Suitable propylene glycol is commercially available from under the name Propylene Glycol USP from Sigma Chemical Co., (St. Louis, Mo.). Suitable polyethylene glycol includes Carbowax Polyethylene Glycol 200 commercially available from Union Carbide Corporation (Danbury, Conn.).

Water is used as the diluent, and preferably purified or distilled water is used.

The microemulsions alone can be used, for example, as spermicites or in drug delivery systems to enhance the solubility of poorly water soluble substances, such as some anti-microbial compounds, as will be discussed in more detail below. However, to enhance the usefulness of the microemulsions, especially as an effective spermicide and as a base formulation for anti-microbial compounds in certain application, thickening agents are added.

Therefore, the gel-microemulsion formulation also includes one or more thickening agents, such as a polymeric hydrogel. Generally, the hydrogel is a hydrophilic natural or synthetic gel-forming polymer, preferably, a natural gel-forming polymer. Suitable examples of natural gel-forming polymers include carrageenan, xanthan gum, gum karaya, gum acacia, locust bean gum, guar gum. Mixtures of suitable humectants can be used. Suitable carrageenans include Seaspen® carrageenan and Viscarin® carrageenan commercially available from FMC Corporation (Philadelphia, Pa.). Suitable xanthan gums include XANTURAL™ 75 commercially available from Monsanto Pharmaceutical Ingredients (St. Louis, Mo.) and Rhodigel® commercially available from Rhodia Food Ingredients (Cranbury, N.J.). The formulation can also optionally include one or more additives such as preservatives or antioxidants to help maintain and prolong the useful life of the gel-microemulsion. Preservatives and antioxidants that are generally known, and do not detract significantly from the usefulness of the gel-microemulsion for the particular purpose it is being used, can be incorporated into the gel-microemulsion formulation. Particularly suitable preservatives include sodium benzoate, methyl parabens, propyl parabens, sorbic acid, and the like. Sodium benzoate is most preferred, and is commercially available from Cultor Food Science, Inc. (Ardsley, N.Y.). The prevention of the action of microorganisms in the formulation can be brought about by various antibacterial and antifungal agents, for example, parabens, chlorobutanol, phenol, sorbic acid, thimerosal, and the like.

If desired, other additives, such as colorants, scents, isotonic agents, for example, sugars, buffers or sodium chloride, can be added to the gel-microemulsion to the extent desired, and to the extent that the usefulness of the gel-microemulsion is not disrupted.

The composition is formulated to provide a gel-microemulsion with a submicron particle size, preferably in the range of 30–80 nm. Additionally, the viscosity of the gel-microemulsion is in the range of about 100 to about 1100 centipoise, more preferably from about 150 to about 1000, and more preferably from about 200 to about 1000 centipoise.

Those of skill in the art will recognize that the amounts of each of the individual components used to produce a suitable gel-microemulsion are dependent upon the amounts and type of other components used. Therefore, the amounts and types of components are interdependent.

Those of skill in the art will also recognize that suitable microemulsions can be identified through systematic mapping of ternary phase diagrams. The ternary phase diagram of the microemulsion components used for the preparation of one embodiment of the invention, GM-4, is shown in FIG. 1, and discussed in the Examples below. The non-grid area represents the single phase microemulsion region suitable for use. The concentration of the components can be selected from within this region. The asterisk represents the particular concentration of components of the microemulsion which was used for the GM-4 formulation. Suitable gel-polymer suspensions can then be selected as additives to the microemulsion-based system to obtain a gel of desirable viscosity with high thickening capability and compatibility with the microemulsion. It is preferable that the gel-microemulsion be stable at ambient temperature.

Representative examples of constituent concentration ranges for base components of some gel-microemulsion formulations embodying the invention can be found in Table 1, wherein the values are given in wt. % of the ingredients in reference to the total weight of the formulation.

TABLE 1

| Constituent | Ranges | Ranges | Ranges | Ranges | Ranges |
|---|---|---|---|---|---|
| Lipid | 2 to 25 | 6 to 23 | 8 to 15 | 2 to 20 | 3 to 10 |
| Surfactant | 3 to 30 | 4 to 17 | 8 to 15 | 4 to 17 | 4 to 10 |
| Humectant | 2 to 24 | 3 to 12 | 5 to 10 | 5 to 22 | 12 to 19 |
| Polymer Gel | 0.5 to 4 | 1 to 2 | 1.2 to 1.8 | 0.5 to 2 | 0.8 to 1.2 |
| Additives | 0 to 0.5 | 0.1 to 0.3 | 0.15 to 0.2 | 0 to 0.3 | 0 to 0.2 |
| Water | Balance | Balance | Balance | Balance | Balance |

In some embodiments, the formulation includes the specific constituent concentrations for base components as found in Table 2, wherein the values are given in wt. % of the ingredients in reference to the formulation weight.

TABLE 2

| Ingredients | Ranges | Ranges | Ranges | Ranges |
|---|---|---|---|---|
| Medium Chain Tryglyceride | 6 to 23 | 8 to 15 | 2 to 20 | 3 to 10 |
| Ethoxylated Castor Oil | 3 to 10 | 5 to 9 | 1 to 10 | 2 to 5 |
| Block Copolymer of ethylene oxide and propylene oxide | | | 0.2 to 1 | 0.2 to 0.8 |
| Phospholipid | 1.5 to 6 | 3 to 6 | 1 to 10 | 1 to 5 |
| Propylene Glycol | 1.5 to 6 | 3 to 6 | 2 to 22 | 12 to 19 |
| PEG-200 | 1.5 to 6 | 3 to 6 | | |
| Natural Polymer Gel | 1 to 2 | 1.2 to 1.8 | 0.6 to 2 | 0.8 to 1.2 |
| Preservative | 0 to 0.2 | 0.1 to 0.2 | 0 to 0.3 | 0 to 0.2 |
| Water | Balance | Balance | Balance | Balance |

Preparation of Gel-microemulsions:

A simple procedure allows for the preparation of a gel-microemulsion at even a one-milliliter scale. The following generally describes such a simple procedure: Combine surfactants, hydrophilic components, and the lipids (preferably medium chain tryglycerides) in an appropriate container. Mix the components using a stir bar with mild heat until a clear and homogeneous microemulsion is formed. Remove the composition from the heat, and wait until it reaches room temperature. Add two parts of a pre-prepared polymer dispersion to each part of microemulsion with continued mixing. The resulting gel-microemulsion is a dispersion with a viscosity in the range of 200–1000 centipoise, and a submicron particle size, preferably in the range of 30–80 nm.

Sperimicidal Use of the Gel-microemulsion

The contraceptive compositions of the present invention are preferably administered to a site for contacting sperm, in a dosage which is effective to immobilize sperm. Such compositions are intended particularly for use in mammals, but use outside of mammals is contemplated. It is also contemplated that the compositions may be used as sperm immobilization compositions. It is expected that the present invention will be used by humans in most practical applications.

Preferably, the amount of spermicide employed will be that amount necessary to achieve the desired spermicidal results. Appropriate amounts can be determined by those skilled in the art.

The contraceptive compositions of the present invention may be delivered to the vagina of a mammal by any means known to those skilled in the art. The gel-microemulsion can be applied directly. Other typical forms for delivery of the compositions include, for example, intervaginal devices such as sponges, condoms, including female condoms, suppositories, and films. In addition, the compositions of the present invention may be used as personal care lubricants, such as, for example, condom lubricants, and the like. The contraceptive compositions may be located within or on a condom for example. Inter-vaginal devices may also be used to aid in the administration of the composition as described in U.S. Pat. No. 5,069,906. Further details concerning the materials, ingredients, proportions and procedures of such delivery forms are known to those skilled in the art, and can be selected in accordance with techniques well-known in the art.

It is also contemplated that the formulation of the invention may be incorporated into a spermicidal article such as a vaginal insert, a condom, or other such device, such that when the article is used, the spermicidal can be delivered to contact sperm.

Gel-Microemulsion as a Formulation Base for Other Therapeutic Agents

Another aspect of the invention is the use of the above described gel-microemulsion formulations as formulation bases for incorporating therapeutically active agents. The base gel-microemulsion formulations generally include the components and concentrations discussed above. The therapeutically active agents can include any generally known therapeutic agent where it would be desirable to administer such an agent with a gel-microemulsion formulation. Some embodiments of the gel-microemulsions of the invention are especially suitable as solubilizing vehicles for poorly water soluble compounds. In some preferred embodiments, gel-microemulsion formulations are used, for example, as formulation bases for anti-microbial agents, spermicidal agents, or dual function anti-microbial/spermicidal agents.

Anti-Microbial Gel-Microemulsion Formulations

Suitable examples of anti-microbial therapeutic agents, include anti-viral agents, anti-bacterial agents, anti-fungal agents, and the like. Such agents can be incorporated into the gel-microemulsion formulations to provide for an anti-microbial formulation, or a dual function anti-microbial/spermicidal formulation. Suitable examples of preferred anti-microbial agents include those used for the treatment of sexually transmitted diseases, for example, AIDS (HIV-1, HIV-2, FIV, SIV, etc.) genital herpes, gonorrhea, chlamydia, and the like.

Examples of Preferred Anti-Microbial Agents: Preferred examples of anti-microbial agents, such as anti-viral agents, include those disclosed in the following copending patent applications, which are hereby incorporated by reference herein:

U.S. patent application Ser. No. 09/047,609, which is incorporated herein by reference, and corresponding published PCT Application No. PCT/US99/06381 (International Publication Number WO 99/48902), which is incorporated herein by reference;

U.S. patent application Ser. No. 09/450,082 which is incorporated herein by reference, and corresponding published PCT Application No. PCT/US99/14774 (International Publication Number WO 00/00501) which is incorporated herein by reference; and U.S. patent application Ser. No. 09/107,716, which is incorporated herein by reference.

Examples of preferred anti-microbial/anti-viral compounds disclosed in copending U.S. patent application Ser. No. 09/047,609 and corresponding PCT Pat. application No. PCT/US99/06381, include AZT derivatives disclosed therein. Many of the AZT derivatives disclosed therein also have spermicidal activity. Examples of such anti-microbial AZT derivatives include compounds of the formula:

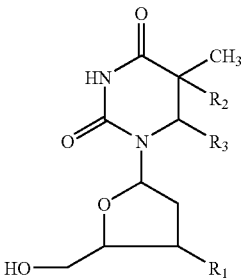

where $R_1$, is H, $N_3$, halo, CN, COOH or $NH_2$, $R_2$ is halo (particularly Cl, Br or I, and more particularly Br) and $R_3$ is alkoxy (particularly C1–3 alkoxy, and more particularly methoxy (—$OCH_3$)). The hydrogenatoms of the $NH_2$ group can be replaced by one or two groups such as —$CH_3$, —$COCH_3$, —Ph, —COPh, and —$CH_2$Ph. Pharmaceutically acceptable salt or ester forms also can be used, such as sodium, potassium or ammonium salts.

The derivatives of the formula above include substitution on the AZT pentose ring member. The derivatives of this aspect of the present invention have the chemical structure illustrated below:

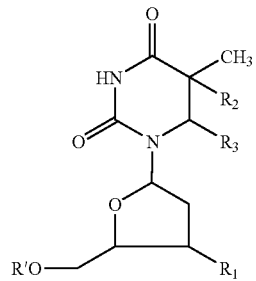

where $R_1$, is H, $N_3$, halo, CN, COOH or $NH_2$, $R_2$ is halo (particularly Cl, Br or I, and more particularly Br), $R_3$ is alkoxy (particularly C1–3 alkoxy, and more particularly methoxy (—$OCH_3$)) and R' is a group that facilitates the passage of the compound into a cell. As in the first formula, the $NH_2$ group can be converted, for example to $NHCH_3$, $NHCOCH_3$, NHPh, NHCOPh, and $NHCH_2$Ph. The R' group can be, for example, H, a phosphate, lipid or fatty acid group. Alternatively, sperm-reactive antibodies or cytokines could be used to derivatize these compounds (as well as those of the first formula) at the R' or $R_1$, positions for targeted delivery. Pharmaceutically acceptable salt or ester forms, such as the sodium, potassium or ammonium salts, can be used as well.

The R' group forms a phosphate group. The H of an —OH member of the phosphate can be replaced with C1–4 alkyl or aryl substituents (e.g. phenyl-, naphthyl- or anthracinylsubstitution), which optionally may be substituted, and SH or NH$_2$ groups can replace the OH of the phosphate, and in each of these cases a H of the NH$_2$ or SH can be replaced in the same manner as the H of the OH group discussed previously. The aryl phosphate group is surprisingly effective in maintaining excellent anti-HIV activity. A general structure of an exemplary aryl phosphate OR' group is illustrated below:

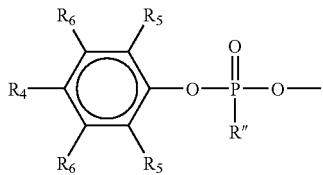

where R$_4$, R$_5$, and R$_6$ are the same or different and are selected from hydrogen, methyl, ethyl, fluoro, chloro, bromo, iodo, dichloro, dibromo, difluoro, trifluoromethyl, nitro, cyano, methoxy, trifluromethoxy and ethoxy, particularly hydrogen, fluoro, bromo and methoxy and R" is an amino acid residue that may optionally be substituted and/or esterified, for example an alaninyl group (—NHCH(Me)COOMe). In the case of the alaninyl group, the methyl group attached to the CH group can be substituted, for example with a phenyl group, and the methyl esterification can be replaced with other C$_2$ or C$_3$ esterification.

Of these compounds, the following compound, hereinafter referred to as WHI-07, is particularly preferred:

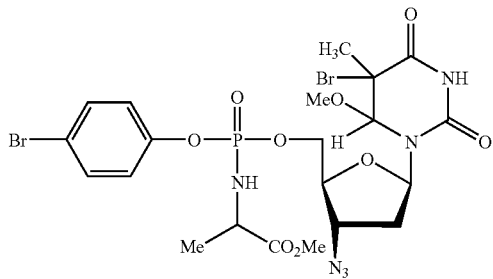

Chemical name: (5R,6R)-and (5S,6S)-5-bromo-6-methoxy-5,6-dihydro-AZT-5'-(para-bromophenyl methoxyalaninyl phosphate).

Examples of preferred anti-microbial, preferably anti-viral, compounds disclosed in U.S. patent application Ser. No. 09/450,082, and corresponding published PCT Application No. PCT/US99/14774; and U.S. patent application Ser. No. 09/107,716, include aryl phosphate derivatives of nucleosides disclosed therein, particularly derivatives of d4T and AZT. Examples of suitable nucleoside derivative disclosed therein include those of the formula:

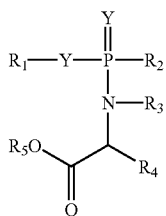

or a pharmaceutically acceptable salt thereof, in which Y is oxygen or sulfur, preferably oxygen; R$_1$ is unsubstituted aryl or aryl substituted with an electron-withdrawing group; R$_2$ is a nucleoside of one of the following formulae:

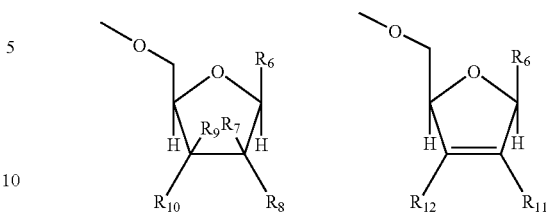

in which R$_6$ is purine or pyrimidine, preferably pyrimidine; and R$_7$, R$_8$, R$_9$, R$_{10}$, R$_{11}$, and R$_{12}$ are independently hydrogen, hydroxy, halo, azido, —NO$_2$, —NR$_{13}$R$_{14}$, or —N(OR$_{15}$)R$_{16}$, in which R$_{13}$, R$_{14}$, R$_{15}$, and R$_{16}$ are independently hydrogen, acyl, alkyl, or cycloalkyl; R$_3$ is hydrogen, acyl, alkyl, or cycloalkyl; R$_4$ is a side chain of an amino acid; or R$_3$ and R$_4$ may be taken together to form the side chain of proline or hydroxyproline; and R$_5$ is hydrogen, alkyl, cycloalkyl, or aryl.

As used in the definitions of the aryl phosphate derivatives of nucleosides disclosed above, and in U.S. patent application Ser. No. 09/450,082, the following terms have the following meanings:

The term "aryl" includes aromatic hydrocarbyl, such as, for example, phenyl, including fused aromatic rings, such as, for example, naphthyl. Such groups may be unsubstituted or substituted on the aromatic ring by an electron-withdrawing group, such as, for example, halo (bromo, chloro, fluoro, iodo), NO$_2$, or acyl. Preferably, aryl substituted with an electron-withdrawing group is bromophenyl, more preferably 4-bromophenyl.

The term "acyl" includes substituents of the formula R$_{17}$C(O)—, in which R$_{17}$ is hydrogen, alkyl, or cycloalkyl.

The term "alkyl" includes a straight or branched saturated aliphatic hydrocarbon chain having from 1 to 6 carbon atoms, such as, for example, methyl, ethyl, propyl, isopropyl (1-methylethyl), butyl, tert-butyl (1,1-dimethylethyl), and the like. Such groups may be unsubstituted or substituted with hydroxy, halo, azido, —NO$_2$, —NR$_{13}$R$_{14}$, or —N(OR$_{15}$)R$_{16}$, in which R$_{13}$, R$_{14}$, R$_{15}$, and R$_{16}$ are as defined above.

The term "cycloalkyl" includes a saturated aliphatic hydrocarbon ring having from 3 to 7 carbon atoms, such as, for example, cyclopropyl, cyclobutyl, cyclopentyl, cyclohexyl, and the like. Such groups may be unsubstituted or substituted with hydroxy, halo, azido, —NO$_2$, —NR$_{13}$R$_{14}$, or —N(OR$_{15}$)R$_{16}$ in which R$_{13}$, R$_{14}$, R$_{15}$, and R$_{16}$ are as defined above.

The term "purine" includes adenine and guanine.

The term "pyrimidine" includes uracil, thymine, and cytosine. Preferably, the pyrimidine is thymine.

The term "side chain of an amino acid" is the variable group of an amino acid and includes, for example, the side chain of glycine, alanine, arginine, asparagine, aspartic acid, cysteine, cystine, glutamic acid, glutamine, hydroxylysine, isoleucine, leucine, lysine, methionine, phenylalanine, serine, threonine, tryptophan, tyrosine, valine, and the like. Preferably, the side chain of an amino acid is the side chain of alanine or tryptophan.

Generally, compounds substituted with an electron-withdrawing group, such as an ortho- or para-substituted halogen or NO$_2$ provide for more efficient hydrolysis to active inhibitory compounds. Preferred is halogen substitution, and most preferred are para-bromo substitution and para-chloro substitution.

Preferred nucleoside derivative disclosed therein include those of the formulas:

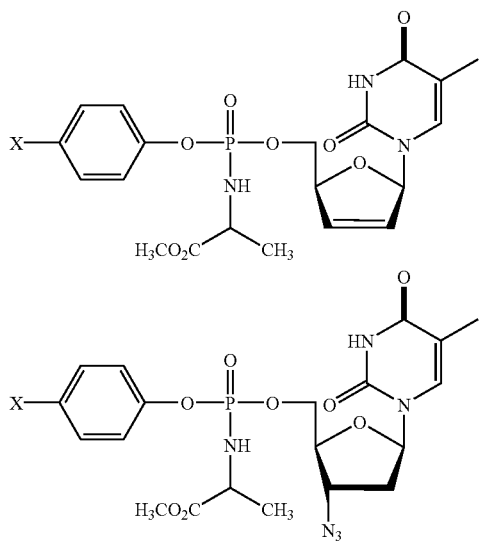

wherein X is an electron withdrawing group, for example halo or NO$_2$, and most preferably, X is bromo or chloro.

Gel-Microemulsion Formulations with Additional Spermicidal Agents

Suitable examples of spermicidal agents, include any spermicidal agent generally known that is compatible for formulation with the gel-microemulsion. Such agents can be incorporated into the gel-microemulsion formulations to provide for additional spermicidal activity of the formulation. Many of the spermicidal agents discussed below also have anti-microbial activity, such as anti-viral activity, and can be incorporated into the formulations as an anti-microbial agent as well as a spermicidal agent.

Preferred Spermicidal Agents For Incorporation Into the Gel-Microemulsion Formulation: Preferred examples of spermicidal agents include those disclosed in the following copending patent applications:

U.S. patent application Ser. No. 09/008,898, which is incorporated herein by reference, and corresponding published PCT Application No. PCT/US99/01171 (International Publication Number WO 99/36063), which is incorporated herein by reference;

U.S. patent application Ser. No. 09/187,115, which is incorporated herein by reference;

U.S. patent application Ser. No. 09/224,677, which is incorporated herein by reference.

Examples of preferred spermicidal compounds disclosed in copending U.S. patent application Ser. No. 09/008,898, and corresponding published PCT Application No. PCT/US99/01171, include the vanadium (IV) compounds disclosed therein. Examples of such vanadium (IV) compounds include organometallic cyclopentadienyl vanadium IV complexes. Preferred such compounds include: vanadocene dichloride, bis(methylcyclopentadienyl) vanadium dichloride, vanadocene dibromide, vanadocene diiodide, vanadocene diazide, vanadocene dicyanide, vanadocene dioxycyanate, vanadocene dithiocyanate, vanadocene diselenocyanate, vanadocene ditriflate, vanadocene monochloro oxycyanate, vanadocene monochloroacetonitrilo tetrachloro ferrate, vanadocene acetylacetonato monotriflate, vanadocene bipyridino ditriflate, vanadocene hexafluoro acetylacetonato monotriflate, vanadocene acetylhydroxamato monotriflate, and vanadocene N-phenyl benzohydroxamato monotriflate. Particularly preferred compounds include vanadocene diselenocyanate, and vanadocene dichloride.

Examples of preferred spermicidal compounds disclosed in copending U.S. patent application Ser. No. 09/187,115 include oxo-vanadium (IV) compounds disclosed therein. Preferred the oxovanadium (IV) complexes include at least one bidentate ligand. Suitable bidentate ligands include N,N'; N,O; and O,O' bidentate ligands. Examples of suitable bidentate ligands include bipyridyl, bridged bipyridyl, and acetophenone. Particularly, preferred oxovanadium compounds are those having the formulas shown and described below.

Some suitable oxo-vanadium (IV) compounds include a bidentate ligand wherein the bidentate ligand is a bipyridyl and the oxovanadium IV complex has the general formulae:

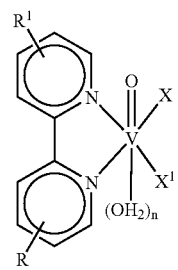

where R and R$_1$, are the same or different and are independently selected from: H, lower alkyl, halogen, lower alkoxy, halogenated alkyl, cyano, carboalkoxy (e.g. C$_2$–C$_6$) and nitro; X and X$^1$ are the same or different and are independently selected from: monodentate and bidentate ligands; and n is 0 or 1.

Other suitable oxo-vanadium (IV) compounds have a bidentate ligand wherein the bidentate ligand is a bridged bipyridyl and the oxovanadium IV complex has the general formulae:

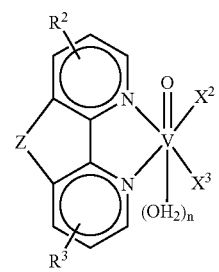

where R$^2$ and R$^3$ are the same or different and are selected from H, lower alkyl, halogen, lower alkoxy, halogenated alkyl, cyano, carboalkoxy (e.g. C$_2$–C$_6$) and nitro; X$^2$ and X$^3$, are the same or different and are selected from monodentate and bidentate ligands; Z is selected from O, CH$_2$, CH$_2$—CH$_2$, and CH=CH; and n is 0 or 1.

Other suitable oxo-vanadium (IV) compounds have a bidentate ligand wherein the bidentate ligand is a bridged bipyridyl, and the bridged bipyridyl is phenanthroline, and the oxovanadium IV complex has the general formulae:

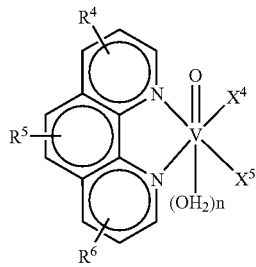

where $R^4$, $R^5$ and $R^6$ are the same or different and are independently selected from: H, lower alkyl, halogen, lower alkoxy, halogenated alkyl, cyano, carboalkoxy (e.g. $C_2$–$C_6$) and nitro; $X^4$ and $X^5$ are the same or different and independently selected from: monodentate and bidentate ligands; and n is 0 or 1.

Other suitable oxo-vanadium (IV) compounds have a bidentate ligand wherein the bidentate ligand is an O,O' bidentate ligand, the oxovanadium IV complex has the general formulae:

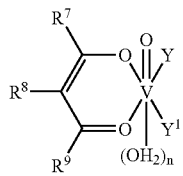

where $R^7$ and $R^9$ are the same or different and are independently selected from: H, lower alkyl, lower alkoxy, and halogenated alkyl; $R^8$ is selected from H, lower alkyl, halo, lower alkoxy, and halogenated alkyl; Y and $Y^1$ are the same or different and independently selected from the group consisting of: monodentate and bidentate ligands; and n is 0 or 1.

Preferred monodentate ligands for the oxovanadium complex include $H_2O$, halides and carboxylates. Preferred bidentate ligands include N,N' bidentate ligands, N,O bidentate ligands, and O,O' bidentate ligands. Examples of suitable N,N' bidentate ligands include diamines and other such known suitable N,N' bidentate ligands. Examples of diamines include bipyridal, derivatives of bipyridal, bridged bipyridal, such as phenanthroline, derivatives of phenanthroline, and other such compounds. Examples of suitable N,O bidentate ligands include amino acids and Schiff base type groups. Examples of suitable O,O' bidentate ligands include dicarboxylate, 2-hydroxyacetophenone, acetylacetone type and catechol type groups.

Particularly useful oxo-vanadium (IV) complexes are the following:
 (diaqua)(2,2'-bipyridyl)oxovanadium(IV) sulfate;
 (aqua)bis(2,2'-bipyridyl)oxovanadium(IV) sulfate;
 (diaqua)(4,4'-dimethyl-2,2'-bipyridyl)oxovanadium(IV) sulfate;
 (aqua)bis(4,4'-dimethyl-2,2'-bipyridyl)oxovanadium(IV) sulfate;
 (diaqua)(1,10-phenanthroline)oxovanadium(IV) sulfate;
 (aqua)bis(1,10-phenanthroline)oxovanadium(IV) sulfate;
 (diaqua)(4,7-dimethyl-1,10-phenanthroline)oxovanadium (IV) sulfate;
 (aqua)bis(4,7-dimethyl-1,10-phenanthroline) oxovanadium(IV) sulfate;
 (diaqua)(5-chloro-1,10-phenanthroline)oxovanadium(IV) sulfate;
 (aqua)bis(5-chloro-1,10-phenanthroline)oxovanadium (IV) sulfate; and
 bis(5'-bromo-2'-hydroxyacetophenone)oxovanadium (IV).

Examples of preferred spermicidal compounds disclosed in copending U.S. patent application Ser. No. 09/224,677 include phenethyl-5-bromopyridylthiourea (PBT) and dihydroxalkoxybenzylopyrimidine (DABO) derivatives disclosed therein.

Examples of such PBT derivatives include those having the following chemical formula, or a pharmaceutically acceptable salt thereof:

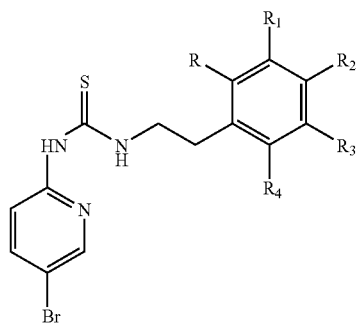

where R, $R_1$, $R_2$, $R_3$, and $R_4$ are independently hydrogen, F, Cl, Br, or I, and where at least one of R, $R_1$, $R_2$, $R_3$, and $R_4$ is F, Cl, Br, or I. Preferably, one of R, $R_1$, $R_2$, $R_3$, and $R_4$ in structure above is F or Cl. Some, but not all of the suitable halogen-substituted PBT derivatives of the invention are listed below:
 N-[2-(2-fluorophenethyl)]-N'-[2-(5-bromopyridyl)]-thiourea
 N-[2-(2-chlorophenethyl)]-N'-[2-(5-bromopyridyl)]-thiourea
 N-[2-(3-fluorophenethyl)]-N'-[2-(5-bromopyridyl)]-thiourea
 N-[2-(3-chlorophenethyl)]-N'-[2-(5-bromopyridyl)]-thiourea
 N-[2-(4-fluorophenethyl)]-N'-[2-(5-bromopyridyl)]-thiourea
 N-[2-(4-chlorophenethyl)]-N'-[2-(5-bromopyridyl)]-thiourea.

One of the more preferred PBT derivatives is N-[2-(2-fluorophenethyl)]-N'-[2-(5-bromopyridyl)]-thiourea (F-PBT) which has the chemical structure shown below:

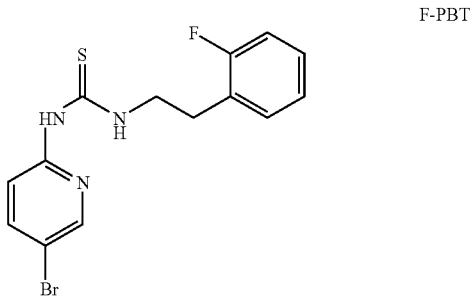

PBT derivatives can be synthesized as described in Vig et al., BIOORG. MED. CHEM., 6:1789–1797 (1998). In brief, 2-amino-5-bromopyridine is condensed with 1,1-thiocarbonyl diimidazole to furnish the precursor thiocarbonyl derivative. Further reaction with appropriately halogen-substituted phenylethylamine gives the target halogenated PBT derivatives.

Examples of suitable DABO derivatives include those of the formula, or a pharmaceutically acceptable salt thereof:

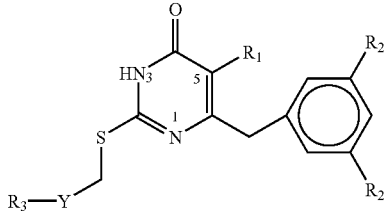

where $R_1$ and $R_2$ are alike or different, and are hydrogen, halo, alkyl, alkenyl, hydroxy, alkoxy, thioalkyl, thiol, phosphino, ROH, or RNH group, where R is alkyl. Preferably, one or more of $R_1$ and $R_2$ is an alkyl having 1 to 3 carbonatones, ($C_1$–$C_3$), such as methyl (Me), ethyl (Et), or isopropyl (i-Pr). Preferably, $R_1$ is alkyl, alkenyl, ROH, or $RNH_2$. $R_2$ is preferably halo, alkyl, or $C_1$–$C_3$ alkoxy;

Y is S or O, and is preferably S. $R_3$ is alkyl, alkenyl, aryl, aralkyl, ROH, or RNH group, where R is alkyl, and is preferably $C_1$–$C_3$ alkyl.

Preferred DABO derivatives include compounds having the chemical structure shown below, or a pharmaceutically acceptable salt thereof:

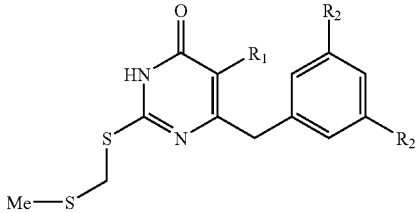

where $R_1$ is Me, Et, or i-Pr and $R_2$ is H or Me.

Some, but not all, of the suitable DABO derivative compounds include compounds (a) through (d) listed below, or a pharmaceutically acceptable salt thereof:

(a) 5-methyl-2-[(methylthiomethyl)thio]-6-benzyl-pyrimidin-4-1H-one, (b) 5-ethyl-2-[(methylthiomethyl)thio]-6-benzyl-pyrimidin-4-1H-one, (c) 5-isopropyl-2-[(methylthiomethyl)thio]-6-benzyl-pyrimidin-4-1H-one, and (d) 5-isopropyl-2-[(methylthiomethyl)thio]-6-(3,5-dimethylbenzyl)-pyrimidin-4-1H-one.

One of the more preferred DABO derivatives is the compound 5-isopropyl-2-[(methylthiomethyl)thio]-6-(benzyl)-pyrimidin-4-(1H)-ones (S-DABO), and pharmaceutically acceptable salts thereof, which is exemplified by the chemical structure shown below:

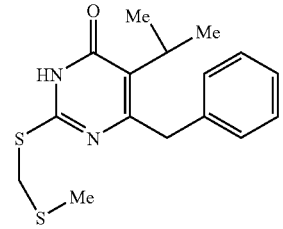

DABO derivatives can be prepared as described in described in Vig et al., *BIOORG MED CHEM LETTERS*, 8:1461–1466 (1998). The general synthesis scheme for the preparation of DABO derivatives (a) through (d) listed above is as follows:

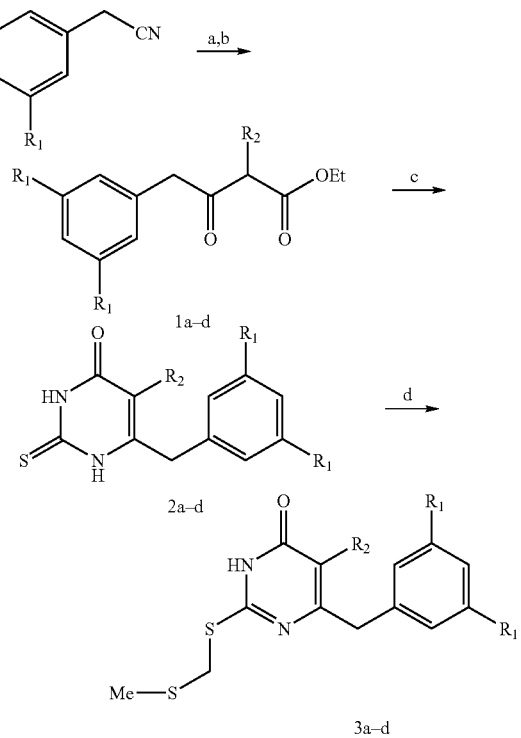

Reagents and conditions: a) $R_2$CHBrCOOEt/Zn/THF, b) HCl(aq), c) $(H_2N)_2$CS/Na/EtOH, d) DMF, $K_2CO_3$, Chloromethyl methyl sulfide, 15h.

Briefly, ethyl-2-alkyl-4-(phenyl)-3-oxobutyrates 1a–d were obtained from commercially available phenyl acetonitrile. The β-ketoesters were condensed with thiourea in the presence of sodium ethoxide to furnish the corresponding thiouracils 2a–d. Compounds (1a–d and 2a–d) were produced by a methods previously described (Danel, K. et al., *Acta Chemica Scandinavica*, 1997, 51, 426–430; Mai, A. et al., *J. Med. Chem.*, 1997, 40, 1447–1454; Danel, K. et al., *J. Med. Chem.*, 1998, 41, 191–198).

Subsequent reaction of thiouracil with methylchloromethyl sulfide in N,N-dimethylformamide (DMF) in the presence of potassium carbonate afforded compounds 3a–d in moderate yields. A mixture of thiouracil compound 2 (1 mmol), methylchloromethyl sulfide (1 mmol), and potassium carbonate (1 mmol) in anhydrous DMF (5ml) was stirred overnight at room temperature. After treatment with water (50 ml), the solution was extracted with ethyl acetate (3×50 ml). The combined extracts were washed with saturated NaCl (2×50 ml), dried (MgSO$_4$), filtered and concentrated in vacuo to give the crude products 3a–d which were purified by column chromatography (hexane: ethyl acetate eluent).

Other examples of therapeutic agents includes vanadium (IV) complexes containing a substituted or un-substituted catecholate ligand. Examples of such compounds include complexes having the following structural formula, or pharmaceutically acceptable salts thereof:

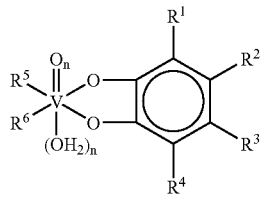

wherein $R^1$, $R^2$, $R^3$ and $R^4$ are the same or different and are independently selected from H, halo, OH$_2$, O$_3$SCF$_3$, N$_3$, CN, OCN, SCN, SeCN, NO$_2$, C$_1$–C$_4$ alkyl, C$_1$–C$_4$ alkoxy, and aryl; and n is 0 or 1; and $R^5$ and $R^6$ are the same or different and are either monodentate ligands or $R^5$ and $R^6$ together comprise a bidentate ligand.

Suitable monodentate ligands include, for example, aryl, halo, H$_2$O, O$_3$SCF$_3$, N$_3$, COOH, CN, OCN, SCN, SeCN, NO$_2$, C$_1$–C$_4$ alkyl, C$_1$–C$_4$ alkoxy. Preferred monodentate ligands comprises one or more unsubstituted or substituted aromatic ring. More preferred monodentate ligands comprise substituted or un-substituted cyclopentadienyl ligands.

Suitable bidentate ligands include, for example, N,N'; N,O; and O,O' bidentate ligands. Examples of suitable N, N' bidentate ligands include diamines and other such known suitable N,N' bidentate ligands. Examples of diamines include bipyridal, derivatives of bipyridal, bridged bipyridal, such as phenanthroline, derivatives of phenanthroline, and other such compounds. Examples of suitable N,O bidentate ligands include amino acids and Schiff base type groups. Examples of suitable O,O' bidentate ligands include dicarboxylate, 2-hydroxyacetophenone, acetylacetone type and catechol type groups. Preferred bidentate ligands comprise one or more aromatic ring. Preferred examples of suitable bidentate ligands comprising aromatic rings include substituted or un-substituted bipyridyl, bridged bipyridyl, and acetophenone ligands. One example of a bridged bipyridyl includes phenanthroline.

Some preferred vanadium (IV) catecholate complexes include "bent sandwich" vanadocene monocatecholate complexes having the following structure formula, or pharmaceutically acceptable salts thereof:

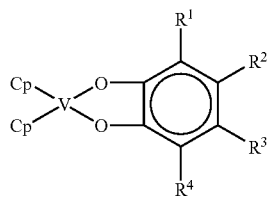

wherein Cp is unsubstituted cyclopentadienyl, or cyclopentadienyl substituted with one or more substituents selected from substituted or unsubstituted aryl, C$_1$–C$_4$ alkyl, C$_1$–C$_4$ alkoxy, halo, OH$_2$, O$_3$SCF$_3$, N$_3$, CN, OCN, SCN, SeCN, NO$_2$. Preferably, Cp is unsubstituted cyclopentadienyl.

$R^1$, $R^2$, $R^3$ and $R^4$ are the same or different and are independently selected from H, halo, OH$_2$, O$_3$SCF$_3$, N$_3$, CN, OCN, SCN, SeCN, NO$_2$, C$_1$–C$_4$ alkyl, and C$_1$–C$_4$ alkoxy Preferably, electron donating groups, for example electron donating alkyl groups, are present as substituents of the catecholate ring in positions $R^1$, $R^2$, $R^3$ and/or $R^4$.

Particularly preferred such compounds include vanadocene catecholate, vanadocene mono-tertbutyl catecholate, and vanadocene 1,3-diisopropyl catecholate.

Another example of vanadium (IV) catecholate complexes include complexes having a bidentate ligand wherein the bidentate ligand is a bipyridyl has the general formula shown below, or pharmaceutically acceptable salts thereof:

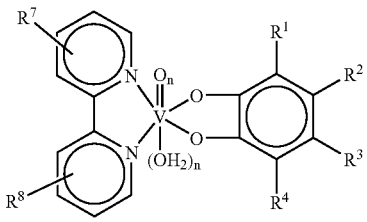

where $R^7$ and $R^8$ are the same or different and are independently selected from: H, aryl, C$_1$–C$_4$ alkyl, halo, C$_1$–C$_4$ alkoxy, carboalkoxy (e.g. C$_2$–C$_6$), cyano, and nitro; n is 0 or 1; $R^1$, $R^2$, $R^3$ and $R^4$ are the same or different and are independently selected from H, halo, OH$_2$, O$_3$SCF$_3$, N$_3$, CN, OCN, SCN, SeCN, NO$_2$, C$_1$–C$_4$ alkyl, and C$_1$–C$_4$ alkoxy.

Another example of vanadium (IV) catecholate complexes include complexes having a bidentate ligand wherein the bidentate ligand is a bridged bipyridyl has the general formula shown below, or pharmaceutically acceptable salts thereof:

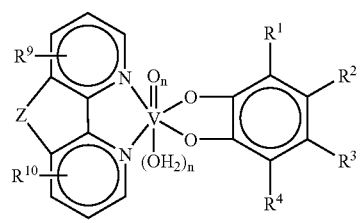

where $R^9$ and $R^{10}$ are the same or different and are selected from H, aryl, C$_1$–C$_4$ alkyl, halogen, C$_1$–C$_4$ alkoxy, halogenated alkyl, cyano, carboalkoxy (e.g. C$_2$–C$_6$) and nitro; Z is selected from O, CH$_2$,CH$_2$—CH$_2$, and CH=CH; n is 0 or 1; and halo, OH$_2$, O$_3$SCF$_3$, N$_3$, CN, OCN, SCN, SeCN, NO$_2$, C$_1$–C$_4$ alkyl, and C$_1$–C$_4$ alkoxy.

Another example of vanadium (IV) catecholate complexes include complexes having a bidentate ligand wherein the bidentate ligand is a bridged bipyridyl, and the bridged bipyridyl is phenanthroline, has the general formula shown below, or pharmaceutically acceptable salts thereof:

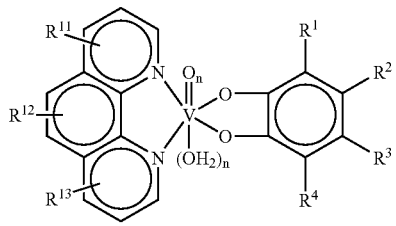

where $R^{11}$, $R^{12}$ and $R^{13}$ are the same or different and are independently selected from: H, aryl, C$_1$–C$_4$ alkyl, halogen, lower alkoxy, halogenated alkyl, cyano, carboalkoxy (e.g. $C_2$–$C_6$) and nitro; n is 0 or 1; and $R^1$, $R^2$, $R^3$ and $R^4$ are the same or different and are independently selected from H, halo, $OH_2$, $O_3SCF_3$, $N_3$, CN, OCN, SCN, SeCN, $NO_2$, $C_1$–$C_4$ alkyl, and $C_1$–$C_4$ alkoxy.

Another example of vanadium (IV) catecholate complexes include complexes having a bidentate ligand wherein the bidentate ligand is an O,O' bidentate ligand, and the complex has the general formula VI, is shown below, or pharmaceutically acceptable salts thereof:

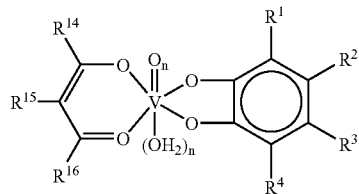

where $R^{14}$ and $R^{16}$ are the same or different and are independently selected from: H, aryl, $C_1$–$C_4$ alkyl, and $C_1$–$C_4$ alkoxy, and halogenated alkyl; $R^{15}$ is selected from H, $C_1$–$C_4$ alkyl, halo, $C_1$–$C_4$ alkoxy, and halogenated alkyl; n is 0 or 1; and $R^1$, $R^2$, $R^3$ and $R^4$ are the same or different and are independently selected from H, halo, $OH_2$, $O_3SCF_3$, $N_3$, CN, OCN, SCN, SeCN, $NO_2$, $C_1$–$C_4$ alkyl, and $C_1$–$C_4$ alkoxy.

Formulation of the Gel-microemulsions Formulations Including Additional Therapeutic Agents Gel-microemulsions formulations including additional therapeutic agents, for example the anti-microbial agents or spermicidal agents discussed above, are formulated and prepared in substantially the same way as the primary gel-microemulsions discussed above, with the only difference being the addition of the additional therapeutic agent. The amount of additional ingredient added is dependent upon the desired effective amount of the ingredient in the final gel-microemulsion formulation. It is still desirable to provide a dispersion with a viscosity in the range of 200–1000 centipoise, and a submicron particle size, preferably in the range of 30–80 nm.

Representative examples of constituent concentration ranges for base components of some gel-microemulsion formulations embodying the invention can be found in Table 3, wherein the values are given in wt. % of the ingredients in reference to the total weight of the formulation.

In embodiments, the formulation includes the specific constituent concentrations for base components as found in Table 4, wherein the values are given in wt. % of the ingredients in reference to the formulation weight.

TABLE 4

| Ingredients | Ranges | Ranges | Ranges | Ranges |
| --- | --- | --- | --- | --- |
| Anti-microbial agent or Spermicidal agent, or mixtures thereof | up to 2 | 1 to 2 | up to 2 | 1 to 2 |
| Medium Chain Tryglyceride | 6 to 23 | 8 to 15 | 2 to 20 | 3 to 10 |
| Ethoxylated Castor Oil | 3 to 11 | 5 to 9 | 1 to 10 | 2 to 5 |
| Block Copolymer of ethylene oxide and propylene oxide | | | 0.2 to 1 | 0.2 to 0.8 |
| Phospholipid | 1.5 to 6 | 3 to 6 | 1 to 10 | 1 to 5 |
| Propylene Glycol | 1.5 to 6 | 3 to 6 | 5 to 22 | 12 to 19 |
| PEG-200 | 1.5 to 6 | 3 to 6 | | |
| Natural Hydrogels | 1 to 2 | 1.2 to 1.8 | 0.6 to 2 | 0.8 to 1.2 |
| Preservative | 0.1 to 0.2 | 0.15 to 0.2 | 0 to 0.3 | 0 to 0.2 |
| Water | Balance | Balance | Balance | Balance |

The following generally describes a simple formulation procedure for producing formulations with additional therapeutic agents, such as an anti-microbial agent or a spermicidal agent: Combine surfactants, hydrophilic components, and the lipids (preferably medium chain tryglycerides) in an appropriate container. Mix the components using a stir bar with mild heat until a clear and homogeneous microemulsion is formed. Add the appropriate amount of therapeutic agents with continued stirring for approximately 10 minutes to assure complete solubilization of the drug. Remove the composition from the heat, and wait until it reaches room temperature. Add two parts of a pre-prepared polymer dispersion to each part of microemulsion with continued mixing. The resulting gel-microemulsion is a dispersion with a viscosity in the range of 200–1000 centipoise, and a submicron particle size, preferably in the range of 30–80 nm.

Use Therapeutic Agent Containing Gel-Microemulsion Formulations

When used as a spermicide, or a dual function spermicide/anti-microbial composition, the gel-microemulsion formulations resulting from the addition of additional therapeutic agents are contemplated for used in generally the same manner as the gel-microemulsion spermicide use discussed above. However, it is contemplated that formulations including other therapeutic agents, for example anti-viral agents, can be used in non-spermicidal applications.

In such applications, the formulation is preferably administered to a site appropriate for the therapeutic activity desired in a dosage which is effective to effectuate the desired therapeutic effect. For example, in anti-microbial applications, the formulation is preferably administered to a site appropriate for desired anti-microbial activity in a

TABLE 3

| Constituent | Ranges | Ranges | Ranges | Ranges | Ranges | Ranges |
| --- | --- | --- | --- | --- | --- | --- |
| Therapeutic Ingredient | up to 10 | up to 5 | up to 2 | up to 10 | up to 5 | up to 2 |
| Lipid | 2 to 25 | 6 to 23 | 8 to 15 | 2 to 25 | 2 to 20 | 3 to 10 |
| Surfactant | 3 to 30 | 4 to 17 | 8 to 15 | 3 to 30 | 4 to 17 | 4 to 10 |
| Humectant | 2 to 24 | 3 to 12 | 5 to 10 | 2 to 24 | 5 to 22 | 12 to 19 |
| Polymer Gel | 0.5 to 4 | 1 to 2 | 1.2 to 1.8 | 0.5 to 4 | 0.6 to 2 | 0.8 to 1.2 |
| Additives (e.g. Preservatives) | 0 to 0.5 | 0.1 to 0.3 | 0.15 to 0.2 | 0 to 0.5 | 0 to 0.3 | 0 to 0.2 |
| Water | Balance | Balance | Balance | Balance | Balance | Balance | dosage which is effective to effectuate the desired antimicrobial effect. Appropriate amounts can be determined by those skilled in the art. Such therapeutic compositions are intended particularly for use in mammals, but use outside of mammals is contemplated. It is expected that the formulations will be used by humans in most practical applications.

The invention may be further clarified by reference to the following Examples, which serve to exemplify some of the embodiments, and not to limit the invention.

EXAMPLES

Example 1

Synthesis of Gel-Microemulsion Formulations

Materials: Captex® 300 was obtained from ABITEC Corp., Janesville, Wis. Cremophor EL® was from BASF Corp., Mount Olive, N.J. Phospholipon® 90G was purchased from American Lecithin Co., Danbury, Conn. PEG-200 was from Union Carbide Corp., Danbury, Conn. while propylene glycol was obtained from Spectrum Quality Products Inc., New Brunswick, N.J. Seaspan® and Viscarin® carrageenan were obtained from FMC Corp., Newark, Del. N-9 (IGEPAL CO-630) was a generous gift from Rhone Poulenc, Cranbury, N.J.

Gel-Microemulsion Formulation: A lipophilic sub-micron (30–80 nm) particle size microemulsion was developed using commonly used pharmaceutical excipients through systemic mapping of ternary phase diagrams (Eccleston G M, In: Swarbrick J, Boylan J C, eds. Encyclopedia of Pharmaceutical Technology, New York:Marcel Dekker, 1992:375–421.; Ritschel W A, Meth Find Exp Clin Pharmacol, 1993; 13: 205–20.). Several microemulsion compositions were screened for particle size, stability, and responses to in vitro spermicidal activity. The ingredients tested included: medium chain triglycerides, purified soya phospholipid, Pluronic® F-68, ethoxylated castor oil, propylene glycol, and polyethylene glycol. The ingredients selected included, drug solubilizers and stabilizers (Captex® 300, Cremophor EL®, Phospholipon® 90 G, propylene glycol, and PEG 200) and a preservative (sodium benzoate). Various polymeric gels were screened to produce a gel with desirable viscosity. Polymer suspensions of Seaspan® and Viscarin® carrageenan were selected as additives to the microemulsion-based system to obtain a gel with desirable viscosity with high thickening capability and compatibility with vaginal mucosa.

A submicron (30–80 nm) particle size microemulsion-based system containing the pharmacological excipients, Captex® 300, Cremophor EL®, Phospholipon® 90G, propylene glycol, PEG 200, and sodium benzoate, with high solubilizing capacity for lipophilic drugs was identified through systematic mapping of ternary phase diagrams, and lipophilic drug solubilization studies. The ternary phase diagram of the microemulsion components used for the preparation of GM-4 is shown in FIG. 1. The non-grid area represents the single phase microemulsion region. The asterisk represents the microemulsion which was used for GM-4 formulation listed in Table 5. Polymer suspensions of Seaspan® and Viscarin® carrageenan were selected as additives to the microemulsion-based system to obtain a gel of desirable viscosity with high thickening capability and compatibility with the microemulsion. These polymers did not cause precipitation or alter the microemulsion particle size. The GM-4 was found to be very stable at ambient temperature.

Particle size determination was made using Nicomp Model 380 laser diode source (Particle Sizing Systems, Santa Barbara, Calif.). Viscosity measurements were made using the Brookfield digital viscometer (Model DV-II+; Brookfield Engineering Laboratories, Spoughton, Mass.).

TABLE 5

Components of GM-4 Formulation

| Excipient | Type | Final concentration (%, by wt) |
|---|---|---|
| Captex ® 300 | Lipid | 10.8 |
| Cremophor EL ® | Surfactant | 7.6 |
| Phospholipon ® 90G | Phospholipid | 5.1 |
| Propylene Glycol | Humectant | 4.2 |
| PEG-200 | Humectant | 4.2 |
| Seaspan ® carrageenan | Natural polymer | 0.9 |
| Viscarin ® carrageenan | Natural polymer | 0.5 |
| Sodium benzoate | Preservative | 0.2 |
| Water | Diluent | 66.5 |

Example 2

Screening of Pharmaceutical Excipients of GM-4 for Spermicidal Activity Against Human Sperm Methods and Materials Computer-Assisted Spermicidal Assay: To evaluate the spermicidal activity of the pharmaceutical excipients used in the GM-4 formulation, a highly motile fraction of pooled donor sperm (n=9) was prepared by discontinuous (90–45%) gradient centrifugation using Enhance-S-Plus cell isolation medium (Conception technologies, San Diego, Calif.) and the "swim-up" method as previously described (D'Cruz O J, et al., Biol Reprod 1995;53:118–30.; D'Cruz O J, et al., Biol Reprod, 1998; 59:503–15.). All donor specimens were obtained after informed consent and in compliance with the guidelines of the Parker Hughes Institute Institutional Review Board. Highly motile fraction of sperm ($10 \times 10^6$/ml) were suspended in 1 ml of Biggers, Whitten, and Whittingam's medium (BWW) containing 25 mM HEPES (Irvine Scientific, Santa Ana, Calif.) and 0.3% BSA (fraction V; Sigma Chemical Co., St. Louis, Mo.) in the presence and absence of serial 2-fold dilutions of test substance. The ingredients evaluated were Captex® 300 (1.35%–10.8%), Cremophor EL® (0.95%–7.6%), Phospholipon® 90G (0.637%–5.1%), propylene glycol (0.52%–4.2%), PEG 200 (0.52%–4.2%), Seaspan® carrageenan (0.11%–0.9%), Viscarin® carrageenan (0.06%–0.5%), and sodium benzoate (0.025%–0.2%). After 3 h incubation at 37° C., the sperm head centroid-derived sperm motility parameters were determined using a Hamilton Thorne Research (Danvers, Mass.) Integrated Visual Optical System (IVOS), version 10 instrument, as previously described (D'Cruz O J, et al., Biol Reprod, 1998;58:1515–26.; D'Cruz O J, et al., Mol Hum Reprod, 1998;4:683–93.; D'Cruz O J, et al., Biol Reprod, 1999;60:435–44.; D'Cruz O J, et al. Biol Reprod, 1999;60:1419–28.). The attributes of sperm kinematic parameters evaluated included numbers of motile (MOT) and progressively (PRG) motile sperm; curvilinear velocity (VCL); average path velocity (VAP); straight-line velocity (VSL); beat-cross frequency (BCF); and the amplitude of lateral head displacement (ALH) and the derivatives, straightness (STR) and linearity (LIN). Data from each individual cell track were recorded and analyzed. For each aliquot sampled, >200 sperm were analyzed. The percentage motilities were compared with those of sham-treated control suspensions of motile sperm. The spermicidal activity of the test compound was expressed as $EC_{50}$ (the final concentration of the compound in the medium that decreased the proportion of motile sperm by 50%).

Results

Figure 2:
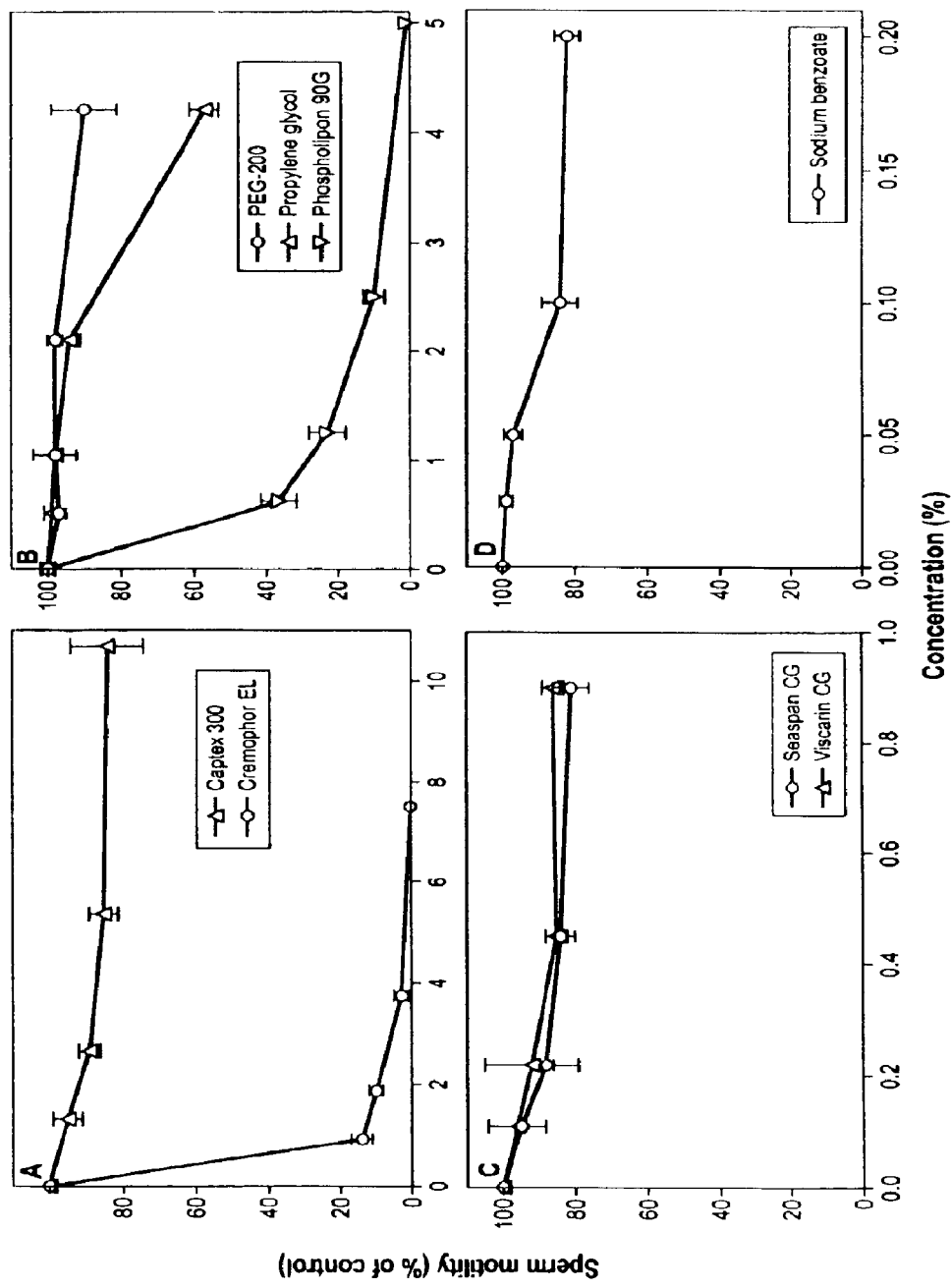
FIG. 2 shows the effect of individual components of GM-4 on the motility of washed and enriched human sperm. Highly motile fractions of sperm were incubated with increasing concentrations of listed compounds in the assay medium, and the percentage of motile sperm was evaluated by CASA. The plots show mean values of two representative measurements. Cremophor EL® and Phospholipon 90G® were spermicidal at all concentration tested. Captex® 300, PEG-200, propylene glycol, Seaspan® carrageenan, Viscarin® carrageenan, and sodium benzoate demonstrated little or no inhibition over the range of concentrations tested.

The effects of individual components of GM-4 on the motility of washed and enriched motile fraction of sperm evaluated by CASA are summarized in FIG. 2. At the final concentrations used for GM-4 formulation, Captex® 300, PEG 200, Seaspan® carrageenan, Viscarin® carrageenan, and sodium benzoate, demonstrated little or no inhibitory effects on human sperm motility. Further, sperm motion kinematics using CASA confirmed that these excipients did not significantly alter the sperm motion parameters, such as the progressive velocity, straightness of the swimming pattern, linearity of the sperm tracks, beat-cross frequency, and the amplitude of lateral sperm head displacement. In contrast, Cremophor EL® and Phospholipon®90G were spermicidal over the entire range of concentrations tested whereas propylene glycol was partially spermicidal at the highest concentration tested ($EC_{50}$=>4.2%). The concentration-dependent spermicidal activity by Cremophor EL® and Phospholipon® 90G was associated with a parallel decline in sperm kinematics, particularly with respect to track speed (VCL), path velocity (VAP), and straight line velocity (VSL).

Example 3

Spermicidal Activity of Pharmaceutical Excipients of GM-4 and of the GM-4 Formulation in Human Semen Methods and Materials The effect of duration of incubation on spermicidal activity in the presence of each of the eight pharmaceutical excipients was tested by mixing an aliquot of semen with equal volume of test compounds in BWW-0.3% BSA to yield the final concentrations contained in GM-4. At timed intervals of 15, 30, 45 and 60 min, 5 μl samples were transferred to two 20-μm Microcell (Conception Technologies) chambers, and sperm motility was assessed by CASA. Sperm motility in samples too viscous for CASA analysis (Seaspan® carrageenan, Viscarin® carrageenan, Cremophor EL® and Phospholipon® 90G) were determined by phase contrast microscopy, and the number of motile sperm per treatment were enumerated for a total of 200 sperm. The time course test was performed in 3 separate trials, with semen obtained from three different donors.

Modified Sander-Cramer Assay: The spermicidal activity of GM-4 formulation, as produced in Example 1, was tested by a modified Sander-Cramer assay (Sander F V, et al., *Hum Fertil*, 1941;6:134–7.; D'Cruz O J, et al., *Contraception*, 1999;59:319–31.). Briefly, aliquots (0.1 ml) of freshly liquefied semen were rapidly mixed with an equal volume of freshly prepared GM-4 formulation. A 5-μl sample was transferred to a 20 μm Microcell chamber (Conception Technologies) and examined immediately under a phase contrast microscope (Olympus BX-20; Olympus Corporation, Lake Success, N.Y.) attached to a CCD camera (Hitachi Deneshi Ltd., Tokyo, Japan) and a videomonitor. The time required for sperm immobilization was recorded in seconds. This test was performed in six separate trials, with semen obtained from six different donors.

Figure 3:
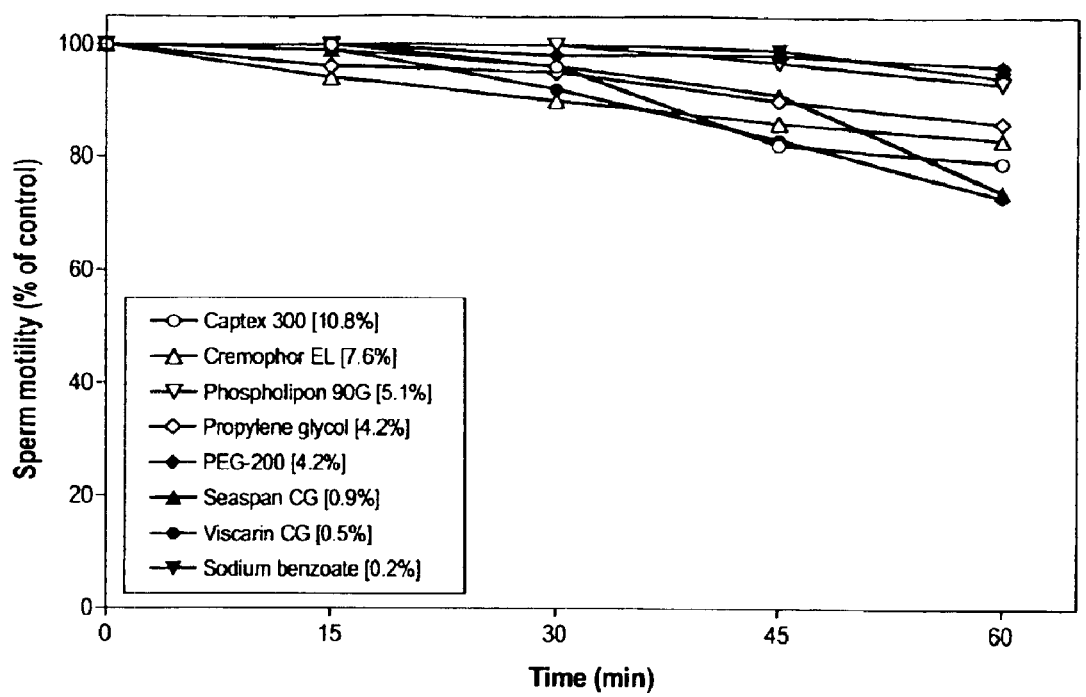
FIG. 3 shows the effect of individual components of GM-4 on the motility of human sperm in semen. Aliquots of liquefied semen were mixed with an equal volume of assay medium containing the final concentrations of components of GM-4 formulation. At timed intervals, sperm motility was evaluated. The plot shows mean values from two representative experiments. All the components of GM-4 formulation demonstrated little or no inhibition of sperm motility in human semen over the entire range of time course tested.

Results:

The results of spermicidal activity of individual components of GM-4 tested in human semen rather than using washed motile fraction of sperm are shown in FIG. 3. A time course study of sperm motility impairment by each of the individual components of GM-4 formulation revealed that none of the eight components tested including Captex® 300, Phospholipon®D 90G, Cremophor EL®, propylene glycol, PEG 200, Viscarin® carrageenan, Seaspan® carrageenan and sodium benzoate was spermicidal in human semen ($t_{1/2}$=>60 min).

By contrast, the submicron particle size GM-4 formulation completely immobilized sperm in human semen in less than 2 min (1.2±0.3 min). Thus, the combination of these pharmaceutical excipients as a gel-microemulsion formulation was a potent spermicide in semen.

Example 4

Preparation and Characterization of GM-4 Formulation Containing 2% WHI-07

WHI-07 is a phenyl phosphate derivative of bromomethoxy zidovudine (WHI-07) with potent anti-HIV and spermicidal activities. WHI-07 is a lipophilic zidovudine (AZT) derivative which has extremely low solubility in water. WHI-07 has the following chemical structure:

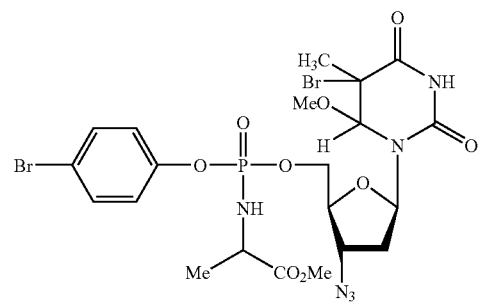

Chemical name: (5R,6R)-and (5S,6S)-5-bromo-6-methoxy-5,6-dihydro-AZT-5'-(para-bromophenyl methoxyalaninyl phosphate). Molecular weight: 698.

WHI-07 was synthesized using the following synthetic scheme.

Synthetic Scheme for WHI-07

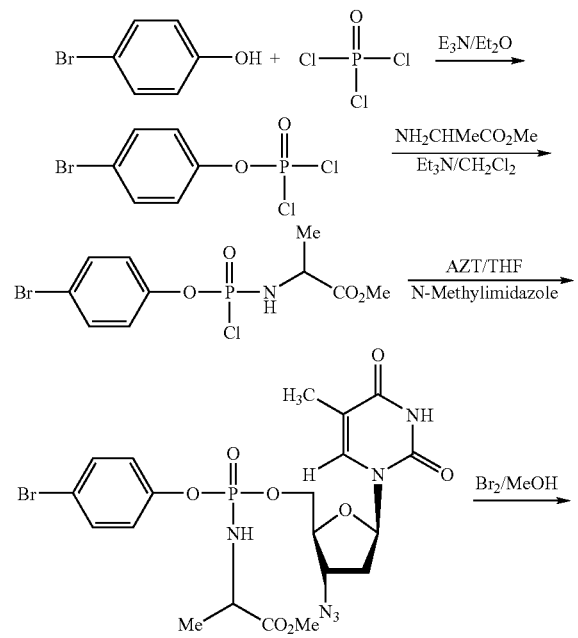

-continued

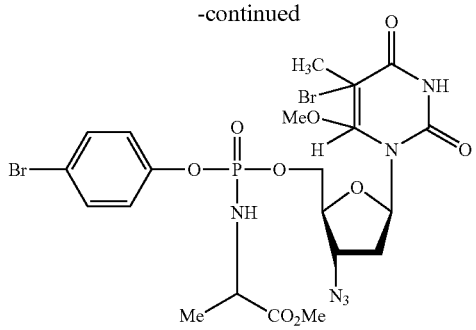

Chemical Characterization:

Melting Point: 59–60° C.; $R_f$: 0.56 (10% MeOH/90% $CHCl_3$); UV (MeOH) 209, 218, 221, & 261 nm; IR (Neat): 3218, 3093, 2925, 2850, 2105, 1712, 1484, 1378, 1241, 1153, 1010, 929 $cm^{-1}$.

$^1$H NMR ($CDCl_3$) d 8.66 (1H, br, 3-NH), 7.43 (2H, d, J=9.0 Hz, Aryl H), 7.14 (2H, d, J=9.0 Hz, Aryl H), 6.01 (0.68H, t, J=6.3 Hz, —CH at C-1'), 5.37 (0.32H, m, —CH at C-1'), 4.87 (0.68H, s, —CH at C-6), 4.61 (0.33H, s, —CH at C-6), 4.35–3.96 (6H, m, —CH at C-3', 4', 5'and Ala-NH, a—CH), 3.74 (3H, s, —$COOCH_3$), 3.44 (3H, s, —$OCH_3$ at C-6), 2.56–2.30 (2H, m, —$CH_2$ at C-2'), 1.93 (3H, s, —$CH_3$ at C-5), 1.38 (3H, m, a—$CH_3$ of Ala).; $^{13}$C NMR ($CDCL_3$) d 173.6, 166.7, 150.1, 148.9, 132.7, 132.5, 121.9, 121.7, 118.1, 87.7, 85.1, 81.7, 81.5, 81.4, 65.7, 65.6, 60.0, 57.9, 57.8, 53.6, 52.7, 50.3, 50.2, 36.9, 36.7, 22.8, 22.7, 21.2, 21.1.; $^{31}$P NMR ($CDCl_3$) d 2.70, 2.60, 2.54, 2.32.; MS (CI, m/e) 700.6 ($M^+$, $^{81}Br+^{81}Br$), 698.6 ($M^+$, $^{81}Br+^{79}Br$), 696.6 ($M^+$, $^{79}Br+^{79}Br$), 588.8 ($M^+$—Br—$OCH_3$, $^{81}Br$), 586.9 ($M^+$—Br—$OCH_3$, $^{79}Br$).; HPLC: 39.06, 40.28, 45.33, & 49.25 min (Column: LiChrospher 100 RP-18e (5 μm); Flow rate: 1 mL/min; Solvent: $H_2O$ (0.1% TEA+0.1% TFA): $CH_3CN$=62:38).

Appearance: White solid at room temperature; Solubility: <0.003% solubility in water, soluble in oil (medium chain triglyceride, 4.1%), and quite soluble in some hydrophilic cosolvents such as polyethylene glycol 300 (13.1%). It is also soluble in several organic solvents including chloroform, ethanol, methanol, and DMSO.; Octanol/Water partition coefficient: Log $K_D$=2.05 (see below)

Partition coefficient of WHI-07: Four samples of WHI-07, 51.8 mg, 64.6 mg, 56.5 mg, and 74.5 mg were weighed and dissolved in 5 ml of octanol in four test tubes. After the drug was completely dissolved in octanol, 5 ml of water was added to each octanol solution. The mixtures were handshaken vigorously for 10 min, and afterward let to stand overnight until a complete phase separation occurred.

Samples of water and octanol were taken from each mixture, and directly injected into the HPLC for analysis. Peak areas of WHI-07 in the water layer and in corresponding octanol layer are shown in Table 6. The peak area ratios represent the partition coefficient.

TABLE 6

| Sample | Octanol layer Peak area (mAU*s) | Water layer Peak area (mAU*s) | Peak area ratio Octanol/water |
|---|---|---|---|
| 1 | 5324.3 | 46.74 | 113.9 |
| 2 | 6159.2 | 55.32 | 111.3 |
| 3 | 5712.4 | 49.32 | 115.8 |
| 4 | 7347.4 | 67.25 | 109.2 |

The average octanol/water partition coefficient is: Log $K_D$ = 2.05

The suitable microemulsion compositions were identified by first constructing a series of ternary phase diagrams. The solubilizations of WHI-07 in several microemulsions selected from within the single phase microemulsion region in the phase diagrams were determined to identify microemulsions with high solubilizations of WHI-07.

Solubility of WHI-07

The solubility of WHI-07 in Captex® 300 and polyethylene glycol 300 was carried out using UV-Vis spectrophotometer at 272 nm.

Calibration curve: Two stock solutions of WHI-07 were prepared in ethanol at concentrations of 4.2 mg/ml and 3.85 mg/ml respectively. These stock solutions were diluted in ethanol to prepare the standard solutions with concentrations and $A_{272}$ shown in Table 7. The plot of the calibration curve is shown in Curve 1.

TABLE 7

| Calibration sample | Conc. in mg/ml | $A_{272}$ |
|---|---|---|
| 1 | 0.06 | 0.07 |
| 2 | 0.12 | 0.128 |
| 3 | 0.24 | 0.240 |
| 4 | 0.48 | 0.467 |
| 5 | 0.96 | 0.927 |
| 6 | 1.93 | 1.802 |
| 7 | 0.11 | 0.084 |
| 8 | 0.21 | 0.182 |
| 9 | 0.42 | 0.414 |
| 10 | 0.53 | 0.479 |
| 11 | 0.7 | 0.652 |
| 12 | 1.05 | 0.969 |
| 13 | 2.10 | 1.886 |

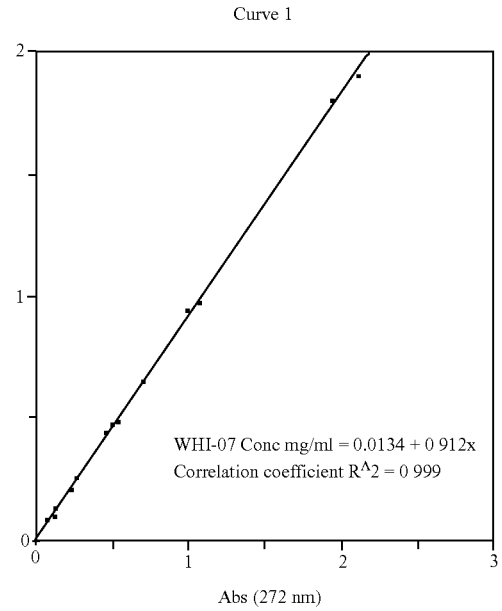

Curve 1

Sample Preparation and Assay

Appropriate amounts of WHI-07 and Captex® 300 or PEG300 were weighed and placed in glass containers. Each sample was stirred with a stir bar at ambient temperature for 2 hours. Each sample was then filtered through 0.45 μm filter, and diluted with ethanol for UV-Vis measurement. The results are shown in Table 8.

TABLE 8

| | WHI-07 Solubility (mg/ml) |
|---|---|
| Captex ® 300 | 40.6 +/− 4.1 (n = 3) |
| PEG300 | 131.5 +/− 4.9 (n = 3) |

Polymer suspensions were added to the microemulsions to increase their viscosity. Two types of polymers, xanthan gum and Carrageenan, were found to be particularly suitable but other types of polymers can also be used to produce gel-microemulsions. In general, a total polymer concentration of about between 0.5% and 3% is needed to provide a gel-microemulsion with adequate viscosity.

Based on these results, we postulated that WHI-07 can be delivered using the GM-4 formulation. To this end, 18.7 mg of WHI-07 was first dissolved in 305 mg of a microemulsion consisting 32.4% of Captex® 300 (medium chain triglyceride), 4.3% of purified water, and 63.3% of surfactant-cosolvent mixture containing 36% of Cremophor EL®, 24% of Phospholipon® 90G (purified soya lecithin), 20% of polyethylene glycol 200 and 20% of propylene glycol all by weight. The mixture was heated to 70° C. The drug was completely dissolved in the mixture after about 5 minutes of mixing with a stir bar. The drug solution was then removed from the heat. The resulting composition was a clear microemulsion.

This WHI-07-containing microemulsion concentrate was diluted with water to bring the intensity to between 300 and 500 KHZ for optimal particle size measurement. The particle diameter of the microemulsion in the absence of polymers was determined by laser light scattering using Nicomp 380 Submicron Particle Sizer (Particle Sizing Systems, Inc., Santa Barbara, Calif.). The size distribution and mean particle diameter value became stabilized quickly after a few minutes of run time. A average (mean±SD) particle diameter of 18.5±8.1 nm was determined by Nicomp 380 photon correlation light scattering particle sizer.

WHI-07 Concentration Analysis in WHI-07 Formulations

Routine analysis of WHI-07 were performed by dissolving the samples in ethanol or acetonitrile and analyzed with HPLC after appropriate dilution. WHI-07 gel formulations, however, are not totally soluble in either ethanol or acetonitrile because of the polymers in the formulation. The following WHI-07 analytical methods were developed for the gel formulations. The accuracy and precision of the methods meet pharmaceutical requirements.

WHI-07 calibration curve 101.3 mg of WHI-07 (96% purity) was dissolved in a 10 ml glass vial with 1.5 ml of a microemulsion with the following composition: 36% Cremophor EL®, 24% Phospholipon® 90G, 20% PEG 200, and 20% propylene glycol. The mixture was stirred for 10 min at 50° C. until the drug was completely dissolved and the mixture was clear. The vial was removed from the hot plate and 3.5 ml of the polymer suspension (1.3% Seaspen Carrageenan, 0.7% Xantural™, and 0.3% sodium benzoate in DI water) was added to the vial. The vial was hand shaken for 1 min and vortexed for 1 min or until the mixture was homogeneous.

The control (drug-free) gel microemulsion was prepared by mixing 1.2 ml of the microemulsion with 2.8 ml of the polymer suspension. The calibration curve was prepared as following:

Five standard solutions with varying WHI-07 contents were prepared as shown in Table 9. Each vial was hand shaken and the polymers in the gel was precipitated out. The mixture was then centrifuged at room temperature for 10 min at 2000 rpm. The vials were carefully removed from the centrifuge and 0.5 ml of the supernatant was pipetted out from each vial for HPLC analysis.

The condition for HPLC analysis (WHI-07) was as follows:
Column: RP18e (5 μm) Lot #L228433
Eluent: Acetonitrile/(0.1% TFA and 0.1% TEF)=45/55
Eluent flowrate: 1 ml/min
Sample injection volume: 20 μl
Method run time: 30 min Under these conditions, the retention times for the three isomeric peaks of WHI-07 were 20.5 min, 23.2 min, and 24.9 min. The area ratio of these peaks were 31.9:5.7:3.3. The peak with retention time of 20.5 min was used to construct the calibration curve by plotting WHI-07 concentration vs. peak area. The calibration curve was linear in the WHI-07 concentration range of 0 to 1.3 mg/ml with a correlation coefficient of 1.000 (Curve 2).

TABLE 9

| Vial # | WHI-07 gel added (ml) (20.26 mg/ml) | Control gel added (ml) | ACN added (ml) | WHI-07 concentration (mg/ml) | Peak(20 min) (mAU*s) |
|---|---|---|---|---|---|
| 1 | 0 | 0.50 | 4.0 | 0 | 0 |
| 2 | 0.05 | 0.45 | 4.0 | 0.225 | 1121.2 |
| 3 | 0.10 | 0.40 | 4.0 | 0.450 | 2348.4 |
| 4 | 0.20 | 0.30 | 4.0 | 0.900 | 4682.6 |
| 5 | 0.30 | 0.20 | 4.0 | 1.351 | 6998.1 |

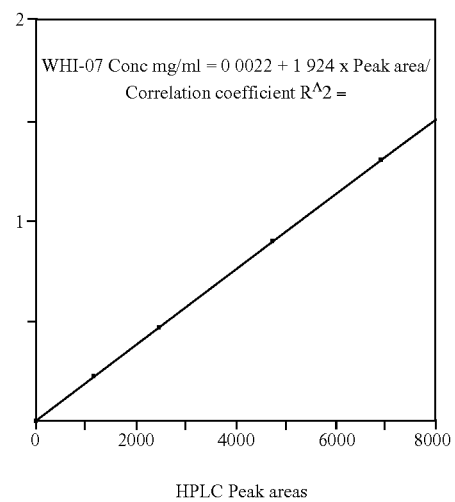

Curve 2: Calibration curve for WHI-07 gel formulation

Precision of the Analytical Method

To test the precision of the method, ten WHI-07 gel samples were prepared as following, and HPLC analysis was performed. 101.3 mg of WHI-07 (99.4% purity) was solved in a 10 ml glass vial with 1.5 of the microemulsion with composition of 36% mophor EL®, 24% Phospholipon® 90G, 20% PEG 200 and 20% propylene glycol. The mixture was stirred for 10 min at 50° C. until the drug was dissolved and the mixture was clear. The vial was removed from the hot plate and 3.5 ml of the polymer suspension (1.3% Seaspen Carrageenan, 0.7% Xantrual and 0.3% sodium benzoate in DI water) was added to the vial. The vial was hand shaken for 1 min and vortexed for 1 min or until the mixture was homogeneous.

The control gel was prepared by mixing 1.2 ml of the microemulsion with 2.8 ml of the polymer suspension. To each of the 10 vials, 0.2 ml of the WHI-07 gel, 0.3 ml of the control gel and 4 ml of acetonitrile were added. The vials were then handshaken for 1 min and vortexed for 1 min. The mixture was then centrifuged at room temperature for 10 min at 2000 rpm. The vials were carefully removed from the centrifuge and 0.5 ml of the supernatant was pipetted out from each vial for HPLC analysis. The data was analyzed to determine the precision of the method. The results are shown in Table 10. The relative standard deviation of the method was 0.61%. These data indicate that the developed method has a good precision for the analysis of WHI-07 content in the gel formulation.

TABLE 10

| Vial # | Peak area(mAU*s) | deviation | relative standard deviation (RSD) |
|---|---|---|---|
| 1 | 2312.8 | 18.04 | |
| 2 | 2285.2 | −7.56 | |
| 3 | 2272.0 | −22.76 | |
| 4 | 2279.4 | −15.36 | |
| 5 | 2296.0 | 1.24 | |
| 6 | 2275.6 | −19.16 | |
| 7 | 2299.4 | 4.64 | |
| 8 | 2291.2 | −3.56 | |
| 9 | 2332.8 | 38.04 | |
| 10 | 2303.2 | 8.44 | |
| Average | 2294.76 | 14.08 | 0.61% |

Procedures for WHI-07 Formulation Sample Preparation:

240 mg of WHI-07 was weighed in a 10 ml glass shell vial. 4.0 ml of the microemulsion was transferred to the vial with a 1.0 ml Drummond pipette. A 12×4 mm magnetic stir bar was placed in the vial and the vial was placed on the Corning stir/hot plate for mixing. The dials for both stir and heat were set at #3. The mixture was heated for 5 min until the drug crystals were disappeared and the mixture was clear. WHI-07 concentration in this microemulsion was 60 mg/ml.

2% WHI-07 gel was prepared by mixing 2 ml of the concentrated WHI-07 microemulsion with 4 ml of the polymer suspension in a 10 ml glass shell vial. 1 % WHI-07 gel was prepared by mixing 1 ml of the concentrated WHI-07 microemulsion with 1 ml of the microemulsion and 4 ml of the polymer suspension. 0.5% WHI-07 gel was prepared by mixing 0.5 ml of the concentrated WHI-07 microemulsion with 1.5 ml of the microemulsion and 4 ml of the polymer suspension. The control gel was prepared by mixing 2 ml of the microemulsion and 4 ml of the polymer suspension.

WHI-07formulation concentration analysis: Two samples, 100 μl each, were taken from each preparation for concentration analysis. The samples were placed in 5 ml glass shell vials. 4.2 ml of acetonitrile was added to each of the sample vials. The vials were hand shaken for 10 seconds and were placed in a shaker at 200 rpm for 30 min. The vials were hand shaken again for 10 seconds and span for 10 min at 2000 rpm in the Beckman GS-6 Centrifuge. The vials were carefully removed from the centrifuge and 1 ml each of the supernatant was pipette out for HPLC analysis. The results were shown in Table 11. All of the samples meet pharmaceutical requirement (RSD less than 5.0%).

TABLE 11

| Vial # | Sample ID | WHI-07 concentration | Average | RSD |
|---|---|---|---|---|
| 1 | 0.5% WHI-07 | 0.52% | | |
| 2 | 0.5% WHI-07 | 0.49% | 0.5% | 0 |
| 3 | 1.0% WHI-07 | 1.02% | | |
| 4 | 1.0% WHI-07 | 0.92% | 0.97% | 3.0% |
| 5 | 2.0% WHI-07 | 1.88% | | |
| 6 | 2.0% WHI-07 | 1.99% | 1.94 | 3.0% |

We next examined the shelf life/stability of the WHI-07. A gel-microemulsion with WHI-07 concentration of 0.5% and 2.0% were prepared and were analyzed for WHI-07 concentrations at day 1, day 4 and day 8. The result is shown in the following Table 12:

TABLE 12

| Time (day) | 0.5% WHI-07 gel microemulsion | 2.0% WHI-07 gel microemulsion |
|---|---|---|
| 1 | 0.5 | 2.0 |
| 4 | 0.49 | 2.0 |
| 8 | 0.51 | 1.97 |
| Percent change at day 8 | 2% | 1.5% |

The result indicates that WHI-07 was stable in the gel microemulsion formulations were stable at room temperature in the 8 day observations.

Formation of gel-microemulsion: This drug-containing microemulsion was then mixed with 600 mg of a polymer suspension containing 1.3% of Seaspan® Carrageenan, 1.3% of Viscarin® Carrageenan, and 0.3% of sodium benzoate by weight with gentle mixing. The resulting gel microemulsion had a pH of 7.2 and was a translucent gel with the following composition:

| | % (by weight) |
|---|---|
| WHI-07 | 2.0 |
| Captex ® 300 | 10.7 |
| Phospholipon ® 90G | 5.0 |
| Cremophor EL ® | 7.5 |
| Propylene glycol | 4.2 |
| PEG 200 | 4.2 |
| Seaspan ® Carrageenan | 0.9 |
| Viscarin ® Carrageenan | 0.9 |
| Sodium benzoate | 0.2 |
| Water | 64.4 |

The viscosity of the GM-4 formulation with and without WHI-07 was determined using a Brookfield DV-E Viscometer with spindle #3 (speed: 10 rpm). Drug-free GM-4 formulation had a viscosity of 301.9 centripoises. The GM-4 formulation containing 2% WHI-07 had a viscosity of 64.7.

Although a viscosity of 64.7 appeared to be sufficient for the utility of the 2% WHI-07 containing GM-4 formulation to prevent transvaginal or transrectal transmission of FIV, the viscosity could easily be increased by using a different polymer suspension. For example, a thicker formulation was prepared as follows: This drug-containing microemulsion in Example was mixed with 600 mg of a polymer suspension containing 1.3% of Seaspan® Carrageenan, 0.7% of Xantural™, and 0.3% of sodium benzoate by weight with gentle mixing. The resulting gel microemulsion was a translucent gel-like liquid with the following composition:

| | % (by weight) |
|---|---|
| WHI-07 | 2.0 |
| Captex ® 300 | 10.7 |
| Phospholipon ® 90G | 5.0 |
| Cremophor EL ® | 7.5 |
| Propylene glycol | 4.2 |
| PEG 200 | 4.2 |
| Seaspan ® Carrageenan | 0.9 |
| Xantural ™ | 0.5 |
| Sodium benzoate | 0.2 |
| Water | 64.8 |

The viscosity of this formulation was 380 centripoises. This formulation was also found to have good colloidal stability when stored at room temperature for several months.

Example 5

Preclinical Studies

Methods and Materials

Rabbits: Fifty nine female and 12 male, sexually mature (>6 months old; >7 lbs), specific-pathogen-free, New Zealand White rabbits were obtained from Charles River Laboratories (Wilmington, Del.). For each fertility trial, 24 does and 12 bucks were used. All rabbits were uniquely identified with metal ear tags. Tap water and rabbit food pellets (Teklad LM-485; Harlan Teklad) were available ad libitum. The does and bucks were maintained in separate rooms that were kept at 22±2° C. with relative humidity of 50±20% and a 12-h fluorescence light cycle. The rabbits were isolated for a minimum of 4 weeks before the fertility trials. All procedures were approved by the Parker Hughes Institute Animal Use and Care Committee. All animal husbandry operations were conducted under current USDA Guidelines.

Mice: Twenty, female $B_6C_3F_1$ mice of approximately 6 weeks of age were obtained from Charles River Laboratories (Wilmington, Del.) and were uniquely identified with metal ear tags and ear notches. Tap water and laboratory diet (Teklad LM-485; Harlan Teklad) were available ad libitum. The animals were maintained in a room that was kept at 22±2° C. with relative humidity of 50±10% and a 12-h fluorescence light cycle. All animal husbandry operations were conducted under NIH 1996 Guidelines.

In Vivo Contraceptive Efficacy in the Rabbit Model: For each fertility trial, 24 does and 12 bucks were used. For each contraceptive test, the does were divided into 3 subgroups of 8; 1) control does; 2) GM-4 group and; 3) N-9 group. Semen was obtained from bucks (n=12) of proven fertility via a prewarmed (45° C.) artificial vagina immediately before use. Sperm count and motility was assessed to ensure that the males were ejaculating good quality semen. Prior to artificial insemination, semen samples without the contamination of urine or gel were pooled and 0.5 ml (>30×10$^7$ sperm/ml) aliquots were transferred to 1 ml tuberculin syringes. Two ml of a GM-4 formulation or a commercial 2% N-9 formulation (Gynol II; Ortho Pharmaceutical Corp., Raritan, N.J.) was applied intravaginally by means of a 3 ml disposable plastic syringe. The doe was held in a supine position during the application of 2 ml of the test agent followed by the application of semen dose (0.5 ml) which was deposited within 1–2 min by inserting approximately 8 cm of the syringe into the vagina for the delivery of the test agent. At the time of artificial insemination, ovulation was induced by an intravenous injection of 100 IU of human chorionic gonadotropin (Sigma Chemical Co., St. Louis, Mo.) into the marginal ear vein. After ovulation and artificial insemination, the does were allowed to complete their pregnancy (31±2 days). Pregnant does were transferred to cages containing nest boxes (16×12×6 in). The litter size, weight, fetal length, and the condition of each offspring at birth were recorded. The in vivo spermicidal effect of GM-4 formulation versus 2% N-9 formulation was assessed based on the level of pregnancy reduction achieved in comparison to controls and the consistency of this response. The vaginal delivery/artificial insemination and pregnancy cycle was repeated a second time.

Rabbit Vaginal Irritation Test: For the vaginal irritation study, eleven female rabbits were treated intravaginally with 1 ml of GM-4 (seven rabbits) or 1 ml of GM-4-containing 4% N-9 (four rabbits), for 10 consecutive days. Animals were sacrificed on day 11 and the reproductive tract was examined grossly and microscopically after completion of the study (Eckstein P, et al., *J Reprod Fertil*, 1969;20:85–93.). The vaginal tissues were rapidly removed and parts of the caudal, mid, and distal regions of each vagina were fixed in 10% buffered formalin. Tissues were embedded in paraffin, sectioned at 4–6 μm and stained with hematoxylin and eosin and examined under ×200 and ×400 magnification using a Leica light microscope (Milton Keynes, Buckinghamshire, UK) interfaced with an image analysis system. The images were captured using the ImagePro Plus program (Media Cybernetics, Silver Spring, Md.) in conjunction with a 3CCD camera (DAGE-MTI Inc., Michigan City, Kans.), and images were transferred to Adobe Photoshop 5.5 software (Adobe Systems Inc., San Jose, Calif.) for observation and analysis. Each of the three regions of vagina were examined for epithelial ulceration, edema, leukocyte infiltration, and vascular congestion. The scores were assigned based on the scoring system of Eckstein et al., (Eckstein P, et al., *J Reprod Fertil*, 1969;20:85–93.) which was as follows: Individual score: 0=none, 1=minimal, 2=mild, 3=moderate, 4=intense irritation; Total score: <8 acceptable, 9–10 marginal, and ≧11 unacceptable. Results were expressed as the mean ±SD values.

Thirteen-Week Toxicity Study in Mice: Twenty, female $B_6C_3F_1$ mice were allocated to two groups. The test group of 10 mice received 50 μl of the GM-4 formulation intravaginally for 5 days per week for 13 consecutive weeks. Ten mice without intravaginal treatment served as the control group. The GM-4 formulation was prepared weekly and the intravaginal treatment was performed inside a microisolator. All animals were individually observed daily for signs of toxic effects. Body weights were obtained before exposure (day 0), weekly during exposure, and preceding sacrifice. At the end of the study, animals were sacrificed for pathologic and histopathologic examinations and determination of blood chemistry. Hematological analyses were performed from blood obtained from 5 control and 5 test mice.

Hematology Parameters: Complete blood counts and differentials were obtained using an Abbot CELL-DYN 3200 multiparameter, automated hematology analyzer (Abbot Laboratories, Abbot Park, Ill.) which was standardized for mouse blood. This instrument uses flow cytometric techniques to provide the hemograms for anticoagulated whole blood samples: red blood cell count (RBC; $10^6$/μl), total and differential leukocyte count (lymphocytes [LYM], neutrophils [NEU], monocytes [MONO], eosinophils [EOS], and basophils [BASO] as $10^3$/μl or %), hemoglobin concentration (HGB; g/dl), hematocrit (HCT; %), mean corpuscular volume (MCV; fl), mean cell hemoglobin content (MCH; pg), mean cell hemoglobin concentration (MCHC; g/dl), red cell distribution width (RDW; %), platelet count (PLT; $10^3$/μl), and mean platelet volume (MPV; fl).

Clinical Chemistry Profiles: Biochemical analyses were performed using a Beckman SYNCHRON CX5CE random access analyzer (Beckman Coulter Inc., Fullerton, Calif.). After 13 weeks of intravaginal application of GM-4, blood was obtained from GM-treated and control mice in lithium heparin tubes and the clarified plasma was used for the determination of serum/plasma levels of total protein (TP), albumin/globulin (ALB/G), blood urea nitrogen (BUN), creatinine (CRE), total cholesterol (CHO), triglycerides (TG), aspartate aminotransferase (AST), alanine aminotransferase (ALT), amylase (AMY), total bilirubin (TBIL), glucose (GLU), and calcium (Ca), phosphorous (P), sodium (Na), potassium (K), and chloride (Cl) using reagents and methods provided by the manufacturer.

Necropsy and Histopathology: Mice were killed after 13 weeks of intravaginal exposure of GM-4 for complete necropsy evaluations. The thymus, lungs, heart, liver, pancreas, spleen, kidneys, reproductive organs (ovaries, uteri and vaginal tissue) and brain from each of 10 mice were weighed at necropsy. Organ weights were recorded as absolute weights and as a percentage of body weight. The above mentioned organs and the bone and bone marrow, large and small intestine, skeletal muscle, skin, spinal cord, and urinary bladder were fixed in 10% buffered formalin solution, trimmed, embedded in paraffin, sectioned at 4–6 µm, and stained with hematoxylin and eosin. Complete histopathological examination of all tissues was performed on mice from the control and GM-4 group.

Statistical Analysis: Group means and standard deviations were calculated from initial and terminal body weights, organ weights, hematology and clinical chemistry parameters. Statistical significance of the differences between the treated group mean versus the control group was analyzed by a one-way analysis of variance, followed by Dunnett's multiple comparison test using GraphPad Prism software (San Diego, Calif.). The significance of differences in fertility between the groups was analyzed by Fisher's exact test. Differences were considered statistically significant if $p<0.05$.

Cat Studies: FeT-J cell line is a feline T-cell line chronically infected with the FIV strain Bangston ($FIV_{Bang}$). Cats were challenged with FIV by inoculating $7 \times 10^6$ infected FeT-J cells mixed in 0.2 mL of infected culture fluid in the vagina or in the rectum 1 min after insertion of 0.4 mL of the WHI-07 gel formulation. The FIV load in the peripheral blood mononuclear cells (PBMC), lymph node (LN) cells, and bone marrow (BM) cells was measured by quantitative virus isolation and PCR analysis, as previously described (Rey M A et al., Biochem Biophys. Res. Commun. 1984, 121:126–33; Diehl L J et al., J Virol 1995, 69:2328–32; Greene W K et al., Arch Virol 1993, 133:51–62; Okada S et al., AIDS Res Hum Retroviruses 1994, 10:1739–46; Tellier M C et al., Vet Microbiol 1997, 57:1–11). The cells from treated and untreated cats ($5 \times 10^6$ cells/culture) were cocultured for 3 weeks with $5 \times 10^6$ T-cell enriched PBMCs from specific pathogen-free (SPF) cats in a total volume of 5 ml in a 25 $cm^2$ flask. Culture supernatants were harvested and cells were resuspended in fresh culture media every 3 days. Viral production was determined by measuring the levels of RT activities in the culture supernatants and examining the cells for proviral DNA by FIV gag-specific and env-specific PCR at the termination of cultures (Diehl L J et al., J Virol 1995, 69:2328–32; Greene W K et al., Arch Virol 1993, 133:51–62; Okada S et al., AIDS Res Hum Retroviruses 1994, 10:1739–46). Serum samples were also examined by standard Western blot analysis for the presence of FIV core antigen p25. Cats were considered FIV positive if one of the following criteria was met during the 18-week observation period: (1) Serum samples from two different bleeding dates were positive by Western blot analysis; (2) A single Western blot result and a single virus isolation test from a different bleeding date were positive, with or without a positive PCR test; (3) PBMC, lymph node or bone marrow cells from two different bleeding dates were positive by virus isolation test; or (4) mononuclear cells from two different bleeding dates were positive by PCR with the same tissue source.

Results

In Vivo Contraceptive Activity of GM-4 versus N-9 Formulation in the Rabbit Model: Because of the rapid spermicidal activity of GM-4 formulation, we performed in vivo contraceptive efficacy studies of GM-4 formulation in the standard rabbit model. Gynol II, a commercial contraceptive containing 2% N-9, was tested in the same way for comparison. Ovulated NZW rabbits were given intravaginal application of GM-4 formulation or N-9 formulation immediately prior (<2 min) to artificial insemination with fresh pooled semen and the females were allowed to complete their pregnancy. The efficacy of GM-4 formulation versus Gynol II for preventing pregnancy in the rabbit model are summarized in Table 13. In the control group, 15 out of 16 (93.7%) rabbits artificially inseminated became pregnant and delivered a total of 123 newborn rabbits. By contrast, none of the 16 rabbits given GM-4 formulation prior to artificial insemination became pregnant ($p<0.0001$, Fisher's exact test). Whereas rabbits given Gynol II, 5 out of 16 (31.2%) rabbits became pregnant ($p=0.0006$) and delivered a total of 34 newborn rabbits. Thus, the GM-4 formulation was far more effective than Gynol II as a vaginal spermicidal contraceptive (100% vs 68.7%, $p<0.05$, Fisher's exact test).

TABLE 13

Fertility of female rabbits after artificial insemination/ovulation induction with and without intravaginal application of GM-4 formulation or Gynol II containing 2% N-9

| Treatment | No. of does inseminated | No. of does fertile (%) | Litter size |
|---|---|---|---|
| None | 16 | 15 (93.7) | 123 |
| GM-4 | 16 | 0 (0)* | 0 |
| Gynol II (2%-N-9) | 16 | 5 (31.2)† | 34 |

Aliquots (0.5 ml) of fresh, pooled semen obtained from fertile bucks (n = 12) were used to artificially inseminate the does within 1–2 min following intravaginal application of 2 ml of GM-4 or N-9 formulation. Does were induced to ovulate by an intravenous injection of 100 IU of hCG and allowed to complete term pregnancy.
Significantly different from control by Fisher's exact test, ($p < 0.0001$)
†Sigificantly different from control by Fisher's exact test, ($p = 0.0006$)

Figure 4:
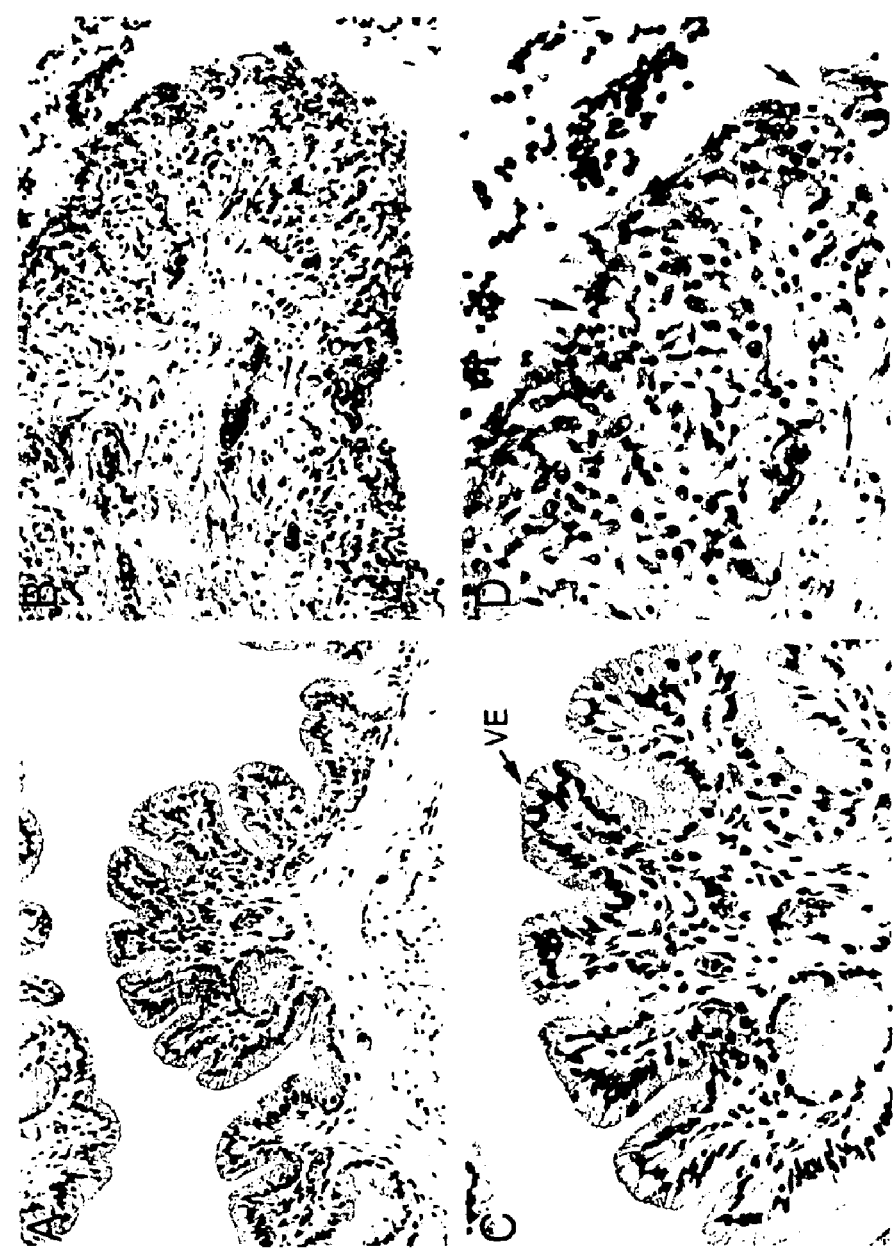
FIG. 4 is light microscopic images of GM-4 and N-9 (4%)-treated rabbit vaginal sections. Representative hematoxylin- and eosin-stained, paraffin-embedded sections of the mid vaginal region of a rabbit treated intravaginally with GM-4 formulation (Left panels, A and C) or 4% N-9 in GM-4 (Right panels, B and D) for 10 consecutive days (×200). Higher magnification (×400) shows the intactness of vaginal epithelium (VE) in a GM-4-treated rabbit (C) versus an N-9-treated rabbit (D) which shows epithelial cell layer disruption (arrows) and leukocyte influx characteristic of inflammation.

Lack of Vaginal Irritation from GM-4 in the Rabbit Model: Histological evaluation of three different regions of the vaginal tissue after daily intravaginal application of GM-4 for 10 consecutive days showed lack of significant vaginal irritation in all seven rabbits examined (mean individual scores 0–1; total score 2, range 0–3) [Table 14]. In contrast, all rabbits treated with 4% N-9 had epithelial ulceration, edema, leukocyte influx, and vascular congestion characteristic of inflammation (mean individual scores 1–3; total score 9, range 7 to 11) as quantitated by histological scoring according to the method of Eckstein et al (Eckstein P, et al., *J Reprod Fertil,* 1969; 20:85–93.). FIG. 4 shows the representative vaginal section from a GM-4-treated rabbit which showed intact vaginal epithelium when compared with the vaginal section of a N-9-treated rabbit which revealed disruption of the epithelial lining, and an inflammatory response with influx of leukocytes, consistent with previously published observations in rats (Tryphonas L, et al., *Toxicol Lett,* 1984;20:289–95.).

TABLE 14

Scoring of histological changes in the rabbit vaginal tissue after 10 days of intravaginal application of GM-4 formulation with and without 4% N-9

|  | GM-4 (n = 7) | GM-4 + 4% N-9 (n = 4) |
|---|---|---|
| Epithelial ulceration | 0* | 3 ± 2*†‡ |
| Lamina propria thickness | 1 ± 1 | 2 ± 1 |
| Leukocyte Infiltration | 1 ± 1 | 3 ± 2 |
| Vascular congestion | 0 | 1 ± 1 |
| Total score | 2 ± 1† | 9 ± 2 |

*Seven rabbits were administered intravaginally with 1 ml of GM-4 and 4 rabbits were exposed to GM-4 containing 4% N-9.
†Mean ± SD values representing the caudal, middle, and distal sections of vagina from each rabbit.
‡Semiquantitative scoring based on Eckstein et al (J Reprod Fertil, 1969; 20: 85–93.) Individual score: 0 = none, 1 = minimal, 2 = mild, 3 = moderate, 4 = intense. Total score: <8 acceptable, 9–10 marginal, and ≧11 unacceptable.

Figure 5:
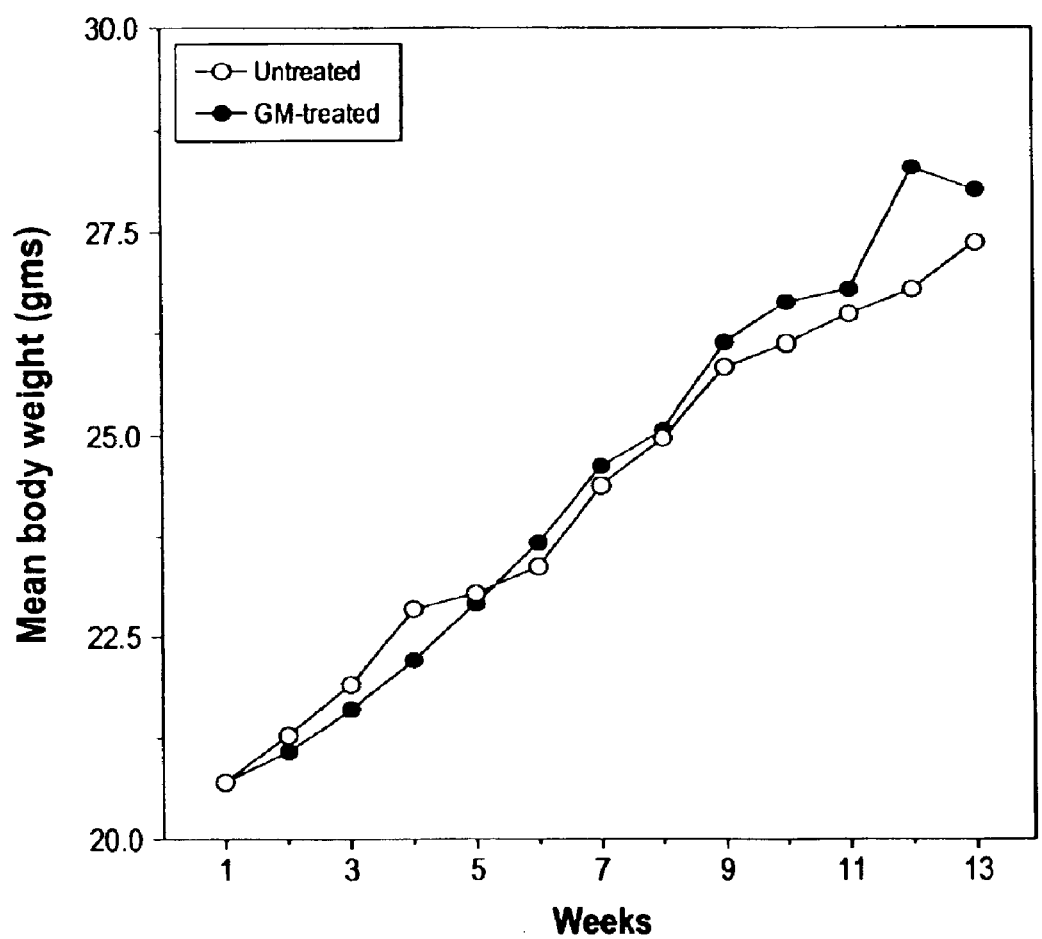
FIG. 5 shows the mean body weights of 10 female $B_6C_3F_1$ mice with and without intravaginal application of GM-4, 5 days/week for 13 consecutive weeks.

Lack of Systemic Toxicity from GM-4 in Mice: Female $B_6C_3F_1$ mice (n=10) were treated with intravaginal application of GM-4, 5 days per week, for 13 consecutive weeks. Mortality did not occur and there were no clinical signs attributed to intravaginal exposure of GM-4 throughout these studies. All animals were clinically healthy at the end of the study. Mean body weight gain and final mean body weight of control mice (27.4±1.6 g; n=10) and test mice (28.0±3.0 g; n=10) exposed to GM-4 formulation were similar (FIG. 5).

Complete blood counts of mice revealed no biologically significant differences between GM-4-treated and control mice. The values of hematologic parameters for red cell, leukocyte, lymphocyte, platelet counts, and hemoglobin were within normal limits (Table 15). Analysis of blood chemistry parameters for female mice revealed no significant treatment-related differences between GM-4-treated and control groups (Table 16). The kidney function (BUN and CRE), liver function (TBIL, AST, ALT, ALB/G, GLU, and TG), pancreas function (AMY and GLU), and nutritional status (TP), were not affected adversely by repeated intravaginal exposure to GM-4 formulation.

TABLE 15

Hematological Findings for $B_6C_3F_1$ Mice Given GM-4 Intravaginally for 13 Weeks

| Parameter | Control | GM-4 |
|---|---|---|
| RBC (× $10^4$/μl) | 949 ± 62* | 905 ± 61* |
| WBC (× $10^4$/μl) | 2.6 ± 1.2 | 2.0 ± 0.7 |
| LYM (%) | 76.3 ± 17.7 | 85.4 ± 5.6 |
| NEU (%) | 3.0 ± 1.2 | 2.5 ± 0.8 |
| Others (%)† | 20.6 ± 17.9 | 19.8 ± 14.9 |
| HGB (g/dl) | 14.3 ± 0.8 | 13.5 ± 0.8 |
| HCT (%) | 54.3 ± 3.5 | 51.4 ± 3.0 |
| MCV (fl) | 57.2 ± 1.6 | 56.4 ± 0.8 |
| MCH (pg) | 15.1 ± 0.2 | 15.0 ± 0.1 |
| MCHC (g/dl) | 26.4 ± 0.9 | 26.4 ± 0.4 |
| RDW | 9.2 ± 3.5 | 8.8 ± 1.9 |
| PLT (× $10^4$/μl) | 358 ± 226 | 413 ± 327 |
| MPV (fl) | 7.4 ± 2.7 | 6.2 ± 0.7 |

*Mean ± SD for groups of 5 mice.
†Others = MONO, EOS, AND BASO.
RBC, red blood cells;
WBC, white blood cells;
LYM, lymphocytes;
NEU, neutrophils;
MONO, monocytes;
EOS, eosinophils;
BASO, basophils;
HGB, hemoglobin concentration;
HCT, hematocrit;
MCV, mean corpuscular volume;
MCH, mean cell hemoglobin;
MCHC, mean cell hemoglobin concentration;
RDW, red cell distribution width;
PLT, platelets;
MPV, mean platelet volume.

TABLE 16

Blood Chemistry Profiles for $B_6C_3F_1$ Mice Given GM-4 Intravaginally for 13 Weeks

| Parameter |  | Control | GM-4 |
|---|---|---|---|
| TP | g/dl | 4.8 ± 0.1* | 4.8 ± 0.1* |
| ALB/G | g/dl | 3.6 ± 0.2 | 3.8 ± 0.3 |
| BUN | mg/dl | 24 ± 2 | 26 ± 4 |
| CRE | mg/dl | 0.25 ± 0.05 | 0.27 ± 0.04 |
| CHO | mg/dl | 109 ± 6 | 104 ± 6 |
| TG | mg/dl | 174 ± 38 | 166 ± 33 |
| AST | IU/l | 210 ± 138 | 315 ± 206 |
| ALT | IU/l | 125 ± 87 | 103 ± 89 |
| AMY | IU/l | 1783 ± 134 | 1667 ± 377 |
| TBIL | mg/dl | 0.16 ± 0.05 | 0.18 ± 0.06 |
| GLU | mg/dl | 325 ± 23 | 310 ± 50 |
| Ca | mg/dl | 9.2 ± 0.2 | 8.6 ± 0.7 |
| P | mg/dl | 6.9 ± 1.4 | 6.4 ± 1.2 |
| Na | mg/dl | 152 ± 2 | 150 ± 3 |
| K | mg/dl | 3.9 ± 0.4 | 5.2 ± 1.4† |
| Cl | mg/dl | 109 ± 1 | 110 ± 2 |

*Mean ± SD for groups of 8 mice.
†Significantly different from control group (p < 0.05).

13-Week Necropsy/Organ Weights and Histopathology: Table 17 summarizes the terminal body weight, terminal absolute and relative organ weights observed at the conclusion of the 13-week study. No statistically significant differences were observed between the absolute and relative organ weights of test versus control mice. Microscopic examination of bone and bone marrow, brain, gut, heart, kidney, liver, lung, ovaries, pancreas, skeletal muscle, skin, spinal cord, spleen, urinary bladder, uterus, and vaginal specimens taken from the study animals did not reveal any treatment-related lesions (data not shown). No histopathological lesions were observed in the ovarian, uterine and vaginal tissues of GM-4-treated mice which suggests lack of toxicity to repeated intravaginal exposure of the lipophilic and spermicidal GM-4 formulation.

TABLE 17

Absolute and Relative Organ Weights of $B_6C_3F_1$ Mice Given GM-4 Intravaginally for 13 Weeks

| | Control | | GM-4 | |
|---|---|---|---|---|
| Organ | Absolute (g) | Relative (g%) | Absolute (g) | Relative (g%) |
| Terminal Body weight | 27.4 ± 1.6* | | 28.0 ± 3.0* | |
| Thymus | 0.09 ± 0.01* | 0.32 ± 0.03 | 0.10 ± 0.03* | 0.35 ± 0.10 |
| Lung | 0.28 ± 0.02 | 1.02 ± 0.07 | 0.29 ± 0.03 | 1.03 ± 0.10 |
| Heart | 0.14 ± 0.01 | 0.51 ± 0.03 | 0.13 ± 0.01 | 0.46 ± 0.03 |

TABLE 17-continued

Absolute and Relative Organ Weights of $B_6C_3F_1$ Mice Given GM-4 Intravaginally for 13 Weeks

| Organ | Control | | GM-4 | |
|---|---|---|---|---|
| | Absolute (g) | Relative (g%) | Absolute (g) | Relative (g%) |
| Liver | 1.62 ± 0.13 | 5.91 ± 0.47 | 1.73 ± 0.22 | 6.17 ± 0.78 |
| Pancreas | 0.15 ± 0.02 | 0.54 ± 0.07 | 0.14 ± 0.03 | 0.49 ± 0.10 |
| Spleen | 0.12 ± 0.02 | 0.43 ± 0.07 | 0.10 ± 0.01 | 0.35 ± 0.03 |
| Rep Org† | 0.17 ± 0.02 | 0.62 ± 0.07 | 0.17 ± 0.04 | 0.60 ± 0.14 |
| Kidney | 0.18 ± 0.01 | 0.65 ± 0.03 | 0.17 ± 0.01 | 0.60 ± 0.03 |
| Brain | 0.55 ± 0.02 | 2.00 ± 0.07 | 0.53 ± 0.04 | 1.89 ± 0.14 |

*Mean ± SD for groups of 10 mice.
†Reproductive organs (ovaries, uteri, and vagina).

WHI-07/GM-4 Gel Formulation Prevents Vaginal and Rectal FIV Transmission in Cat: A total of 10 cats, including 5 control cats and 5 cats treated with WHI-07(2%)/GM-4 vaginal gel formulation were challenged with an intravaginal inoculum of $7 \times 10^6$ $FIV_{Bang}$-infected FeT-J cells mixed in 0.2 mL of infected culture fluid. As shown in Table 18, WHI-07/GM-4 formulation provided 60% protection against FIV. Similarly, WHI-07/GM-4 was also able to prevent the transrectal transmission of FIV (Table 19).

TABLE 18

WHI-07(2%)/GM-4 Gel Formulation Prevents Vaginal Transmission of FIV in Cats

| Cat No. | Treatment | WB Serum | Virus Isolation PBMC | PCR PBMC | Overall Conclusion | Protection Rate |
|---|---|---|---|---|---|---|
| 1 | None | 3X | 3X | 3X | + | |
| 2 | None | 5X | 4X | 2X | + | |
| 3 | None | 1X | 2X | 2X | + | Not applicable |
| 4 | None | 5X | 5X | 6X | + | |
| 5 | None | 4X | 2X | 2X | + | |
| 6 | WHI-07/GM-4 | 0 | 0 | 0 | − | |
| 7 | WHI-07/GM-4 | 0 | 0 | 0 | − | |
| 8 | WHI-07/GM-4 | 5X | 5X | 4X | + | 60% |
| 9 | WHI-07/GM-4 | 0 | 0 | 0 | − | |
| 10 | WHI-07/GM-4 | 5X | 6X | 5X | + | |

The FIV status of cats was examined at 0, 3, 6, 9, 12, 15, and 18 weeks post intravaginal FIV challenge. The number of different assessment times with positive test results is indicated for each assay. WB: Western blot; PCR: polymerase chain reaction; PBMC: peripheral blood mononuclear cells.

TABLE 19

WHI-07(2%)/GM-4 Gel Formulation Prevents Rectal Transmission of FIV in Cats

| Cat No. | Treatment | WB Serum | Virus Isolation PBMC | PCR PBMC | Overall Conclusion | Infection Rate |
|---|---|---|---|---|---|---|
| 1 | None | 6X | 6X | 6X | + | |
| 2 | None | 0 | 0 | 0 | − | 67% |
| 3 | None | 2X | 3X | 4X | + | |
| 4 | WHI-07/GM-4 | 0 | 0 | 0 | − | |
| 5 | WHI-07/GM-4 | 0 | 0 | 0 | − | 0% |
| 6 | WHI-07/GM-4 | 0 | 0 | 0 | − | |

The FIV status of cats was examined at 0, 3, 6, 9, 12, 15, and 18 weeks post intrarectal FIV challenge. The number of different assessment times with positive test results is indicated for each assay. WB: Western blot; PCR: polymerase chain reaction; PBMC: peripheral blood mononuclear cells.

Discussion

The first objective of our studies was to determine the in vivo contraceptive efficacy of spermicidal GM-4. Since the rabbit provides a standard animal model for testing vaginal agents for antifertility activity (Castle P E, et al., *Biol Reprod*, 1997;56: 153–9.; Castle P E, et al., *Contraception*, 1998;58:51–60.), we tested the ability of intravaginally applied GM-4 to prevent pregnancy in ovulated rabbits. We confirmed that vaginal delivery of GM-4 formulation prior to artificial insemination can prevent pregnancy in the rabbit. Our in vivo contraceptive efficacy studies included term pregnancy as well as the analysis of normalcy of the resulting pregnancies. The GM-4 formulation showed remarkable contraceptive activity in the rigorous rabbit model. In two separate fertility trials, a 100% contraceptive effect was obtained despite the fact that the rabbit ejaculate used contained >1000-fold larger inseminating doses than in humans (Castle P E, et al., *Biol Reprod*, 1997;56:153–9.). To our knowledge, these experiments are the first to demonstrate the in vivo contraceptive efficacy of a GM formulation prepared from commonly used pharmaceutical excipients.

The 100% contraceptive efficacy obtained with GM-4 is most likely due to rapid spreadability of GM-4 across the vaginal mucosa as well as to its rapid spermicidal activity. In contrast, the contraceptive effect of N-9 has been shown to be highly dependent on the time interval between delivering the agent to the vagina and coitus or artificial insemination. It takes several minutes for N-9 gel to distribute in the rabbit vagina (Castle P E, et al., *Contraception*, 1998;58:51–60.). Thus, gels may be slower to mix with vaginal secretions than the GM-4 formulation. Therefore, a large excess of N-9 (400-fold greater dose) is required to achieve in vivo contraceptive activity (Castle P E, et al., *Contraception*, 1998;58:51–60.). In fact, in over-the-counter formulations, N-9 is being used at concentrations of 2 to 6% in creams and gels, 12% in foams and as high as 18% in condom lubricants. The partial (68.7%) contraceptive effect of a commercial 2% N-9 gel observed in our study when compared with 100% efficacy of GM-4 is in agreement with the high contraceptive failure rates reported for N-9 (Trussell J, et al. *Stud Fam Plann*, 1987;18:237–83.; Kulig J W, *Ped Clinic North Am*, 1989;36:717–30.; Raymond E, et al., *Obstet Gynecol*, 1999;93:896–903.). Our studies suggest that this is most likely due to incomplete mixing of semen with N-9 gel or inadequate distribution of the agent throughout the vagina.

The second objective of these studies was to determine the toxic effects, if any, resulting from repeated intravaginal application of spermicidal GM-4. Because of the potent in vitro and in vivo spermicidal activity of GM-4 formulation, it was necessary to evaluate the toxicity to vaginal mucosa particularly in the rabbit vaginal irritation test. In the rabbit vaginal tolerance test, the GM-4 formulation lacked mucosal toxicity in contrast to 4%-N-9-containing GM-4 formulation after daily application for 10 days. Our results clearly demonstrated that the GM-4 is not damaging to vaginal mucosa of the rabbit despite the fact that it was a potent spermicidal agent when added to human or rabbit semen.

The spermicidal components used for GM-4 formulation are non-toxic solubilizers for lipophilic drugs used in the preparation of a variety of topical, oral, and injectable medications. Cremophor EL® (polyethoxylated castor oil), Phospholipon® 90G (purified soya lecithin), PEG 200, propylene glycol and Captex® 300 (medium chain triglyceride), are widely used parenteral vehicles as non-toxic solubilizers for lipophilic drugs and vitamins (Castle P E, et al., *Contraception*, 1998;58:51–60.; Lundberg B B, *J Pharm Pharmacol*, 1997;49:16–21.) Cremophor EL® when used up to 10% w/v did not cause any apparent membrane damage to cell monolayers and did not cause lysis of human leukemic cells (Woodcock D M, et al., *Cancer Res*, 1990;50:4199–203.; Nerurkar M M, et al., *Pharmaceutical Research*, 1996; 13:528–34.). These components by themselves were not spermicidal in human semen. Therefore, unlike the currently used non-ionic and cationic detergent spermicides, the submicron particle-based GM-4 formulation is not likely to cause harmful side effects following repetitive intravaginal application.

In short-term toxicity studies, intravaginal administration of the lipophilic and spermicidal GM-4, to female $B_6C_3F_1$ mice for 13 weeks displayed no adverse effects on survival, growth, hematological, clinical chemistries, absolute or relative organ weights and histopathology. The kidney, liver, and pancreas function as well as the nutritional status were not affected adversely by GM-4 formulation exposure. Based on the preclinical results reported here, we are hopeful that repetitive intravaginal application of GM-4 will have no significant adverse systemic side effects in clinical settings. Experiments to formally test the safety of the intravaginally applied GM-4 on the long-term health and reproductive performance of test animal species are currently in progress.

Conclusion

Within the above examples we described the in vitro and in vivo spermicidal activity and safety of a novel pharmaceutical formulation, in the form of a gel-microemulsion GM, which contains common pharmaceutical excipients as the active ingredients. In some embodiments of the Examples, drug solubilizing agents, for example Cremophor EL® and Phospholipon® 90G, are contemplated as the active ingredients since these agents were spermicidal against highly motile fraction of sperm. Although, the individual components of GM-4 formulation alone lacked spermicidal activity in semen, the GM-4 formulation containing all eight pharmacological excipients rapidly inactivated sperm in human semen. The lack of cytotoxicity of individual components of GM-4 in human semen and their synergestic spermicidal property in a GM formulation shows uniqe clinical potential to formulate them as the active ingredients for a novel and effective vaginal contraceptive.

The microemulsion-based lipophilic and vaginal spermicide, GM-4, appears to offer several benefits for vaginal delivery including increased absorption, improved contraceptive efficacy, and decreased toxicity. Under the described conditions of its intended use, a 13-week intravaginal application of GM-4 formulation in $B_6C_3F_1$ mice did not result in systemic toxicity and no other specific target organs were identified. Therefore, the spermicidal GM-4 formulation shows unique clinical potential to become a clinically useful vaginal contraceptive for preventing the sexual transmission of STDs while preventing unwanted pregnancies. As a potent contraceptive agent which is inexpensive and devoid of mucosal toxicity, the lipophilic GM-4 formulation meets the criteria for a vaginal spermicide and warrant further evaluation in vivo in humans.

In addition, this non-toxic lipophilic gel-microemulsion formulation may also be useful for intravaginal application of anti-microbial agents to prevent the sexual transmission of diseases such as AIDS, genital herpes, gonorrhea and chlamydia.

Example 6

Synthesis of Gel-Microemulsion Formulations

Materials: Propylene glycol was obtained from Spectrum Quality Products Inc., New Brunswick, N.J. Captex® 300 was from ABITEC Corp., Janesville, Wis. Cremophor EL® was purchased from BASF Corp., Mount Olive, N.J. Phospholipon® 90G was purchased from American Lecithin Co., Danbury, Conn. Rhodigel® was from Rhodia Food Ingredients, Cranbury, N.J. Pluronic® F-68 was obtained from JRH Biosciences, Inc., Lenexa, Kans. N-9 (IGEPAL CO-630) was a generous gift from Rhone Poulenc, Cranbury, N.J.

Gel-Microemulsion Formulation: A lipophilic sub-micron (30–80 nm) particle size microemulsion, GM-144, was developed using commonly used pharmaceutical excipients through systemic mapping of ternary phase diagrams. Eccleston GM, In: Swarbrick J, Boylan J C, eds. Encyclopedia of Pharmaceutical Technology, New York: Marcel Dekker, 1992: 375–421; Tenjaria S., *Crit. Rev. Ther. Drug Carrier Syst*. 1999, 16: 461–521. The components of GM-144 formulation are listed in Table 20. The ingredients selected included, drug solubilizers and stabilizers (propylene glycol, Captex® 300, Cremophor EL®, Phospholipon® 90G, Pluronic® F-68), and a preservative (sodium benzoate). Polymer suspensions of xanthan gum (Rhodigel®) was selected as additive to the microemulsion-based system to obtain a gel with viscosity of about 1000 centipoise with high thickening capability and compatibility with vaginal mucosa. The polymer did not cause precipitation or alter the microemulsion particle size. The GM-144 was found to be very stable at ambient temperature. A submicron (30–80 nm)-particle size was verified using Nicomp Model 380 laser diode source (Particle Sizing Systems, Santa Barbara, Calif.). Viscosity measurements were made using the Brookfield digital viscometer (Model DV-II+; Brookfield Engineering Laboratories, Spoughton, Mass.).

TABLE 20

Components of GM-144 formulation

| Excipient | Type | Final concentration (%, by wt) |
|---|---|---|
| Propylene glycol | Humectant | 17.0 |
| Captex ® 300 | Lipid | 4.5 |
| Cremophor EL ® | Surfactant | 3.8 |
| Phospholipon ® 90G | Phospholipid | 3.0 |
| Rhodigel ® | Natural polymer | 1.0 |
| Pluronic ® F-68 | Surfactant | 0.4 |
| Sodium benzoate | Preservative | 0.2 |
| Water | Diluent | 70.1 |

Example 7

Spermicidal Activity of Pharmaceutical Excipients of GM-144 and of the GM-144 Formulation on Human Sperm Methods and Materials Computer-Assisted Spermicidal Assay: All donor semen specimens were obtained after informed consent and in compliance with the guidelines of the Parker Hughes Institute Institutional Review Board. The kinetics of spermicidal activity of individual components of GM-144 was quantitated using a computer-assisted sperm analyzer (Hamilton Thorne Research [Danvers, Mass.] Integrated Visual Optical System, version 10.9i instrument). D'Cruz O J, et al., *Mol. Hum. Reprod.*, 1999, 5: 421–432; D'Cruz O J, et al., *Biol. Reprod.* 1999, 50: 1419–1428; D'Cruz O J, et al., *Biol. Reprod.* 2000, 63: 196–205. The ingredients evaluated were propylene glycol (17%), Captex® 300 (4.5%), Cremophor EL® (3.8%), Phospholipon® 90G (3.0%), Rhodigel® (1%), Pluronic® F-68 (0.4%) and sodium benzoate (0.2%). The effect of duration of incubation on sperm head centroid-derived sperm motility parameters was tested by mixing an aliquot of semen with equal volume of each of the seven pharmaceutical excipients or GM-144 formulation in Biggers, Whitten, and Whittingam's medium (BWW) containing 25 mM HEPES (Irvine Scientific, Santa Ana, Calif.) and 0.3% BSA (BWW-0.3% BSA) to yield the final concentrations contained in GM-144. At timed intervals of 1, 15, 30, 45 and 60 min, 5-µl samples were transferred to two 20-µm Microcell (Conception Technologies) chambers, and sperm motility was assessed by CASA. Sperm motility in viscous samples (Phospholipon® 90G and Rhodigel®), were also determined by manual phase contrast microscopy (Olympus BX40; Olympus Corporation, Lake Success, N.Y.), and the number of motile sperm per treatment were enumerated for a total of 200 sperm. The time course test was performed in 3 separate trials, with semen obtained from five different donors.

Sperm Kinematic Parameters: For CASA, 5-µl each of sperm suspension was loaded into two 20-µm Microcell chambers placed onto a counting chamber at 37° C. and 5–8 fields per chamber were scanned for analysis. Each field was recorded for 30 sec. The Hamilton Thorne computer calibrations were set at 30 frames at a frame rate of 30 images/sec. Other settings were as follows: minimum contrast 8; minimum size 6; low-size gate, 1.0; high-size gate, 2.9; low-intensity gate, 0.6; high-intensity gate, 1.4; phase-contrast illumination; low path velocity at 10 µm/sec and threshold straightness at 80%; magnification factor, 1.95. The performance of the analyzer was periodically checked using the playback function.

The sperm kinematic parameters evaluated included numbers of motile (MOT) and progressively (PRG) motile sperm; curvilinear velocity (VCL); average path velocity (VAP); straight-line velocity (VSL); beat-cross frequency (BCF); and the amplitude of lateral head displacement (ALH) and the derivatives, straightness (STR=VSL/VAP× 100) and linearity (LIN=VSL/VCL×100). Data from each individual cell track were recorded and analyzed. For each aliquot sampled, >200 sperm were analyzed. The percentage motilities were compared with those of sham-treated control suspensions of motile sperm. The spermicidal activity of the test compound was expressed as $t_{1/2}$ values (the time taken to decrease the proportion of motile sperm by 50%).

Modified Sander-Cramer Assay: The spermicidal activity of GM-144 formulation with and without Rhodigel® was tested by a modified Sander-Cramer assay. D'Cruz O J, et al., *Mol. Hum. Reprod.*, 1999, 5: 421–432; D'Cruz O J, et al., *Contraception*, 1999, 59: 319–331. Briefly, aliquots (0.1 ml) of freshly liquefied semen were rapidly mixed with an equal volume of freshly prepared GM-144 formulation. A 5-µl sample was transferred to a 20 µm Microcell chamber (Conception Technologies) and examined immediately under a phase contrast microscope attached to a CCD camera (Hitachi Deneshi Ltd., Tokyo, Japan) and a video monitor. A commercial 2% N-9 formulation (Gynol II; Ortho Pharmaceutical Corp., Raritan, N.J.) was used as a positive control. The time required for sperm immobilization was recorded in seconds. This test was performed in nine separate trials, with fresh semen obtained from five different donors.

To assess the effect of decreasing concentrations of GM-144 and Gynol II, on sperm immobilization, aliquots of liquefied semen (1:1) were mixed with serial 2-fold dilutions (50%–0.78%) of GM-144 or Gynol II in PBS. The dilution that induced >90% sperm immobilization following a 2-min incubation was then recorded.

Figure 6:
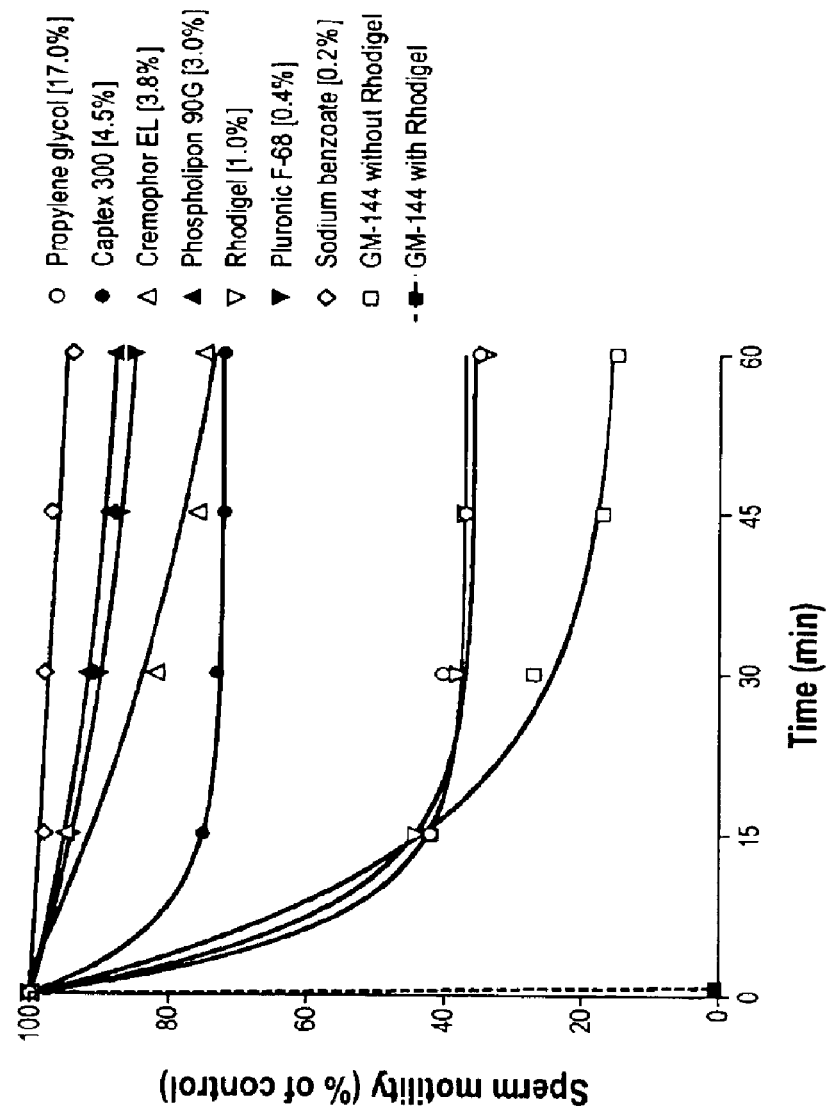
FIG. 6 shows the effect of GM-144 and individual components of GM-144 on the motility of human sperm in semen. Aliquots of liquefied semen were mixed with an equal volume of GM-144 formulations or assay medium containing the final concentrations of components of GM-144. At timed intervals, sperm motility was evaluated. GM-144 immobilized sperm in human semen in less than 30 sec, whereas the components of GM-144 formulation or microemulsion alone demonstrated variable degree of inhibition of sperm motility in human semen with slow kinetics over the time course tested.

Results:

The effect of individual components of GM-144 on the motility of sperm in human semen was evaluated by CASA. The results are shown in FIG. 6. At the final concentrations used for GM-144 formulation, Captex® 300, Cremophor EL®, Phospholipon® 90G, Pluronic® F-68, and sodium benzoate, demonstrated little or no inhibitory effects on human sperm motility ($t_{1/2}$=>60 min). Further, sperm motion kinematics using CASA confirmed that these excipients did not significantly alter the sperm motion parameters, such as the progressive velocity, straightness of the swimming pattern, linearity of the sperm tracks, beat-cross frequency, and the amplitude of lateral sperm head displacement. Whereas treatment of human semen with propylene glycol and Rhodigel® at the concentration used for GM-144 formulation, induced only partial spermicidal activity with slow kinetics ($t_{1/2}$=>24 min). Progressive sperm motility (>30%) was evident even after 60 min of exposure to these components. Similarly, the microemulsion without the Rhodigel® polymer was partially spermicidal with slow kinetics ($t_{1/2}$=>15 min). By contrast, the submicron particle size gel-microemulsion, GM-144, containing Rhodigel® as the polymer completely immobilized sperm in human semen in less than 30 sec (mean 27±4 sec; n=9) in the modified Sander-Cramer assay. Even a 1:16 dilution of GM-144 induced >50% inhibition of sperm motility in semen after a 2-min exposure. Thus, the combination of commonly used pharmaceutical excipients as a gel-microemulsion formulation was highly spermicidal in human semen.

Example 8

Preclinical Studies

Materials and Methods

Rabbits: Ninety female and 12 male, sexually mature (>6 months old; >4 Kg), specific-pathogen-free, New Zealand White rabbits were obtained from Charles River Laboratories (Wilmington, Del.). For each fertility trial, 14 does and 12 bucks were used. All rabbits were identified with specific metal ear tags. Tap water and rabbit food pellets (Teklad hi-fiber diet #7012; Harlan Teklad, Madison, Wis.) were available ad libitum. The does and bucks were maintained in separate rooms that were kept at 22±2° C. with relative humidity of 50±20% and a 12-h fluorescence light cycle. The rabbits were isolated for a minimum of 4 weeks before the fertility trials. All procedures were approved by the Parker Hughes Institute Institutional Animal Use and Care Committee. All animal husbandry operations were conducted under current USDA Guidelines.

In Vivo Contraceptive Efficacy in the Rabbit Model: For each contraceptive test, the does were divided into 3 subgroups of 14; 1) control does; 2) GM-144 group and; 3) N-9 group. Semen was obtained from bucks (n=12) of proven fertility via a prewarmed (45° C.) artificial vagina immediately before use. Sperm count and motility was assessed to ensure that the males were ejaculating good quality semen. Prior to artificial insemination, semen samples without the contamination of urine or gel were pooled and 0.5 ml (>30×10$^7$ sperm/ml) aliquots were transferred to 1 ml tuberculin syringes. Two ml of a GM-144 formulation (1000 centipoise) or Gynol II (120,000 centipoise) was applied intravaginally via a plastic tubing to a depth of 8 cm. The doe was held in a supine position during the application of 2 ml of the test agent followed by the application of 0.5 ml semen dose which was deposited within 1 min by inserting the tuberculin syringe into the vagina to a depth of 6 cm. At the time of artificial insemination, ovulation was induced by an intravenous injection of 100 IU of human chorionic gonadotropin (Sigma Chemical Co., St. Louis, Mo.) into the marginal ear vein. After ovulation and artificial insemination, the does were allowed to complete their pregnancy (31±2 days). Pregnant does were transferred to cages containing nest boxes (16×12×6 in). The litter size, weight, and the condition of each offspring at birth were recorded. The in vivo spermicidal effect of GM-144 formulation versus 2% N-9 formulation was assessed based on the level of pregnancy reduction achieved in comparison to controls and the consistency of this response. The vaginal delivery/artificial insemination and pregnancy cycle was repeated a second time.

Vaginal Irritation Test in Rabbits: For the vaginal irritation study, 6 female rabbits were treated intravaginally with 1 ml of GM-144 formulation, once per day for 10 consecutive days. Animals were sacrificed on day 11 and the reproductive tract was examined grossly and microscopically after completion of the study (Eckstein P, *J Reprod. Fertil.*, 1969, 20: 85–93.). The vaginal tissues were rapidly removed and parts of the upper (cervico-vagina), middle and lower (uro-vagina) regions of each vagina were fixed in 10% neutral-buffered formalin. Tissues were embedded in paraffin, sectioned at 4–6 μm and stained with hematoxylin and eosin and examined under ×200 and ×400 magnification using a Leica light microscope (Milton Keynes, Buckinghamshire, UK) interfaced with an image analysis system (Media Cybernetics, Silver Spring, Md.) in conjunction with a 3CCD camera (DAGE-MTI Inc., Michigan City, Ind.) for observation and analysis. Each of the three regions of vagina were examined for epithelial ulceration, edema, leukocyte infiltration, and vascular congestion. The irritation scores were assigned based on the scoring system of Eckstein et al (*J. Reprod. Fertil.*, 1969, 20: 85–93), which classifies levels of vaginal irritation as follows. Individual score: 0=none, 1=minimal, 2=mild, 3=moderate, 4=intense. The total scoring system correlates to human irritation potential as follows: total scores of 0 to 8 are acceptable, scores of 9 to 11 indicate borderline irritation potential and scores greater than 12 are potentially irritating. Results were expressed as the mean±SD values.

Statistical Analysis: Nonlinear regression analysis was used to find the $t_{1/2}$ values from the time-dependent motility loss curves using Graphpad Prism (version 2.0) software (San Diego, Calif.). The Statistical significance of differences in fertility between the groups was analyzed by Fisher's exact test. Differences were considered statistically significant if p<0.05.

Results:

In Vivo Contraceptive Activity of GM-144 versus N-9 Formulation in the Rabbit Model: Because of the rapid spermicidal activity of GM-144, we performed in vivo contraceptive efficacy studies of GM-144 in the standard rabbit model. Gynol II, a commercial contraceptive gel containing 2% N-9, was tested in the same way for comparison. In the modified Sander-Cramer assay, Gynol II completely immobilized all sperm in human or rabbit semen in less than 20 sec (mean 13±2 sec). A 1:32 dilution of Gynol II induced >90% inhibition of sperm motility in semen after a 2-min exposure and >60% of sperm were immobilized at a 1:128 dilution.

For in vivo contraceptive efficacy studies, eighty-four ovulated NZW rabbits in subgroups of 28 were artificially inseminated with fresh pooled semen with and without intravaginal application of GM-144 formulation or N-9 and allowed to complete term pregnancy. The efficacy of GM-144 formulation versus Gynol II for preventing pregnancy in the rabbit model are summarized in Table 21. In the control group, 24 out of 28 (85.7%) rabbits artificially inseminated became pregnant and delivered a total of 185 newborn rabbits. By contrast, only 6 out of 28 (21.4%) rabbits given GM-144 formulation prior to artificial insemination became pregnant (p<0.0001, Fisher's exact test) with a total of 34 new born pups. Similarly, only 7 out of 28 (25%) rabbits given Gynol II became pregnant (p<0.0001, Fisher's exact test) and delivered a total of 47 newborn rabbits. Thus, the GM-144 formulation was as effective as Gynol II as a vaginal spermicidal contraceptive. Rabbits that delivered litters following single intravaginal application of GM-144 or Gynol II prior to artificial insemination had healthy offsprings with no peri- or postnatal repercussions.

TABLE 21

Fertility of female rabbits after artificial insemination/ovulation induction with and without intravaginal application of GM-144 formulation or Gynol II containing 2% N-9

| Treatment[a] | No. of does inseminated | No. of does fertile (%) | Mean litter size (median) | Total litter size |
|---|---|---|---|---|
| None | 28 | 24 (85.7%) | 7.7 ± 3.3 | 185 |
| GM-144 | 28 | 6 (21.4%)[b] | 5.6 ± 3.1 | 34 |
| Gynol II (2%-N-9) | 28 | 7 (25.0%)[b] | 6.7 ± 1.0 | 47 |

[a]Aliquots (0.5 ml) of fresh, pooled semen obtained from fertile bucks (n = 12) were used to artificially inseminate the does within 1 min following intravaginal application of 2 ml of GM-144 formulation or Gynol II (2% N-9 gel). Does were induced to ovulate by an intravenous injection of 100 IU of hCG and allowed to complete term pregnancy.
[b]Significantly different from control by Fisher's exact test, (p < 0.0001).

Lack of Vaginal Irritation from GM-144 in the Rabbit Model: Histological evaluation of three different regions of the vaginal tissues of six rabbits given daily intravaginal application of GM-144 for 10 consecutive days showed lack of significant vaginal irritation (mean individual scores 0–2; total score 5) [Table 22]. None of the six rabbits treated with GM-144 revealed epithelial ulceration, edema, leukocyte influx, and vascular congestion characteristic of inflammation as quantitated by histological scoring according to the method of Eckstein et al. (*J. Reprod. Fertil.*, 1969, 20: 85–93.).

TABLE 22

Scoring of histological changes in the rabbit vaginal tissue after 10 days of intravaginal application of GM-144 formulation

| | Cervico-vagina (n = 6) | Mid-vagina (n = 6) | Uro-vagina (n = 6) |
|---|---|---|---|
| Epithelial ulceration | 0[a] | 0 | 0 |
| Lamina propria thickness | 1 ± 1[b,c] | 1 ± 1 | 1 ± 1 |
| Leukocyte Infiltration | 2 ± 1 | 2 ± 1 | 2 ± 1 |
| Vascular congestion | 2 ± 1 | 2 ± 1 | 2 ± 1 |
| Total score | 5 ± 1 | 5 ± 1 | 5 ± 1 |

[a]Six rabbits were administered intravaginally with 1 ml of GM-144 daily for 10 days.
[b]Mean ± SD values representing the upper (cervico-vagina), middle, and lower (uro-vagina) regions of vagina from 6 rabbits.
[c]Semiquantitative scoring criterion adapted from Eckstein et al., J. Reprod. Fertil., 1969, 20: 85–93. Individual score: 0 = none, 1 = minimal, 2 = mild, 3 = moderate, 4 = intense. Correlation to human irritation potential: total score <8 acceptable, 9–10 marginal, and ≧11 unacceptable.

Discussion

The in vitro and in vivo spermicidal activity and lack of intravaginal toxicity of a novel pharmaceutical formulation, in the form of gel-microemulsion, which contained common pharmaceutical excipients as the active ingredients have been described. Although, the individual components of GM-144 formulation alone lacked rapid spermicidal activity in semen, the gel-microemulsion, GM-144, containing all seven pharmacological excipients rapidly inactivated sperm in human semen. The kinetics of the in vitro spermicidal activity of microemulsion in semen was dramatically enhanced by the addition of the gel polymer, Rhodigel®, clearly demonstrating the synergistic effect of gel-microemulsion. The rapid spermicidal property of the lipophilic gel-microemulsion, GM-144, has unique clinical potential to provide improved methods of vaginal contraceptives in addition to being a drug delivery vehicle to reduce the risk of STD infections during sexual activity.

Since the rabbit provides a standard animal model for testing vaginal agents for antifertility activity (Castle P E, et al., *Contraception*, 1998, 58: 51–60.), we tested the ability of intravaginally applied GM-144 to prevent pregnancy in ovulated rabbits. We confirmed that vaginal delivery of GM-144 formulation prior to artificial insemination can drastically reduce pregnancy rates in the rigorous rabbit model. Our in vivo contraceptive efficacy studies included term pregnancy as well as the analysis of normalcy of the resulting pregnancies. Intravaginal application of GM-144 prior to artificial insemination resulted in a 75% contraceptive effect despite the fact that the rabbit ejaculate used in our fertility trials was in the order of several hundred human ejaculates (Castle P E, et al., *Biol. Reprod.*, 1997, 56: 153–159). Under identical conditions, Gynol II showed 71% inhibition of fertility. Despite the rapid in vitro spermicidal property of N-9, the in vivo contraceptive activity of 2% N-9 in the rabbit model has been shown to be highly dependent on the time interval between delivering the agent to the vagina and artificial insemination or coitus (Castle P E, et al., *Contraception*, 1998, 58: 51–60). Also, a large excess of N-9 is required in the vagina to achieve effective in vivo contraception as compared to the dose of N-9 needed to kill all sperm in vitro. In the present study, the rabbit ejaculate used to inseminate the does was >1000-fold larger than that of humans (Castle P E, et al., *Biol. Reprod.*, 1997, 56: 153–159). Therefore, under the experimental conditions used, a partial contraceptive activity in rabbits observed with GM-144 and Gynol II, respectively, can be considered essentially 100% contraceptive in humans (Castle P E, et al., *Contraception*, 1998, 58: 51–60; Castle P E, et al., *Biol. Reprod.*, 1997, 56: 153–159).

The second objective of these studies was to determine the toxic effects, if any, resulting from repeated intravaginal application of spermicidal GM-144. Because of the potent in vitro and in vivo spermicidal activity of GM-144 formulation, it was necessary to evaluate the toxicity to vaginal mucosa particularly in the rabbit vaginal irritation test. A correlation exists between rabbits and humans with respect to the irritation potential of vaginal contraceptive compositions. Because the constituents of GM-144 are non-toxic drug solubilizers and polymers, in the rabbit vaginal tolerance test, GM-144 lacked mucosal toxicity after daily application for 10 days. The histopathological evaluation clearly demonstrated that the GM-144 is not damaging to vaginal mucosa of the rabbit despite the fact that it was a potent spermicidal agent when added to human or rabbit semen. Because the spermicidal activity of GM-144 is not due to a detergent-type mechanism, GM-144 when used as a contraceptive is unlikely to significantly affect or inhibit the growth characteristics of vaginal flora. Thus, unlike the currently used non-ionic and cationic detergent spermicides, the submicron particle-based GM-144 formulation is not likely to cause harmful side effects following repetitive intravaginal application. Experiments to formally test the safety of the intravaginally applied spermicidal gel-microemulsion on the long-term health and reproductive performance of test animal species are currently in progress.

The components used for GM-144 formulation are non-toxic solubilizers for lipophilic drugs used in the preparation of a variety of topical, oral, and injectable medications. Propylene glycol (propane-1,2-diol), Captex® 300 (medium chain triglyceride), Cremophor EL® (polyethoxylated castor oil), Phospholipon® 90G (purified soya lecithin), and Pluronic® F-68 [poly(oxyethylene)-poly(oxypropylene)], are widely used parenteral vehicles as non-toxic solubilizers for lipophilic drugs and vitamins (Lundberg B B, *J. Pharm. Pharmacol.*, 1997, 49: 16–21; Woodcock D M, et al., *Cancer Res.*, 1990, 5: 4199–4203; Dreher F, et al., *Skin Pharmacol.*, 1996, 9: 124–129; Katz D H, et al., *Proc. Natl. Acad. Sci. U.S.A*, 1991, 88: 10825–10829). Cremophor EL® when used up to 10% w/v did not cause any apparent membrane damage to cell monolayers and did not cause lysis of human leukemic cells (Nerurkar M M, et al., *Pharm. Res.*, 1996, 13: 528–534). Pluronic® F-68 is a non-ionic polyol that does not have any intrinsic antibacterial activity. It is commonly used to protect cultured animal cells from the detrimental effects of sparging (Murhammer D W, et al., *Biotechnol. Prog.*, 1990, 6: 391–397). Pluronic® poloxamers are being used to enhance absorption of drugs through the mucus membranes. Long-term toxicity studies and clinical trials suggest that these pharmaceutical excipients are safe for human use (de Jong H J, *Therapie*, 1999, 54: 11–14). Rhodigel® (Xanthan gum) was preferred as a gel base because of its safety and wide acceptability as a pharmacological excipient for topical application (Sutherland I W, *Trends Biotechnol.*, 1998, 16: 41–46).

The microemulsion-based lipophilic and vaginal spermicide, GM-144, appears to offer several benefits for vaginal delivery including increased absorption, potent contraceptive activity, and decreased toxicity. Therefore, the spermicidal GM-144 formulation shows unique clinical potential to become a clinically useful vaginal contraceptive and a potential drug delivery vehicle for preventing the sexual transmission of STDs while preventing unwanted pregnancies. As a potent contraceptive agent which is inexpensive and devoid of mucosal toxicity, the lipophilic GM-144 formulation meets the criteria for a vaginal spermicide and warrant further preclinical evaluation. In addition, this non-toxic lipophilic gel-microemulsion may also be useful for intravaginal application of anti-microbial agents to prevent the sexual transmission of diseases such as AIDS, genital herpes, gonorrhea and chlamydia.

Conclusion

A novel, lipophilic, submicron (30–80 nm)-particle-size gel-microemulsion, GM-144, prepared from pharmaceutical excipients commonly used in topical, oral, and injectable medications was found to exhibit potent spermicidal activity, although these excipients by themselves exhibit little or no spermicidal activity in human semen. In the rabbit model, GM-144 as a vaginal contraceptive was as effective as the commercially-available detergent-type spermicide, nonoxynol-9 (N-9) gel. Repeated intravaginal application of GM-144 in the rabbit vaginal irritation test was not associated with local inflammation or damage of the vaginal mucosa or epithelium. Therefore, GM-144 shows unique clinical potential to become a clinically useful safe vaginal contraceptive and a potential drug delivery vehicle for preventing the sexual transmission of pathogens while preventing unwanted pregnancies.

Example 10

Preparation amd Characterization of GM-144 Containing WHI-07

Methods

Gel-Microemulsion Formulation of WHI-07: Formulations containing WHI-07 were prepared. The formulations were prepared generally as described in Example 4 above. Due to the lipophilic nature of WHI-07, a microemulsion-based formulation strategy was developed to contain WHI-07 in submicron (30–80 nm) particle sizes. Initially, several microemulsion compositions were screened for their drug solubility, particle size, stability, and responses to in vivo and in vitro biological models. The ingredients tested were: medium chain triglycerides, purified soya phospholipid, Pluronic® F-68, ethoxylkated castor oiul, propylene glycol, polyethylene glycol, and water. A microemulsion-based system with high soulbilizing capacity for WHI-07 was identified through systematic mapping of ternary phase diagrams, and drug solubilization study. Various polymeric were screened to produce a gel with desirable viscosity. Polymer suspensions of xanthan gum or carrageenan were added to the microemulsion-base system to obtain a gel with desirable viscosity containing 1–2% WHI-07 with high thickening capability and compatibility with microemulsions. These polymers did not casuse drug precipitation or alter the microemulsion particle size. The gel-microemulsion was found to be very stable at ambient temperature. Particle size determination was made using Nicomp Model 380 dynamic light scattering particle sizer equipped with a 15 mWatt Power Laser Diode Source (Particle Sizing Systems, Santa Barbara, Calif.). Measurements of drug concentrations were carried out by HP 1100 series HPLC and Beckman DU7500 UV-Visible spectrophotometer. Examples of the formulations prepared are described in Table 23 where % is weight %.

TABLE 23

| Additional Formulations Containing WHI-07 | |
|---|---|
| Component Name | GM-144 |
| WHI-07 | 2% |
| Captex ® 300 | 4.49% |
| Phospholipon ® 90G | 2.99% |
| Pluronic ® F-69 | 0.43% |
| Cremphor ® EL | 3.86% |
| Propylene glycol | 17.2% |
| Rhodigel ®, 1.5% | 0.96% |
| Water | Balance |

In vitro Spermicidal Activity of WHI-07 Gel Formulation: The spermicidal activity of a 2% gel frmulation of WHI-07 was tested using the modified Sander Cramer Test. Aliquots (0.1 ml) of freshly liquefied semen were rapidly mixed with equal volume of freshly prepared 2% gel-microemulsion of WHI-07. A 4-μl sample was transferred to a microscope (Olympus BX-20; Olympus Corporation, Lake Success, N.Y.) attached to a CCD camera (Hitachi Deneshi Ltd., Tokyo, Japan) and a videomonitor. The time required for sperm immobilization was recorded in seconds. This test was performed in six separate trials, with semen from three different donors.

Results

Gel-Microemulsion Formulation of WHI-07: Because WHI-07 is lipophilic, a microemulsion-based formulation was developed to achieve 2% of the drug in a submicron (30–80 nm) particle size. The selection of a suitable microemulsion base with high drug solubility was identified through systematic mapping of ternary phase diagrams and drug solubilization studies. Polymeric gels with high thickening capacity (0.2–2%) and compatibility with microemulsion system was used to achieve the desired viscosity (200–1000 centipise). Polymeric gels that did not cause drug precipitation or alter particle size were selected. In the Sander-Cramer test, the gel-microemulsion containing 2% WHI-07 immobilized all sperm in semen in less than 2 min.

Example 11

Preparation amd Characterization of GM-4 Containing DDE-4

DDE-4 is a phenyl phosphate derivative of bromomethoxy zidovudine (WHI-07) with potent anti-HIV and spermicidal activities. DDE-4 refers to 5-Bromo-6-methoxy-5,6-dihydro-AZT 5'-[p-Methoxyphenyl methoxyalaninyl phosphate]. DDE-4 also refers to Chemical Abstract index name N-[3'-azido-5-bromo-3'-deoxy-5,6-dihydro-6-methoxy-P-(4-methoxyphenyl)-5'-thymidylyl]-L-alanine methyl ester (CAS number 213982-93-5). DDE-4 has been described in the following publications: (a) D'Cruz, O. J.; Zhu, Z.; Yiv, S. H.; Chen, C.-L.; Waurzyniak, B.; Uckun, F. M. *Contraception*, 1999, 59, 69–76; (b) D'Cruz, O. J.; Venkatachalam, T. K.; Uckun, F. M. *Biol. Reprod.*, 2001, 64(1), 51–59; (c) D'Cruz, O. J.; Waurzyniak, B.; Yiv, S. H.; Uckun, F. M. *Contraception*, 2000, 61(1), 69–76; (d) D'Cruz, O. J.; Venkatachalam, T. K.; Uckun, F. M. *Biol. Reprod.*, 2000, 62(1), 37–44; and (e) D'Cruz, O. J.; Venkatachalam, T. K.; Zhu, Z.; Shih, M.-J.; Uckun, F. M. *Biol. Reprod.*, 1998, 59(3), 503–515.

Synthesis of DDE-4

Two synthetic procedures were developed for the synthesis of DDE4 (Schemes 1 and 2). The first procedure generated a mixture of four diastereomers, and the second two mixtures of two diastereomers each. In Scheme 1, the starting material DDE3 was synthesized according to the procedure of McGuigan et al., *J. Med. Chem.*, 1993, 36, 1048–1052. Compound DDE3 is a mixture of two diastereomers, because of the tetrahedral configuration at the phosphorus center. Compound DDE3 was then treated with BrOMe in methanol, converted to DDE4. The addition to 5,6-double bond of AZT proceeds in trans-(5R,6R) and trans-(5S,6S), stereochemically, thus, four isomers were observed by $^1$H NMR and HPLC. Flash chromatography provided 57% of the isolated yield.

To reduce the number of diastereomers in the mixture, a second synthetic scheme was developed (Scheme 2). The 5R,6R configuration AZT derivative (DDE1) was prepared according to the procedure of Kumar et al., *J. Med. Chem.*, 1994, 37, 4297–4306 with preparative TLC separation, which was then coupled with the phosphorochloridate, to afford the desired diastereomeric mixture.

Although the second procedure provided less diastereomers in the reaction product, the scale of synthesis is smaller than the first procedure, since preparative TLC has smaller capacity for separation.

Scheme 1

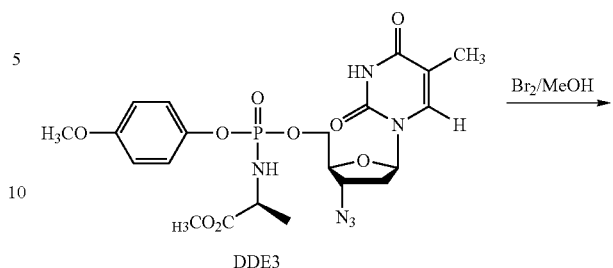

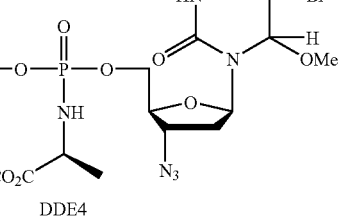

Scheme 2

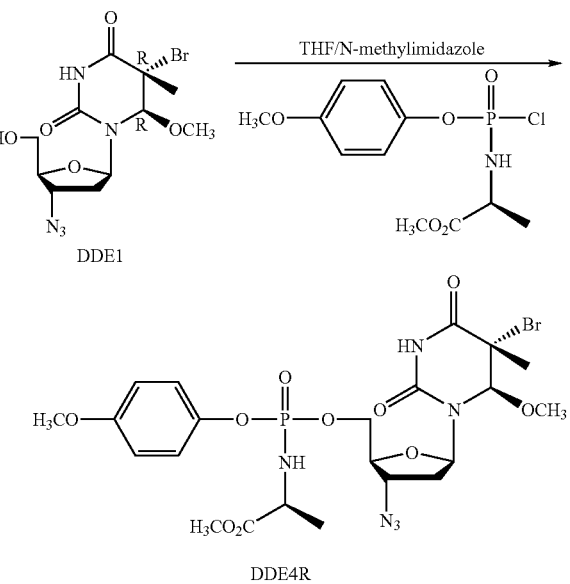

Analytical thin-layer chromatography (TLC) was performed on Merck precoated glass plates (silica gel 60, $F_{254}$, 250-μm thickness), and visualized under 254-nm UV light. Preparative TLC was performed on Whatman PK6F plates (silica gel 60 A, UV active, 1 mm thickness). The Preparative column chromatography was performed using EM silica gel 60, 230–400 mesh. NMR spectra were recorded on a Varian 300, using $CDCl_3$ with tetramethylsilane as the internal standard for $^1$H (300 MHz), solvent as the internal standard for $^{13}$C (75 MHz), or phosphoric acid as the external standard for $^{31}$P (121 MHz). Mass spectra were recorded by electrospray mode on a Finnigan Mat 95 spectrometer. HPLC data were recorded using an HP 1100 system, with a LiChrospher 100 RP-18 column (5 μm, 250–4), with water (0.1% TEA+0.1% TFA):acetonitrile= 62:38, with a flow rate of 1 mL/min and detection by UV at 222 nm. Reactions were performed in glassware which had been oven dried (120° C./overnight), and under nitrogen atmosphere. All reaction mixtures were stirred magnetically, unless otherwise noted. Solvents and reagents were used as purchased from Aldrich Chemical Co., unless otherwise stated. The yields quoted were isolated yields.

5-Bromo-6-methoxy-5,6-dihydro-3'-azidothymidine 5'-[p-methoxyphenyl methoxyalaninyl phosphate] (DDE4). A freshly prepared solution of methyl hypobromite (bromine in methanol) was added dropwise to a solution of DDE3[3] (0.538 g, 1 mmol) in anhydrous methanol (10 mL) with stirring until the yellow color of the reaction mixture persisted. The reaction was allowed to proceed for 30 min. The completion of the reaction was followed by TLC (CHCl$_3$:MeOH=95:5, v/v). The reaction mixture was neutralized to pH 6 using a solution of methanolic sodium hydroxide. Removal of the solvent in vacuo, and application of the residue to the top of a silica gel column followed by elution with chloroform-methanol (95:5, v/v) afforded a mixture of diastereomers as a viscous oil (0.372 g, 57%). $^1$H NMR (CDCl$_3$. Starred peaks are split due to diastereoisomers.) δ 7.66 (s, 1H), 7.17–7.10 (m, 2H), 6.87–6.76 (m, 2H), 6.04* (t, J=6.2 Hz, 1H), 4.88 (s, 1H), 4.33–4.25 (m, 2H), 4.07–3.98 (m, 2H), 3.82–3.68 (m, 6H), 3.56–3.40 (m, 3H), 2.46–2.31 (m, 2H), 1.96–1.91 (m, 3H), 1.43–1.33 (m, 3H); $^{13}$C NMR (CDCl$_3$) δ 173.8, 167.1, 156.7, 150.5, 143.7, 121.0, 120.9, 114.6, 114.4, 93.3*, 89.8*, 87.3, 84.7, 82.2, 81.6, 81.4, 65.5, 65.3, 61.2, 60.0, 57.9, 57.8, 56.9, 55.5, 53.6, 53.2, 52.6, 52.4, 50.3, 50.1, 49.9, 49.7, 36.6, 35.2, 30.9, 22.7, 21.0; $^{31}$P NMR (CDCl$_3$) δ 3.2, 3.1, 3.0, 2.8; ES MS m/z 649 (MH$^+$), 651; HPLC retention time 18.1 (30%), 18.7 (30%), 21.1 (18%), 22.8 (12%) min, (water: CH$_3$CN=62:38); UV λ$_{max}$ 222, 280 nm.

(5R,6R)-5-Bromo-6-methoxy-5,6-dihydro-3'-azidothymidine 5'-[p-methoxyphenyl methoxyalaninyl phosphate] (DDE4R). Compound DDE1 (0.568 g, 1.5 mmol) was dissolved in THF (15 mL). p-Methoxyphenyl methoxyalaninyl phosphorochloridate[3] (1.384 g, 4.5 mmol) and N-methylimidazole (0.72 mL, 9 mmol) were added with vigorous stirring. After overnight stirring the solvent was removed under vacuum. The residue was dissolved in chloroform and washed with saturated sodium bicarbonate solution, and then water. The organic phase was dried (MgSO$_4$) and evaporated under vacuum. The residue was purified by chromatography on silica by elution with 5% methanol in chloroform. Pooling and evaporation of appropriate fractions gave the product (0.474 g, 47%). $^1$H NMR (CDCl$_3$. Starred peaks are split due to diastereoisomers.) δ 7.59 (s, 1H), 7.17–7.11 (m, 2H), 6.88–6.78 (m, 2H), 6.05* (t, J=6.2 Hz, 1H), 4.89 (s, 1H), 4.32–4.25 (m, 2H), 4.05–4.03 (m, 2H), 3.79–3.72 (m, 6H), 3.45, (s, 1.5H) 3.44 (s, 1.5H), 2.47–2.35 (m, 2H), 1.97 (s, 1.5H), 1.93 (s, 1.5H), 1.39 (t, J=4.5 Hz, 1.5H), 1.36 (t, J=6.6 Hz, 1.5H); $^{31}$P NMR (CDCl$_3$) δ 3.1, 2.9; MALDI-TOF MS m/z 672.4 (MNa)$^+$; HPLC retention time 9.9 (40%), 10.3 (60%) min, (water: CH$_3$CN=70:30); UV λ$_{max}$ 222, 279 nm.

GM-4 Conatining 2% DDE-4

GM-4 containing 2% DDE-4 was prepared in a similar manner to GM-4 containing 2% WHI-07 as described in Example 4 above. The resulting gel microemulsion had a pH of 7.2 and was a translucent gel with the following composition:

|  | % (by weight) |
| --- | --- |
| DDE-4 | 2.0 |
| Captex ® 300 | 10.7 |
| Phospholipon ® 90G | 5.0 |
| Cremophor EL ® | 7.5 |
| Propylene glycol | 4.2 |
| PEG 200 | 4.2 |
| Seaspan ® Carrageenan | 0.9 |
| Viscarin ® Carrageenan | 0.9 |
| Sodium benzoate | 0.2 |
| Water | 64.4 |

Spermicidal Activity of GM-4 Containing 2% DDE-4

Modified Sander-Cramer Assay: The spermicidal activity of GM-4 formulation, as produced in Example 1, was tested by a modified Sander-Cramer assay (Sander F V, et al., *Hum Fertil,* 1941;6:134–7.; D'Cruz O J, et al., *Contraception,* 1999;59:319–31.). Briefly, aliquots (0.1 ml) of freshly liquefied semen were rapidly mixed with an equal volume of freshly prepared GM-4 formulation or GM-4 formulation containing 2% DDE-4. A 5-µl sample was transferred to a 20 µm Microcell chamber (Conception Technologies) and examined immediately under a phase contrast microscope (Olympus BX-20; Olympus Corporation, Lake Success, N.Y.) attached to a CCD camera (Hitachi Deneshi Ltd., Tokyo, Japan) and a videomonitor. The time required for sperm immobilization was recorded in seconds. This test was performed in six separate trials, with semen obtained from six different donors.

One set of tests were performed using rabbit semen and another set of tests were perforemed using human semen. The results are presented in Tables 24 and 25.

TABLE 24

Sander-Cramer test using rabbit semen

| GM-4 | GM-4 with 2% DDE-4 |
| --- | --- |
| 2.12 ± 1.09 min | 4.37 ± 0.54 min |
| Not Determined | 2.01 ± 0.54 min |

TABLE 25

Sander-Cramer test using human semen

| GM-4 | GM-4 with 2% DDE-4 |
| --- | --- |
| 2.21 ± 1.19 min | 1.58 ± 1.17 min |
| 10.3 ± 4.0 min | 8.25 ± 3.34 min |

All publications, patents, and patent documents described herein are incorporated by reference as if fully set forth. The invention described herein may be modified to include alternative embodiments. All such obvious alternatives are within the spirit and scope of the invention, as claimed below.

What is claimed is:

1. A spermicidal composition comprising a gel-microemulsion comprising an oil-in-water microemulsion and a polymeric hydrogel,
   wherein the oil-in-water microemulsion comprises
   a lipid;
   one or more pharmaceutically acceptable surfactants, wherein the surfactant comprises one or more phospholipids and one or more non-ionic surfactants, and wherein the non-ionic surfactant comprises a block copolymer of ethylene oxide and propylene oxide;

one or more pharmaceutically acceptable humectants; and water.

2. A spermicidal composition comprising a gel-microemulsion comprising an oil-in-water microemulsion and a polymeric hydrogel, wherein the oil-in-water microemulsion comprises:

a lipid comprising a fatty acid glyceride ester;

one or more pharmaceutically acceptable surfactants;

one or more pharmaceutically acceptable humectants; and water.

3. The composition of claim 2, wherein the fatty acid glyceride ester comprises a monoglyceride or a triglyceride.

4. The composition of claim 3, wherein the fatty acid glyceride ester comprises a medium chain $C_6$–$C_{12}$ fatty acid glyceride ester.

5. The composition of claim 4, wherein the medium chain $C_6$–$C_{12}$ fatty acid glyceride ester is a triglyceride of caprylic/capric acid.

6. A spermicidal composition comprising a gel-microemulsion comprising:

an oil-in-water microemulsion, wherein the oil-in-water microemulsion comprises a lipid;

one or more pharmaceutically acceptable surfactants;

one or more pharmaceutically acceptable humectants; and water;

and a polymeric hydrogel selected from the group consisting of natural gel-forming polymers selected from the group consisting of carrageenan, xanthan gum, gum karaya, gum acacia, locust bean gum, and guar gum; and synthetic gel-forming polymers.

7. The composition of claim 6, wherein the natural gel-forming polymers are selected from the group consisting of carrageenan and xanthan gum.

8. A spermicidal composition comprising a gel-microemulsion comprising an oil-in-water microemulsion and a polymeric hydrogel, wherein the oil-in-water microemulsion comprises:

a lipid;

one or more pharmaceutically acceptable surfactants, wherein the surfactant comprises one or more non-ionic surfactants;

one or more pharamaceuticaily acceptable humectants; water; and one or more preservatives selected from the group consisting of sodium benzoate, methyl parabens, propyl parabens, thimerisal, and sorbic acid.

9. The composition of claim 8, wherein the preservative is sodium benzoate.

10. A spermicidal composition comprising a gel-microemulsion comprising an oil-in-water microemulsion and a polymeric hydrogel, wherein the oil-in-water microemulsion comprises:

a lipid;

one or more pharmaceutically acceptable surfactants;

one or more pharmaceutically acceptable humectants; and water, wherein the composition has a viscosity in the range of about 200 to about 1000 centipoise.

11. A spermicidal composition comprising a gel-microemulsion comprising an oil-in-water microemulsion and a polymeric hydrogel, wherein the oil-in-water microemulsion comprises:

a lipid;

one or more pharmaceutically acceptable surfactants;

one or more pharmaceutically acceptable humectants; and water, wherein the composition has a submicron particle size in the range of about 30 to about 80 nm.

12. A spermicidal composition comprising a gel-microemulsion comprising an oil-in-water microemulsion and about 0.5% to about 4% by weight of polymeric hydrogel, wherein the oil-in-water microemulsion comprises:

about 2% to about 25% by weight lipid;

about 3% to about 30% by weight surfactant of one or more pharmaceutically acceptable surfactants;

about 2% to about 24% of one or more pharmaceutically acceptable humectants; and water;

about 0% to about 0.5% preservative.

13. The composition of claim 12, wherein the composition comprises:

in the range of about 6% to about 23% by weight lipid;

in the range of about 4% to about 17% by weight surfactant;

in the range of about 3% to about 12% humectant;

in the range of about 1% to about 2% polymer gel; and in the range of about 0% to about 0.3% preservative.

14. The composition of claim 13, wherein the composition comprises:

in the range of about 8% to about 15% by weight lipid;

in the range of about 8% to about 15% by weight surfactant;

in the range of about 5% to about 10% humectant;

in the range of about 1.2% to about 1.8% polymer gel; and in the range of about 0% to about 0.2% preservative.

15. The composition of claim 12, wherein the oil-in-water microemulsion comprises:

about 2% to about 20% by weight lipid;

about 4% to about 17% by weight of one or more pharmaceutically acceptable surfactants;

about 5% to about 22% of one or more pharmaceutically acceptable humectments; and water;

about 0.5% to about 2% weight of polymeric hydrogel; and about 0.1% to about 0.3% preservative.

16. The composition of claim 15, wherein the composition comprises:

in the range of about 3% to about 10% by weight lipid;

in the range of about 4% to about 10% by weight surfactant;

in the range of about 12% to about 19% humectant;

in the range of about 0.8% to about 1.2% polymer gel; and in the range of about 0.15% to about 0.2% preservative.

17. A spermicidal composition comprising a gel-microemulsion comprising an oil-in-water microemulsion and about 1% to about 2% by weight of natural polymer gel, wherein the oil-in-water microemulsion comprises:

in the range of about 6% to about 23% medium chain $C_6$–$C_{12}$ triglyceride;

in the range of about 3% to about 10% ethoxylated castor oil;

in the range of about 1.5% to about 6% phospholipid;

in the range of about 1.5% to about 6% propylene glycol;

in the range of about 1.5% to about 6% polyethylene glycol; and water; and about 0% to about 0.2% preservative.

18. The composition of claim 17, wherein the composition comprises:

in the range of about 8% to about 15% medium chain $C_6$–$C_{12}$ triglyceride;

in the range of about 5% to about 9% ethoxylated castor oil;

in the range of about 3% to about 6% phospholipid;

in the range of about 3% to about 6% propylene glycol;

in the range of about 3% to about 6% polyethylene glycol;

in the range of about 1.2% to about 1.8% natural polymer gel; and in the range of about 0.1% to about 0.2% preservative.

19. A spermicidal composition comprising a gel-microemulsion comprising an oil-in-water microemulsion and about 0.6% to about 2% by weight of natural polymer gel, wherein the composition comprises:

in the range of about 2% to about 20% medium chain $C_6$–$C_{12}$ triglyceride;

in the range of about 1% to about 10% ethoxylated castor oil;

in the range of about 0.2% to about 1% block copolymer of ethylene oxide and propylene oxide;

in the range of about 1% to about 10% phospholipid;

in the range of about 2% to about 22% propylene glycol; and in the range of about 0% to about 0.3% preservative.

20. The composition of claim 19, wherein the composition comprises:

in the range of about 3% to about 10% medium chain $C_6$–$C_{12}$ triglyceride;

in the range of about 2% to about 5% ethoxylated castor oil;

in the range of about 0.2% to about 0.8% block copolymer of ethylene oxide and propylene oxide;

in the range of about 1% to about 5% phospholipid;

in the range of about 12% to about 19% propylene glycol;

in the range of about 0.8% to about 1.2% natural polymer gel; and in the range of about 0% to about 0.2% preservative.

21. The composition of claim 17 further comprising one or more therapeutic agents.

22. The composition of claim 21 wherein the therapeutic agent comprises up to 10% by weight of the composition.

23. The composition of claim 20, wherein the lipid is a triglyceride of caprylic/capric acid, and the natural polymer gel is xanthan gum.

24. The composition of claim 18, wherein the lipid is a triglyceride of caprylic/capric acid, and the natural polymer gel is carrageenans.

25. A process for preparing a pharmaceutical composition according to claim 1, the process comprising:

(a) combining surfactants, hydrophilic components, and lipids in a container;

(b) mildly heating and mixing the combined the components until a clear and homogeneous microemulsion is formed;

(c) removing the microemulsion from heat and allowing to cool to about room temperature;

(d) adding two parts of a polymeric hydrogel to each part of microemulsion; and (e) mixing the polymeric hydrogel and microemulsion to form the composition of claim 1.

26. The process of claim 25, wherein the composition has a viscosity in the range of about 200 centipoise to about 1000 centipoise.

27. The process of claim 25, wherein the composition has a submicron particle size in the range of about 30 nm to about 80 nm.

28. A process for preparing a pharmaceutical composition according to claim 2, the process comprising:

(a) combining surfactants, hydrophilic components, and lipids in a container;

(b) mildly heating and mixing the combined the components until a clear and homogeneous microemulsion is formed;

(c) removing the microemulsion from heat and allowing to cool to about room temperature;

(d) adding two parts of a polymeric hydrogel to each part of microemulsion; and (e) mixing the polymeric hydrogel and microemulsion to form the composition of claim 2.

29. The process of claim 28, wherein the composition has a viscosity in the range of about 200 centipoise to about 1000 centipoise.

30. The process of claim 28, wherein the composition has a submicron particle size in the range of about 30 nm to about 80 nm.

31. A process for preparing a pharmaceutical composition according to claim 6, the process comprising:

(a) combining surfactants, hydrophilic components, and lipids in a container, (b) mildly heating and mixing the combined the components until a clear and homogeneous microemulsion is formed;

(c) removing the microemulsion from heat and allowing to cool to about room temperature;

(d) adding two parts of a polymeric hydrogel to each part of microemulsion; and (e) mixing the polymeric hydrogel and microemulsion to form the composition of claim 6.

32. The process of claim 31, wherein the composition has a viscosity in the range of about 200 centipoise to about 1000 centipoise.

33. The process of claim 31, wherein the composition has a submicron particle size the range of about 30 nm to about 80 nm.

34. A process for preparing a pharmaceutical composition according to claim 10, the process comprising:

(a) combining surfactants, hydrophilic components, and lipids in a container;

(b) mildly heating and mixing the combined the components until a clear and homogeneous microemulsion is formed;

(c) removing the microemulsion from heat and allowing to cool to about room temperature;

(d) adding two parts of a polymeric hydrogel to each part of microemulsion; and (e) mixing the polymeric hydrogel and microemulsion to form the composition of claim 10.

35. The process of claim 34, wherein the composition has a submicron particle size in the range of about 30 nm to about 80 nm.

36. A process for preparing a pharmaceutical composition according to claim 11, the process comprising:
(a) combining surfactants, hydrophilic components, and lipids in a container;
(b) mildly heating and mixing the combined the components until a clear and homogeneous microemulsion is formed;
(c) removing the microemulsion from heat and allowing to cool to about room temperature;
(d) adding two parts of a polymeric hydrogel to each part of microemulsion; and
(e) mixing the polymeric hydrogel and microemulsion to form the composition of claim 11.

37. The process of claim 36, wherein the composition has a viscosity in the range of abou 200 centipoise to about 1000 centipoise.

38. A process for preparing a pharmaceutical composition according to claim 12, the process comprising:
(a) combining surfactants, hydrophilic components, and lipids in a container;
(b) mildly heating and mixing the combined the components until a clear and homogeneous microemulsion is formed;
(c) removing the microemulsion from heat and allowing to cool to about room temperature;
(d) adding two parts of a polymeric hydrogel to each part of microemulsion; and
(e) mixing the polymeric hydrogel and microemulsion to form the composition of claim 12.

39. The process of claim 38, wherein the composition has a viscosity in the range of about 200 centipoise to about 1000 centipoise.

40. The process of claim 38, wherein the composition has a submicron particle size in the range of about 30 nm to about 80 nm.

41. A process for preparing a pharmaceutical composition according to claim 17, the process comprising:
(a) combining surfactants, hydrophilic components, and lipids in a container;
(b) mildly heating and mixing the combined the components until a clear and homogeneous microemulsion is formed;
(c) removing the microemulsion from heat and allowing to cool to about room temperature;
(d) adding two parts of a polymeric hydrogel to each part of microemulsion; and
(e) mixing the polymeric hydrogel and microemulsion to form the composition of claim 17.

42. The process of claim 41, wherein the composition has a viscosity in the range of about 200 centipoise to about 1000 centipoise.

43. The process of claim 41, wherein the composition has a submicron particle size in the range of about 30 nm to about 80 nm.

44. A process for preparing a pharmaceutical composition according to claim 19, the process comprising;
(a) combining surfactants, hydrophilic components, and lipids in a container;
(b) mildly heating and mixing the combined the components until a clear and homogeneous microemulsion is formed;
(c) removing the microemulsion from heat and allowing to cool to about room temperature;
(d) adding two parts of a polymeric hydrogel to each part of microemulsion; and
(e) mixing the polymeric hydrogel and microemulsion to form the composition of claim 19.

45. The process of claim 44, wherein the composition has a viscosity in the range of about 200 centipoise to about 1000 centipoise.

46. The process of claim 44, wherein the composition has a submicron particle size in the range of about 30 nm to about 80 nm.

47. A method for inhibiting the motility of sperm, the method comprising:
a) providing a spermicidal composition of claim 1; and
b) contacting the sperm with the spermicidal composition.

48. The method of claim 47, wherein the sperm is contacted with the spermicidal composition intervaginally.

49. A method for inhibiting the motility of sperm, the method comprising:
a) providing a spermicidal composition of claim 2; and
b) contacting the sperm with the spermicidal composition.

50. The method of claim 49, wherein the sperm is contacted with the spermicidal composition intervaginally.

51. A method for inhibiting the motility of sperm, the method comprising:
a) providing a spermicidal composition of claim 6; and
b) contacting the sperm with the spermicidal composition.

52. The method of claim 51, wherein the sperm is contacted with the spermicidal composition intervaginally.

53. A method for inhibiting the motility of sperm, the method comprising:
a) providing a spermicidal composition of claim 10; and
b) contacting the sperm with the spermicidal composition.

54. The method of claim 53, wherein the sperm is contacted with the spermicidal composition intervaginally.

55. A method for inhibiting the motility of sperm, the method comprising:
a) providing a spermicidal composition of claim 11; and
b) contacting the sperm with the spermicidal composition.

56. The method of claim 55, wherein the sperm is contacted with the spermicidal composition intervaginally.

57. A method for inhibiting the motility of sperm, the method comprising:
a) providing a spermicidal composition of claim 12; and
b) contacting the sperm with the spermicidal composition.

58. The method of claim 57, wherein the sperm is contacted with the spermicidal composition intervaginally.

59. A method for inhibiting the motility of sperm, the method comprising:
a) providing a spermicidal composition of claim 17; and
b) contacting the sperm with the spermicidal composition.

60. The method of claim 59, wherein the sperm is contacted with the spermicidal composition intervaginally.

61. A method for inhibiting the motility of sperm, the method comprising:
a) providing a spermicidal composition of claim 19; and
b) contacting the sperm with the spermicidal composition.

62. The method of claim 61, wherein the sperm is contacted with the spermicidal composition intervaginally.

* * * * *

UNITED STATES PATENT AND TRADEMARK OFFICE
CERTIFICATE OF CORRECTION

| | | |
|---|---|---|
| PATENT NO. | : 7,064,114 B2 | Page 1 of 1 |
| APPLICATION NO. | : 09/957434 | |
| DATED | : June 20, 2006 | |
| INVENTOR(S) | : Yiv et al. | |

It is certified that error appears in the above-identified patent and that said Letters Patent is hereby corrected as shown below:

Title Page, (75) Inventors: "Faith M. Uckun, White Bear" should read --Fatih M. Uckun, White Bear--

Col. 3, line 21: "additional superficial agents" should read --additional spermicidal agents--

Col. 30, line 67: "solved in a 10 ml" should read --dissolved in a 10 ml--

Col. 53, line 62: "GM-4 Conatining 2%" should read --GM-4 Containing 2%--

Col. 55, line 48, claim 8: "more pharmaceuitcaily acceptable" should read --more pharmaceutically acceptable--

Col. 58, line 55, claim 34: "the combined the" should read --the combined--

Col. 59, line 22, claim 38: "the combined the" should read --the combined--

Signed and Sealed this

Twenty-fourth Day of October, 2006

JON W. DUDAS
*Director of the United States Patent and Trademark Office*